United States Patent
Landberg et al.

(10) Patent No.: US 11,840,732 B2
(45) Date of Patent: Dec. 12, 2023

(54) DIAGNOSTIC METHODS

(71) Applicant: ISCAFF PHARMA AB, Gothenburg (SE)

(72) Inventors: Göran Landberg, Gothenburg (SE); Anders Ståhlberg, Gothenburg (SE); Joakim Håkansson, Borås (SE)

(73) Assignee: ISCAFF PHARMA AB, Gothenburg (SE)

( * ) Notice: Subject to any disclaimer, the term of this patent is extended or adjusted under 35 U.S.C. 154(b) by 64 days.

(21) Appl. No.: 16/347,763

(22) PCT Filed: Nov. 3, 2017

(86) PCT No.: PCT/EP2017/078176
§ 371 (c)(1),
(2) Date: May 6, 2019

(87) PCT Pub. No.: WO2018/083231
PCT Pub. Date: May 11, 2018

(65) Prior Publication Data
US 2019/0284638 A1    Sep. 19, 2019

(30) Foreign Application Priority Data
Nov. 7, 2016    (GB) ..................... 1618743

(51) Int. Cl.
*A01N 43/00* (2006.01)
*A01N 43/46* (2006.01)
*A61K 31/55* (2006.01)
*C12Q 1/6886* (2018.01)
*G01N 33/574* (2006.01)
*C12N 5/071* (2010.01)
*C12M 1/12* (2006.01)

(52) U.S. Cl.
CPC .......... *C12Q 1/6886* (2013.01); *C12M 25/14* (2013.01); *C12N 5/0631* (2013.01); *G01N 33/57415* (2013.01); *C12N 2502/30* (2013.01); *C12N 2533/90* (2013.01); *C12Q 2600/106* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2002/0115208 A1 | 8/2002 | Mitchell et al. |
| 2005/0013870 A1 | 1/2005 | Freyman et al. |
| 2006/0099675 A1 | 5/2006 | Benard |
| 2007/0248638 A1 | 10/2007 | Van Dyke et al. |
| 2008/0160069 A1 | 7/2008 | Maniotis et al. |
| 2012/0213706 A1 | 8/2012 | Banerjee et al. |
| 2013/0190893 A1 | 7/2013 | Roock et al. |
| 2013/0195811 A1* | 8/2013 | Wang ............. A61L 27/24 424/93.7 |
| 2013/0253415 A1 | 9/2013 | Sano et al. |
| 2013/0344490 A1 | 12/2013 | Kim |
| 2014/0023723 A1 | 1/2014 | Leach et al. |
| 2014/0274802 A1 | 9/2014 | Shepherd et al. |
| 2015/0282885 A1 | 10/2015 | King et al. |
| 2015/0337261 A1 | 11/2015 | Li et al. |
| 2016/0030635 A1 | 2/2016 | Bhatia et al. |
| 2016/0040132 A1 | 2/2016 | Sears et al. |
| 2016/0109450 A1 | 4/2016 | Lee et al. |

FOREIGN PATENT DOCUMENTS

| | | |
|---|---|---|
| CN | 104195099 A | 12/2014 |
| EP | 1500697 B1 | 1/2005 |
| KR | 10-2014-0071172 A | 6/2014 |
| KR | 10-2015-0052413 A | 5/2015 |
| WO | 2010/120329 A1 | 10/2010 |
| WO | 2012/122640 A1 | 9/2012 |
| WO | 2013/003234 A1 | 1/2013 |
| WO | 2013/050962 A1 | 4/2013 |
| WO | 2013/155114 A1 | 10/2013 |
| WO | 2015/017784 A1 | 2/2015 |
| WO | 2015/185912 A1 | 12/2015 |
| WO | 2016/023140 A1 | 2/2016 |

OTHER PUBLICATIONS

Ngobili et al. ("Remodeling of tannic acid crosslinked collagen type I induces apoptosis in ER+ breast cancer cells." Anticancer Research 35.3 (2015): 1285-1290) (Year: 2015).*

Dunne et al. (Human decellularized adipose tissue scaffold as a model for breast cancer cell growth and drug treatments, Biomaterials, vol. 35, Issue 18, 2014, pp. 4940-4949).*

Anders et al., HTSeq-a Python framework to work with high-throughput sequencing data. Bioinformatics. Jan. 15, 2015;31(2):166-9.

Anders et al., HTSeq-a Python framework to work with high-throughput sequencing data. BioRxiv, 4 pages, Aug. 13, 2014.

Axelson et al., Hypoxia-induced dedifferentiation of tumor cells—a mechanism behind heterogeneity and aggressiveness of solid tumors. Semin Cell Dev Biol. Aug.-Oct. 2005;16(4-5):554-63.

(Continued)

*Primary Examiner* — Layla Soroush

(74) *Attorney, Agent, or Firm* — McCarter & English, LLP

(57) ABSTRACT

A method for determining one or more tumour properties in a subject with a tumour, the method comprising:—seeding a cell-free scaffold obtained from the tumour with cancer cells;—culturing the cancer cells in the scaffold;—assaying the cultured cancer cells for the presence of target molecules indicative of the expression of one or more genes in the cells; and—determining one or more tumour properties based on the results of the assay.

13 Claims, 24 Drawing Sheets
Specification includes a Sequence Listing.

(56) References Cited

OTHER PUBLICATIONS

Conley et al., Antiangiogenic agents increase breast cancer stem cells via the generation of tumor hypoxia. Proc Natl Acad Sci U S A. Feb. 21, 2012;109(8):2784-9.
Croft et al., Reactome: a database of reactions, pathways and biological processes. Nucleic Acids Res. Jan. 2011;39(Database issue):D691-7.
Dobin et al., STAR: ultrafast universal RNA-seq aligner. Bioinformatics. Jan. 1, 2013;29(1):15-21.
Dunne et al., Human decellularized adipose tissue scaffold as a model for breast cancer cell growth and drug treatments. Biomaterials. Jun. 2014;35(18):4940-9.
Freeman, A Set of Measures of Centrality Based on Betweenness. Sociometry. 1977;40(1):35-41.
Generali et al., Hypoxia-inducible factor-1alpha expression predicts a poor response to primary chemoendocrine therapy and disease-free survival in primary human breast cancer. Clin Cancer Res. Aug. 1, 2006;12(15):4562-8.
Harrow et al., GENCODE: the reference human genome annotation for the ENCODE Project. Genome Res. Sep. 2012;22(9):1760-74.
Hellstrom et al., Towards the development of a bioengineered uterus: comparison of different protocols for rat uterus decellularization. Acta Biomater. Dec. 2014;10(12):5034-5042.
Jiang et al., Synthetic spike-in standards for RNA-seq experiments. Genome Res. Sep. 2011;21(9):1543-51.
Love et al., Moderated estimation of fold change and dispersion for RNA-seq data with DESeq2. Genome Biol. 2014;15(12):550, 21 pages.
Mora et al., iRefR: an R package to manipulate the iRefindex consolidated protein interaction database. BMC Bioinformatics. Nov. 24, 2011;12:455, 13 pages.
Picelli et al., Smart-seq2 for sensitive full-length transcriptome profiling in single cells. Nat Methods. Nov. 2013;10 (11):1096-8.
Pons et al., Computing communities in large networks using random walks. arXiv:physics/0512106v1 [physics.soc-ph] 20 pages, Dec. 12, 2005.
Pons et al., Computing Communities in Large Networks Using Random Walks. Journal of Graph Algorithms and Applications. 2006;10(2):191-218.
Prasad et al., Human Protein Reference Database—2009 update. Nucleic Acids Res. Jan. 2009;37(Database issue): D767-72.
Scarritt et al., A review of cellularization strategies for tissue engineering of whole organs. Front Bioeng Biotechnol. Mar. 3, 20150;3:43, 17 pages.
Shaw et al., A detailed mammosphere assay protocol for the quantification of breast stem cell activity. J Mammary Gland Biol Neoplasia. Jun. 2012;17(2):111-7.
Stahlberg et al., RT-qPCR work-flow for single-cell data analysis. Methods. Jan. 2013;59(1):80-8.
Subramanian et al., Gene set enrichment analysis: a knowledge-based approach for interpreting genome-wide expression profiles. Proc Natl Acad Sci U S A. Oct. 25, 2005;102(43):15545-50.
Yu et al., ReactomePA: an R/Bioconductor package for reactome pathway analysis and visualization. Mol Biosyst. Feb. 2016;12(2):477-9.
Akrap et al., Identification of Distinct Breast Cancer Stem Cell Populations Based on Single-Cell Analyses of Functionally Enriched Stem and Progenitor Pools. Stem Cell Reports. Jan. 12, 2016;6(1):121-36.
Cazzaniga et al., Human Prostate Tissue-derived Extracellular Matrix as a Model of Prostate Microenvironment. Eur Urol Focus. Oct. 2016;2(4):400-408.
Lu et al., Development of an acellular tumor extracellular matrix as a three-dimensional scaffold for tumor engineering. PLOS One. Jul. 29, 2014;9(7):e103672. 13 pages.
United Kingdom Search Report for Application No. GB1618743.7, dated Sep. 8, 2017, 4 pages.
International Search Report for Application No. PCT/EP2017/078176, dated Feb. 9, 2018, 5 pages.
Bohonowych et al., Extracellular Hsp90 mediates an NF-κB dependent inflammatory stromal program: implications for the prostate tumor microenvironment. Prostate. Apr. 2014;74(4):395-407.
Landberg et al., Patient-derived scaffolds uncover breast cancer promoting properties of the microenvironment. Biomaterials. Mar. 2020;235:119705.
Naba et al., Extracellular matrix signatures of human primary metastatic colon cancers and their metastases to liver. BMC Cancer. Jul. 18, 2014;14:518.
Zuehlke et al., Regulation and function of the human HSP90AA1 gene. Gene. Oct. 1, 2015;570(1):8-16.
Kaushik et al., From transformation to metastasis: deconstructing the extracellular matrix in breast cancer. Cancer Metastasis Rev. Dec. 2016;35(4):655-67.
European Office Action for Application No. 17798169.2, dated Nov. 4, 2021, 5 pages.

\* cited by examiner

| MCF7 and scaffold proteins | MDA231 and scaffold proteins | MCF7, MDA231 and scaffold proteins |
|---|---|---|
| REACTOME_ADAPTIVE_IMMUNE_SYSTEM | REACTOME_ADAPTIVE_IMMUNE_SYSTEM | REACTOME_ADAPTIVE_IMMUNE_SYSTEM |
| REACTOME_AXON_GUIDANCE | REACTOME_AXON_GUIDANCE | REACTOME_AXON_GUIDANCE |
| REACTOME_CELL_CELL_COMMUNICATION | REACTOME_CELL_CELL_COMMUNICATION | REACTOME_CELL_CELL_COMMUNICATION |
| REACTOME_CELL_SURFACE_INTERACTIONS_AT_THE_VASCULAR_WALL | REACTOME_CELL_SURFACE_INTERACTIONS_AT_THE_VASCULAR_WALL | REACTOME_CELL_SURFACE_INTERACTIONS_AT_THE_VASCULAR_WALL |
| REACTOME_COLLAGEN_FORMATION | REACTOME_COLLAGEN_FORMATION | REACTOME_COLLAGEN_FORMATION |
| REACTOME_DEVELOPMENTAL_BIOLOGY | REACTOME_COMPLEMENT_CASCADE | REACTOME_DEVELOPMENTAL_BIOLOGY |
| REACTOME_EXTRACELLULAR_MATRIX_ORGANIZATION | REACTOME_DEVELOPMENTAL_BIOLOGY | REACTOME_EXTRACELLULAR_MATRIX_ORGANIZATION |
| REACTOME_GLYCOSAMINOGLYCAN_METABOLISM | REACTOME_EXTRACELLULAR_MATRIX_ORGANIZATION | REACTOME_GLYCOSAMINOGLYCAN_METABOLISM |
| REACTOME_HEMOSTASIS | REACTOME_GLYCOSAMINOGLYCAN_METABOLISM | REACTOME_HEMOSTASIS |
| REACTOME_IMMUNE_SYSTEM | REACTOME_HDL_MEDIATED_LIPID_TRANSPORT | REACTOME_IMMUNE_SYSTEM |
| REACTOME_INNATE_IMMUNE_SYSTEM | REACTOME_HEMOSTASIS | REACTOME_INNATE_IMMUNE_SYSTEM |
| REACTOME_INTEGRIN_CELL_SURFACE_INTERACTIONS | REACTOME_IMMUNE_SYSTEM | REACTOME_INTEGRIN_CELL_SURFACE_INTERACTIONS |
| REACTOME_KERATAN_SULFATE_BIOSYNTHESIS | REACTOME_INNATE_IMMUNE_SYSTEM | REACTOME_KERATAN_SULFATE_BIOSYNTHESIS |
| REACTOME_KERATAN_SULFATE_KERATIN_METABOLISM | REACTOME_INTEGRIN_ALPHAIIB_BETA3_SIGNALING | REACTOME_KERATAN_SULFATE_KERATIN_METABOLISM |
| REACTOME_L1CAM_INTERACTIONS | REACTOME_INTEGRIN_CELL_SURFACE_INTERACTIONS | REACTOME_L1CAM_INTERACTIONS |
| REACTOME_METABOLISM_OF_CARBOHYDRATES | REACTOME_KERATAN_SULFATE_KERATIN_METABOLISM | REACTOME_METABOLISM_OF_CARBOHYDRATES |
| REACTOME_NCAM1_INTERACTIONS | REACTOME_L1CAM_INTERACTIONS | REACTOME_NCAM1_INTERACTIONS |
| REACTOME_NCAM_SIGNALING_FOR_NEURITE_OUT_GROWTH | REACTOME_LIPOPROTEIN_METABOLISM | REACTOME_NCAM_SIGNALING_FOR_NEURITE_OUT_GROWTH |
| REACTOME_PLATELET_ACTIVATION_SIGNALING_AND_AGGREGATION | REACTOME_METABOLISM_OF_CARBOHYDRATES | REACTOME_PLATELET_ACTIVATION_SIGNALING_AND_AGGREGATION |
| REACTOME_POST_TRANSLATIONAL_PROTEIN_MODIFICATION | REACTOME_NCAM1_INTERACTIONS | REACTOME_POST_TRANSLATIONAL_PROTEIN_MODIFICATION |
| REACTOME_RESPONSE_TO_ELEVATED_PLATELET_CYTOSOLIC_CA2_ | REACTOME_NCAM_SIGNALING_FOR_NEURITE_OUT_GROWTH | REACTOME_RESPONSE_TO_ELEVATED_PLATELET_CYTOSOLIC_CA2_ |
| REACTOME_SEMA3A_PAK_DEPENDENT_AXON_REPULSION | REACTOME_PLATELET_ACTIVATION_SIGNALING_AND_AGGREGATION | REACTOME_SEMAPHORIN_INTERACTIONS |
| REACTOME_SEMAPHORIN_INTERACTIONS | REACTOME_POST_TRANSLATIONAL_PROTEIN_MODIFICATION | REACTOME_SIGNALING_BY_EGFR_IN_CANCER |
| REACTOME_SIGNALING_BY_EGFR_IN_CANCER | REACTOME_REGULATION_OF_COMPLEMENT_CASCADE | REACTOME_SIGNALING_BY_PDGF |
| REACTOME_SIGNALING_BY_PDGF | REACTOME_RESPONSE_TO_ELEVATED_PLATELET_CYTOSOLIC_CA2_ | |
| | REACTOME_SEMAPHORIN_INTERACTIONS | |
| | REACTOME_SIGNALING_BY_EGFR_IN_CANCER | |
| | REACTOME_SIGNALING_BY_PDGF | |

Figure 18.

DIAGNOSTIC METHODS

CROSS-REFERENCE TO RELATED APPLICATIONS

This application is a U.S. national stage filing, under 35 U.S.C. § 371(c), of International Application No. PCT/EP2017/078176, filed on Nov. 3, 2017, which claims priority to United Kingdom Application No. 1618743.7, filed on Nov. 7, 2016. The entire contents of each of the aforementioned applications are incorporated herein by reference.

FIELD OF THE INVENTION

The invention relates to methods for diagnosing or prognosing tumour properties in a subject having a tumour, such as a breast tumour. The invention further relates to the use of the methods to determine suitability of treatment for a subject, or to determine efficacy of treatment in a subject, as well as to methods for treating subjects having a tumour.

BACKGROUND TO THE INVENTION

Cancer is a major societal challenge that affects an increasing number of people. Breast cancer, for example, affects approximately one out of eight women. Besides the difficulties associated with prolonged treatment periods and related side effects, there is a substantial risk that a cancer such as breast cancer will spread and cause metastatic disease. Despite a slightly improved survival for cancer sufferers in general there are major drawbacks with the existing therapies as they do not target the cancer stem cell/epithelial-mesenchymal transition (EMT) niche and there is substantial under-treatment due to lack of efficient therapies. These therapy resistant subpopulations of cancer cells are probably responsible for malignant properties and need to be controlled in order to prevent disease recurrences (Conley, S J. et al. Antiangiogenic agents increase breast cancer stem cells via the generation of tumour hypoxia. Proc Natl Acad Sci USA 109, 2784-2789, 2012). The other problem with the existing treatment schedules for cancers such as breast cancer is over-treatment due to lack of treatment predictive information guiding clinicians in treatment decision and choices.

SUMMARY OF THE INVENTION

In a first aspect, the invention provides a method for determining one or more tumour properties in a subject with a tumour, the method comprising:
  seeding a cell-free scaffold obtained from the tumour with cancer cells;
  culturing the cancer cells in the scaffold;
  assaying the cultured cancer cells for the presence of target molecules indicative of the expression of one or more genes in the cells; and
  determining one or more tumour properties based on the results of the assay.

In one embodiment, the one or more genes may be one or more markers of tumour progression. In one embodiment, the one or more genes may be selected from Table G.

In a second aspect, the invention provides a method for determining a suitable treatment for a subject with a tumour, the method comprising:
  determining one or more tumour properties in the subject by a method according to the first aspect; and
  determining a suitable treatment based on the tumour properties of the tumour.

In a third aspect, the invention provides a method for determining or monitoring efficacy of a treatment for a subject with a tumour, the method comprising:
  (a):
    seeding a cell-free scaffold, obtained from the tumour before the treatment has been provided to the subject, with cancer cells;
    culturing the cancer cells in the scaffold; and
    assaying the cultured cancer cells for the presence of target molecules indicative of the expression of one or more genes in the cells;
  (b):
    seeding a cell-free scaffold, obtained from the tumour after the treatment has been provided to the subject, with cancer cells;
    culturing the cancer cells in the scaffold;
    assaying the cultured cancer cells for the presence of target molecules indicative of the expression of one or more genes in the cells;
  and
  (c) comparing the results of the assays in (a) and (b).

In a fourth aspect, the invention provides a method for determining likely efficacy of a treatment for subject with a tumour, the method comprising:
  (a)
    seeding a cell-free scaffold obtained from the tumour with cancer cells;
    culturing the cancer cells in the scaffold;
    assaying the cultured cancer cells for the presence of target molecules indicative of the expression of one or more genes in the cells;
  (b) applying the treatment to the scaffold comprising the cancer cells;
  (c) assaying the cultured cancer cells after the treatment has been applied, for the presence of target molecules indicative of the expression of one or more genes in the cells;
  and
  (d) comparing the results of the assays in (a) and (b).

In a fifth aspect, the invention provides a method for determining one or more tumour properties in a subject with a tumour, the method comprising:
  assaying a sample comprising a scaffold obtained from the tumour for one or more proteins selected from any one or more of Tables B-G; and
  determining one or more tumour properties in the subject based on the results of the assay.

In a sixth aspect, the invention provides a method for determining a suitable treatment for a subject with a tumour, the method comprising:
  determining one or more tumour properties in the subject by a method according to the fifth aspect; and
  determining a suitable treatment based on the tumour properties of the tumour.

In a seventh aspect, the invention provides a method for determining or monitoring efficacy of a treatment for subject with a tumour, the method comprising:
  assaying a sample comprising a scaffold, obtained from the tumour before the treatment has been provided to the subject, for one or more proteins selected from any one or more of Tables B-G;

assaying a sample comprising a scaffold, obtained from the tumour after the treatment has been provided to the subject, for one or more proteins selected from any one or more of Tables B-G; and comparing the results of the assay carried out before the treatment with the results of the assay carried out after the treatment.

In an eighth aspect, the invention provides a method of treating a subject with a tumour, the method comprising:

determining the suitability or efficacy of a treatment in the subject by a method according to any of the second, third, fourth, sixth or seventh aspects; and applying the treatment to the subject.

In a ninth aspect the invention provides a cancer treatment for use in treating a subject with a tumour, wherein said cancer treatment has been determined as suitable for or effective in the subject by a method according to any of second, third, fourth, sixth or seventh aspects.

In a tenth aspect, the invention provides a method of treating subject with a tumour, the method comprising:

determining one or more tumour properties in the subject by a method according to the first or fifth aspects;

selecting a suitable treatment based on the one or more tumour properties; and providing the treatment to the subject.

Except for where the context requires otherwise, references to the methods of the invention may be taken as encompassing methods of any of the aspects herein. Embodiments disclosed in respect of one method or use should also be taken as applicable to the other methods or uses of the invention, unless incompatible, or otherwise stated.

BRIEF DESCRIPTION OF THE FIGURES

FIG. 18—Gene set enrichment analyses (GSEA) indicating the overlap for the top hundred reactomes enriched for among scaffold proteins as well as for upregulated genes in MCF7 and MDA231 breast cancer cells based on NGS analyses of scaffold cultures in comparison with 2D growth.

DESCRIPTION OF THE SEQUENCES

Figure 1:
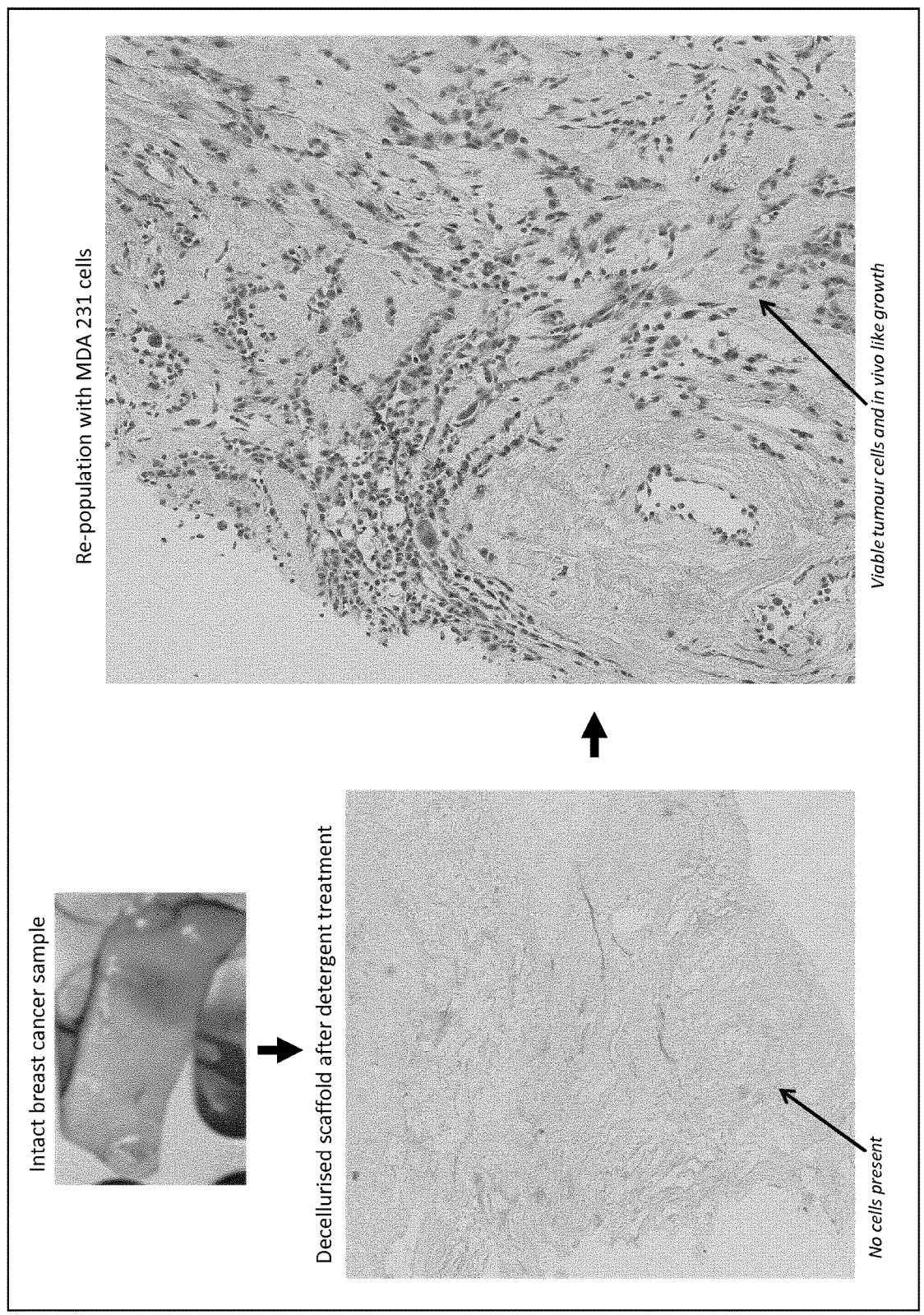
FIG. 1—A workflow in tumour scaffold production.

SEQ ID NO: 1—an adapter-ligated oligo-dT 5'-AAGCAGTGGTATCAACGCAGAGTACT$_{30}$VN-3'

SEQ ID NO: 2—template switching oligo 5'-AAGCAGTGGTATCAACGCAGAGTACATrGrG+G-3' with rG=riboguanosine and +G=locked nucleic acid modified guanosine SEQ ID NO 3—IS PCR primer 5'-AAGCAGTGGTATCAACGCAGAGT-3'

DETAILED DESCRIPTION OF THE INVENTION

The invention herein is concerned with new tests which can be used to characterise tumours, especially breast cancer tumours, based on the composition and properties of cell-free scaffolds obtained from the tumours.

The present inventors have surprisingly found that cell-free scaffold isolated from a primary breast cancer tumour can act as a diagnostic and prognostic tool in determining clinically relevant properties of the tumour.

Cancer cells are surrounded by and actively interact with the microenvironment, including the extracellular matrix surrounding the tumour. (Axelson, H. et al. "*Hypoxia-induced dedifferentiation of tumor cells—a mechanism behind heterogeneity and aggressiveness of solid tumors*". Semin Cell Dev Biol 16, 554-63, 2005; Generali, D. et al. "*Hypoxia-inducible factor-1 alpha expression predicts a poor response to primary chemo-endocrine therapy and disease-free survival in primary human breast cancer*". Clin Cancer Res 12, 4562-8, 2006.)

The present inventors have developed a cell culture platform using cell-free scaffold from tumours, such as primary breast cancer tumours, infiltrated with cancer cells, which mimics in vivo growth conditions.

The complexity of in vivo tumour growth is in strict contrast to most model systems used in cancer research today. The in vitro models used are represented by cell cultures of cancer cell lines growing on plastics under high oxygen supply and immense growth factor activation. The in vivo animal models, using mainly immunocompromised mice, at least in part create more in vivo like cancer growth conditions by the use of implanted human tumours in the form of xenografts. Compared with the in vitro models, such in vivo model systems can be used for drug testing and studies of cancer growth in a more complex environment, but they have several limitations associated with immunocompromised mice as well as non-human stromal reactions. In particular, breast cancer cell growth in xenografts does not mimic in vivo growth in patients as the cells tend to be less infiltrative and also to have large central necrotic areas due to rapid cell division in relation to angiogenic support. This creates an artificial cancer growth system that might be superior to less complex cell cultures but is still not close enough to real in vivo conditions.

In contrast to these animal models, the cell-free scaffold based culture system developed by the inventors mimics in vivo growth conditions. The inventors have shown that a series of changes are induced in the cancer cells cultured in the scaffold, including changes in differentiation, in epithelial-mesenchymal transition (EMT) (a process by which epithelial cells de-differentiate to become mesenchymal stem cells) and in proliferation, with a final considerable cancer stem cell expansion in the cell population. The inventors have further found that scaffolds from different patients vary in their ability to promote cancer stem cell features, with some scaffolds inducing more EMT features while others preserve a differentiated and proliferative phenotype in the cancer cells. Importantly, this variation in scaffolds has been linked to clinical properties of the original tumours from which the scaffolds were obtained. For example, more clinically aggressive and/or recurrent tumours have scaffolds which are particularly strong in promoting EMT features in cancer cells cultured within them.

Thus the inventors have found that cancer cells cultured in the scaffolds can act as reporter cells, providing information about the characteristics of the scaffold, and by extension, of the original source tumour. By monitoring the cultured cancer cells for changes in processes such as proliferation, differentiation, cancer stem cell-ness (pluripotency) or EMT (by testing the cells for expression of suitable markers of these processes) it is possible to determine properties of the original source tumour from which the scaffold was derived. These properties can then be used in diagnosis or prognosis. It is believed that use of patient scaffolds and reporter cells in this way has not previously been described in the art.

The inventors have also carried out mass spectrometry analyses of scaffolds isolated from primary breast cancer tumours to identify a number of proteins in the scaffolds. The inventors have identified subgroups of scaffolds based on protein composition. When the subgroups were compared with clinical characteristics of the original source tumours, it was found that the subgrouping based on protein composition mirrored grouping based on tumour properties such as tumour grade and tumour proliferation. Therefore the inventors have found that protein composition of scaffold can be used to determine clinically relevant properties of the original source tumour, and have identified particular informative proteins.

In addition to the above, by applying a combined bioinformatics approach, to the scaffold protein data, and next generation RNA-sequencing (NGS) data obtained from the cancer cells cultured in the scaffolds (indicating transcriptional changes in the cells), the inventors were able to identify an overlap between pathways in which scaffold proteins are enriched, and up- or down-regulated genes in the cells. By further analysis, the inventors identified scaffold proteins and associated regulated cellular genes in three important pathways or modules, as well as key scaffold proteins and associated regulated cellular genes representative of the most central processes. Without wishing to be bound by theory, the inventors believe that there is a functional link between the scaffold proteins and the regulated cellular genes in a module or pathway. It is believed that the scaffold proteins influence gene expression in the cells, and that this has a role in mediating the changes in cellular processes such as proliferation, differentiation, cancer stem cell-ness (pluripotency) or EMT which influence tumour progression. Therefore, by assaying a scaffold sample for the presence of one or more of the identified proteins, or by assaying cancer cells cultured in cell-free scaffold for expression of one or more of the identified genes, it is possible to assess the influence that the scaffold has on cellular gene expression and processes, and this in turn is informative about the clinical properties of the original source tumour.

The diagnostic and prognostic assays developed by the inventors also find use in selecting treatments for tumours, monitoring tumour treatments, and providing tumour treatments as described herein.

Thus the present methods and uses allow treatments more focused on subpopulations of cancer cells and the interplay with the microenvironment, in contrast to today's long-standing therapy strategies employing broad and unspecific targeting of cancer cells. The methods also provide means for monitoring how the microenvironment actually affects cancer progression. Today, there is no such method available and novel diagnostic tools are indeed needed.

In order to assist the understanding of the present invention, certain terms used herein will now be further defined in the following paragraphs.

Tumour Properties

The invention provides methods for determining one or more properties of a tumour.

A tumour generally refers to a swelling in a part of the body caused by an abnormal growth of tissue. A tumour may be benign or malignant (cancerous).

A cancerous tumour may be assigned a particular grade, with higher grade indicating a more aggressive tumour. Tumour grade is usually assigned according to the appearance of the tumour cells, for example under a microscope. Grading systems for tumours are known to the skilled person.

Higher grade tumours are sometimes referred to as progressive tumours. A progressive tumour is generally more aggressive than a non-progressive tumour. Typically, a progressive tumour has one or more of: increased invasiveness, higher malignancy grade or malignancy potential, increased risk of recurrence, increased resistance to treatment, and/or increased tumour proliferation, compared to a non-progressive tumour.

Tumour properties as used herein refer to any clinically relevant characteristics of a tumour. Tumour properties may be those associated with, or indicative of, a progressive tumour. Such tumour properties may be those which are significant in determining tumour progression, for example, properties which are useful for distinguishing progressive tumours from non-progressive tumours. Suitable tumour properties may include, for example, invasiveness, migration, malignancy grade or malignancy potential, risk of recurrence, resistance to treatment, and/or tumour proliferation. By assessing one or more of these tumour properties, the present methods may be used to identify progressive tumours (or tumours which are likely to develop into progressive tumours) and distinguish these from non-progressive tumours. The methods may also be used to identify non-progressive cancerous tumours or benign tumours. Thus the present methods may be used to classify tumours according to the properties determined, for example, invasive (including likely to become invasive) or non-invasive, recurrent (or likely to become recurrent) or non-recurrent.

The present methods may also be used to predict likely response to treatment.

In this way, the present methods are useful both in diagnosing a tumour or class of tumour in a subject, and also in predicting the way in which a tumour is likely to develop in a subject in the future, i.e. in prognosis. Properties such as invasiveness or malignancy grade may be particularly useful in diagnosis. Malignancy grade may also be particularly useful in prognosis. It will be appreciated that other factors may also be taken into account in making a diagnosis or prognosis. For example, diagnosis may also take into account varying cell shapes. Prognosis may also depend on, for example, expression of hormonal receptors, presence of lymph-node metastases, tumour size, expression of oncogenes as HER2, patient age, or RNA expression based tests.

It will be appreciated that a benign tumour should have a less tumour-promoting scaffold. Accordingly, it will be understood that a benign tumour will show substantially no markers of a progressive tumour.

Progressive tumours typically require more aggressive forms of treatment than non-progressive tumours. Distinguishing progressive tumours, or tumours that are likely to become progressive, from non-progressive or benign tumours therefore enables clinicians to select the most appropriate treatment for a tumour.

A Subject

The methods and medical uses herein are practiced in respect of a subject having a tumour. The subject may be one in need of determination of tumour properties, or of a treatment for the tumour. The subject may be a human or animal. Suitably the subject may be a female. The subject may be a mammal, for example, a human, a primate, a dog, cat, a rat or a mouse. Suitably a subject may be a human subject. The subject may be a patient undergoing medical care, or an individual requesting medical care.

A suitable subject may be one in whom the tumour has been determined to be cancerous. Suitable cancerous tumours are described herein, and include, for example breast cancer tumour. Such a subject may be a cancer patient, in particular a breast cancer patient.

A suitable subject may be one believed to have a progressive tumour, such as a progressive breast cancer tumour. For example, a subject may have symptoms consistent with a progressive tumour. Alternatively, a subject may lack some or all symptoms consistent with a progressive tumour.

Alternatively, a subject may be one believed to be at risk of developing a progressive tumour, such as a progressive breast cancer tumour, for example, because of familial history or genetic predisposition.

It will be appreciated that a subject who may gain benefit from the methods of treatment herein may be one in whom tumour properties are determined by the assessment conducted as part of the methods of the first and fifth aspects of the invention.

A Tumour

A tumour as referred to herein may be any suitable tumour. A tumour may be benign or malignant. A tumour may be of any suitable tissue. In particular, a tumour may be a breast tumour.

A tumour as referred to herein has a scaffold as described herein. The cells of such a tumour typically exist in a microenvironment or niche, with which the cells interact. For example, the tumour cells may exist in an extracellular matrix or stroma.

A suitable tumour may be a malignant tumour of a suitable cancer. Examples of suitable cancers with solid tumours include: breast cancer, lung cancer, prostate cancer, colon cancer, skin cancer, liver cancer, ovarian cancer, urinary bladder cancer, oesophageal cancer, and pancreatic cancer.

Examples of suitable cancers with non-solid tumours include lymphomas and leukamaemia.

In one aspect the tumour is not a tumour of the liver, e.g. a liver cancer tumour. In one aspect, the tumour is not a tumour of the pancreas, e.g. apancreatic cancer tumour. A tumour may be a primary cancer tumour.

A tumour of particular interest is a breast tumour, in particular, a breast cancer tumour, such as a ductal breast cancer tumour.

A tumour, such as any of those described, may be one which is believed to be progressive, or likely to become progressive.

A tumour from which a scaffold (e.g. a cell-free scaffold) is obtained may be referred to herein as a "source tumour".

Scaffolds and Cell-Free Scaffolds

The methods herein make use of a scaffold obtained from a tumour in a subject.

The extracellular matrix of a tumour generally comprises a collection of extracellular molecules, including proteins, secreted by cells that provides structural and/or biochemical support to the surrounding cells. The network of extracellular molecules constitutes a 3-dimensional scaffold for cells in the tumour. Typically, the scaffold provides a microenvironment for the tumour cells with which the cells can interact. A tumour scaffold may comprise, for example collagen and various tumour promoting factors as growth factor as well as inhibitors affecting tumour cell behaviours.

A cell-free scaffold generally refers to decellularised tumour tissue. Suitably, a cell-free scaffold comprises decellularised extracellular material obtained from the tumour, in which the original 3-dimensional structure is substantially preserved. Suitably the bioactivity of the scaffold is substantially preserved. A cell-free scaffold suitably allows effective attachment, migration, proliferation and 3-dimensional organisation of cells cultures therein. Generally the decellularised scaffold is substantially free of cells, in particular tumour cells. This may be assessed by any suitable means. Merely by way of example, sectioning and microscopic visualisation may be used to determine the presence of absence of nuclei which are indicative of cells, or DNA analysis may be used. Substantially free means that cells are not detectable in the assessments.

A sample comprising scaffold from a tumour may be prepared using methods known in the art from, for example, a biopsy.

A cell-free scaffold may be obtained from a tumour using suitable decellularising methods to remove cells while preserving the basic tumour scaffold composition. Suitable methods are known in the art, (an example is provided in Thompson A et al, Acta Bio Material 12, 5034-5042 (2014)) and are described herein in the Examples. For example, decellularising methods often employ a prolonged mild detergent treatment.

Merely by way of example, a decellularising method may comprise subjecting a suitable tumour sample (for example, a suitable section taken from a tumour sample) to one or more (e.g. 2, 3, 4 or more) detergent washes, often referred to as decellularisation cycles. Any suitable detergent may be used, for example SDS, Triton X-100, NP40, Tween 20. After each cycle, a small tissue extract may be screened for the presence of absence of cells, for example, by screening for nuclei. Typically, the cycles are continued until cells are not detectable.

Decellularisation cycles may be followed by one or more washes (for example, in distilled water or a suitable buffer) to remove cell debris. Decellularised samples may be sterilised using a suitable sterilising agent.

In one embodiment, a method herein may additionally comprise obtaining a cell-free scaffold from a tumour, or from a suitable tumour sample.

Seeding of Cell-Free Scaffolds with Cancer Cells and Culture of Cancer Cells

In some of the methods herein, a cell-free scaffold derived from a tumour is recellularised with cancer cells. The infiltrated cancer cells can then act as "reporter cells" as changes occurring in the cells (as assessed by marker gene expression) provide information about the malignancy inducing properties of the scaffold, and so the properties of the source tumour.

The process of recellularising the scaffold with the cancer cells typically comprises seeding the scaffold with the cancer cells, and culturing the cells under suitable conditions. Methods for seeding scaffolds with cells, and for culturing cells in the scaffolds are known in the art. For example, suitable methods are described in Scarritt M E, Pashos N C and Bunnell B A (2015) "*A review of cellularization strategies for tissue engineering of whole organs*". Front. Bioeng. Biotechnol. 3:43. doi: 10.3389/fbioe.2015.00043 (Front. Bioeng. Biotechnol., March 2015, Vol3, Article 43, pp1-17).

Suitable methods are described in the present Examples. For example, suitable cancer cells may be added to a suitable sample of cell-free scaffold in suitable media and incubated under conditions suitable for cell growth.

In one aspect, cells are cultured in the scaffolds for 2-3 weeks before assay according to the present methods.

Cancer Cells

Any suitable cancer cells may be used to repopulate the scaffolds. Suitable cells may be determined according to the tumour from which the scaffold has been obtained. The cells may, for example, be of the same tissue type or cancer type as the tumour from which the cell-free scaffold has been obtained. The cells may be breast cancer cells, especially where the cell-free scaffold is from a breast cancer tumour. Cells of a suitable cancer cell line may be used. Non-limiting examples of breast cancer cell lines include MCF7 cells, MDA231 cells and T47D cells (available from ATCC).

Suitably, the cancer cells are not cancer cells taken from the same patient tumour as the scaffold, i.e the cancer cells are not cancer cells taken from the source tumour.

Alternatively, the cancer cells may be cancer cells taken from the same patient tumour as the scaffold, i.e the cancer cells may be cancer cells taken from the source tumour.

Markers of Tumour Progression.

In the method of the first aspect and related methods and uses, the cultured cancer cells are assayed for the presence of target molecules indicative of the expression of one or more genes in the cells.

In one embodiment the one or more genes may be one or more markers of tumour progression.

Tumour progression is generally believed to be associated with particular changes in the tumour cells. For example, there may be changes in differentiation, proliferation, EMT and/or cancer stem-cellness (pluripotency) in the tumour cells. Without wishing to be bound by theory, it is believed that the apparent proliferative property of progressive tumours is most likely preceded by a genuine increase or quality change of cancer stem cells and EMT properties. An increase in for example EMT, which makes epithelial cells become mesenchymal like, is further linked to migration and infiltrating properties which makes the tumour more malignant with a higher chance of initiating metastases. These changes in cancer stem cell and EMT features will affect the balance of proliferative and differentiated cancer cells causing a decrease in differentiated cells, and (at least initially) a decrease in proliferating cells. Markers of tumour progression are generally molecules (typically biological molecules) which are indicative of tumour progression. For example, such markers may be representative of one or more cellular processes associated with progression. A marker may be indicative of any of the cellular changes described above. Markers may comprise, for example, markers of proliferation, markers of differentiation, markers of stem cells (pluripotency), in particular cancer stem cells, or markers of the epithelial-mesenchymal transition (EMT). Examples of such markers are presented in Table A.

It may be that in some cases, one or more markers of proliferation may be useful in determining proliferative properties. Similarly, it may be that, in some cases, one or more EMT markers may be particularly useful in determining tumour migration or invasive properties.

Suitably, the one or more markers of tumour progression include markers for more than one cellular process associated with progression, for example, 2, 3 or all 4 of the processes described above. Obtaining information about more than one process can offer reliability or detail in determining tumour properties. Additionally or alternatively, the one or more markers of tumour progression may include more than one marker for the same process, for example, any of the cellular processes described above.

A marker may act as an indicator of progression in any suitable way. Typically, marker expression (for example, an increase or decrease in expression compared to a suitable control) acts an indicator.

Any suitable markers of tumour progression may be used in the present methods. Suitable markers are known in the art.

It may be that particular markers are particularly suitable for use in connection with scaffolds from particular tumour types in the present methods. These can be determined by the skilled person using appropriate control samples, and the methods described herein.

Examples of markers of tumour progression are listed in Table A. Suitably, at least one of the one or more tumour progression markers referred to in the method of the first aspect is selected from these markers.

Suitably, at least one of the one or more tumour progression markers referred to in the method of the first aspect is selected from CD44v2, SOX2, SNAIL2(SLUG), VIM, ESR1, ERBB2(HER2), MiK67 and CCNA2.

This is particularly where the source tumour is a breast cancer tumour, in particular ductal breast cancer tumour, for example ER(+ve) ductal breast cancer. The present inventors have shown that differences in expression of these markers in reporter cells cultured in cell-free tumour scaffold derived from ductal breast cancer tumours, allows differentiation between tumour scaffolds from different patients.

At least one of the markers may be SNAIL2(SLUG) or VIM, in particular VIM. The inventors have shown that expression of each of these markers in reporter cells cultured in cell-free tumour scaffold is associated with breast cancer recurrence in the ductal breast cancer tumour from which the scaffold is derived. Moreover, SLUG and VIM expression changes were also significantly linked to recurrences using univariate analyses, and VIM was further independently linked to disease recurrences in multi-variate analyses. SLUG or VIM, in particular VIM, may also be particularly useful in determining malignancy grade.

Genes in Table G

In one embodiment, the one or more genes referred to in the method of the first aspect may be selected from the genes listed in Table G.

As described herein, the inventors have identified a number of genes in cancer cells cultured in cell-free scaffold, which are involved in common pathways or modules with particular scaffold proteins.

The genes identified by the inventors are listed in Table G, in Modules 1, 2 and 3 and "Highly Central". Module 1 represents "signaling" pathways, and consists of proteins and genes associated with: signal transduction, signaling by SCF-KIT, downstream signal transduction and signaling by VEGF, VEGFA-VEGFR2. Module 2 represents "repair and stress" pathways and consists of proteins and genes associated with DNA Repair, Cellular responses to stress, Cytosolic sensors of pathogen-associated DNA, Generic Transcription Pathway and SUMOylation. Module 3 represents "DNA-replication" pathways and includes proteins and genes associated with: Synthesis of DNA, DNA Replication, M/G1 Transition and DNA Replication Pre-Initiation.

In Table G, lists of genes are presented for each of the cancer cell lines: MCF7 and MDA231. Genes are listed as upregulated or downregulated in these cells when the cells are grown in the scaffolds.

It is believed that the scaffold proteins in a particular Module influence expression of the genes in that Module, and this in turn mediates changes in the cells associated with tumour progression. By assaying expression of one or more of these genes in the cultured cells, it is possible to assess the effects of the scaffold on the cells, and so determine properties of the original source tumour.

The one or more genes may be selected from any of Modules 1, 2 or 3, or from the "Highly Central" list, or from any combination of these. In one embodiment the one or more genes is selected from the "Highly Central" list of genes in Table G. These are believed to be key genes, involved in initiating and mediating the changes in cells associated with tumour progression, in particular, cancer stem cell and EMT functions.

It will be appreciated that the one or more genes may be selected from more than one Module or list, and/or that expression of more than one gene may be assayed. In one instance the method may comprise assaying for expression of more than one gene from the same Module.

The one or more genes may be selected from an MCF7 and/or MDA231 list in any Module. Suitably, where the cultured cancer cells are MCF7 cells, the one or more genes may be selected from an MCF7 list, and/or where the cultured cancer cells are MDA231 cells, the one or more genes may be selected from an MDA231 list.

Where a gene is indicated to be upregulated in Table G, an assay is typically for an increase in expression. Where a gene is indicated to be down-regulated in Table G, an assay is typically for a decrease in expression.

It will be appreciated that any one or more the genes listed in Table G may represent a target for cancer therapy.

Target Molecules

Target molecules indicative of the expression of one or more genes are any molecules which are representative of gene expression in the cultured cancer cells. Such target molecules may be representative of gene expression either directly or indirectly. By way of example, a suitable target molecule which is directly representative of gene expression may comprise an RNA transcript. Alternatively, a suitable target molecule may comprise a protein. For example, a suitable target molecule which is indirectly representative of gene expression may comprise a protein encoded by the gene.

Examples of target molecules may also include lipids or carbohydrates.

It will be appreciated that the nature of the target molecule may be chosen in order to be consistent with use in a preferred assaying system.

Target molecules may be obtained from the cultured cancer cells using methods known to the skilled person, and appropriate to the nature of the target molecule. Typically, cells are processed in order to provide a sample comprising the target molecules which is suitable for use in an assay.

Scaffold Protein Markers

In the method of the fifth aspect, a sample comprising scaffold obtained from a tumour is assayed for one or more specified proteins. Suitably the scaffold is a cell-free scaffold. However, a sample may comprise an intact tumour sample.

In the method, a sample comprising scaffold obtained from the tumour (in particular a breast cancer tumour) is assayed for one or more proteins selected from any one or more of Tables B-G.

The one or more proteins may be selected from Table B. The inventors have shown that these proteins can be used to subgroup scaffolds in a way that mirrors clinical properties of the source tumours, such as higher or lower grade. Therefore the proteins are useful in classifying source tumours by tumour property.

Proteins listed in PCA Cluster 1 in Table B typically show a negative association with tumour proliferation or tumour grade. Proteins listed in PCA Cluster 2 in Table B typically show a positive association with tumour proliferation or tumour grade.

As used herein, where a protein is described as having a positive association with a given tumour property, e.g. proliferation or grade, this means that an increased amount of that protein (relative to a suitable standard) is indicative of that property. Similarly, where a protein is described as having a negative association with a given tumour property, e.g. high proliferation or high grade, this means that an decreased amount of that protein (relative to a suitable standard) is indicative of that property. In one embodiment, the method comprises assaying for one or more proteins selected from Table C or Table D, in particular where the source tumour is a breast cancer tumour. The proteins in Table C have been identified by the inventors as significantly linked to tumour proliferation ($p \leq 0.05$). The proteins in Table D have been identified by the inventors as significantly linked to tumour proliferation ($p < 0.01$). Therefore tests based on proteins in Table C or D are particularly useful for determining tumour proliferation properties.

In one embodiment, the method comprises assaying for one or more proteins selected from Table E or Table F, in particular where the source tumour is a breast cancer tumour. The proteins in Table E have been identified by the inventors as significantly linked to tumour grade ($p \leq 0.05$). The proteins in Table F have been identified by the inventors as significantly linked to tumour grade ($p < 0.01$). Therefore tests based on proteins in Table E or F are particularly useful for determining tumour proliferation properties.

In Tables C-F, proteins having a positive association with high proliferation (Tables C & D) or high grade (Tables E & F) are denoted by a (+). Proteins having a negative association with high proliferation (Tables C & D) or high grade (Tables E & F) are denoted by a (−).

The one or more proteins may be selected from the scaffold proteins listed in Table G. These proteins have been identified by the inventors as interacting in pathways or modules with genes expressed in cancer cells cultured in the scaffold. The proteins are believed to be important in influencing expression of genes in the cells, as listed in the Table. The inventors believe that the scaffold proteins influence expression of the genes in tumour cells in vivo, and that this helps to mediate changes in the tumour cells that are associated with tumour progression. The one or more proteins may be selected from any one of Module 1, Module 2, Module 3, or "Highly Central" in Table G or any combination of these. In one embodiment the one or more proteins is selected from the "Highly Central" list of scaffold proteins in Table G. These are believed to be key regulatory proteins, involved in initiating and mediating the changes in cells associated with tumour progession, in particular, cancer stem cell and EMT functions. The method of the fifth aspect may comprise assaying the scaffold for one or more proteins selected from one or more of Tables B-G. It will be appreciated therefore that the one or more proteins may be selected from more than one of the Tables, and/or that more than one protein may be assayed.

The method of the fifth aspect may additionally comprise assaying the scaffold for one or more of the proteins in Table H. The inventors have identified the proteins listed in Table H in cell-free scaffolds obtained from breast cancer tumours.

In a further aspect related to the fifth aspect, the present invention also provides a method for determining one or more tumour properties in a subject with a tumour, the method comprising:

assaying a sample comprising scaffold obtained from the tumour for one or more proteins selected from Table H; and determining one or more tumour properties in the subject based on the results of the assay.

Unless otherwise specified or incompatible, terms, methods and uses described in connection with the methods of the fifth aspect are also applicable to this further aspect.

Tables of Genes and Proteins

Genes and proteins herein are identified in a number of Tables. For clarification, the genes and proteins are also denoted in the Tables by Accession Numbers.

The genes and proteins are exemplified for a human subject. It will be appreciated that, where the present methods are carried out for a non-human subject, the corresponding non-human gene or protein will be investigated.

Assaying

In the method of the first aspect, the term "assaying" refers to determining the presence of target molecules representative of expression of one or more genes.

The determination may comprise a simple assessment of the presence or absence of the target molecule or may include a determination of the quantity of the target molecule present.

A suitable method by which such assaying may be carried out is selected based on type of target molecule selected.

For example, gene expression can be measured directly by techniques that allow the detection and quantification of RNA target molecules, such as RT-PCR, real-time PCR (qPCR), Northern blot, RNA sequencing (RNA-seq) and RNA microarray.

In another example, gene expression can be measured indirectly, by techniques that allow the detection and quantification of protein target molecules, such as ELISA, radioimmunoassay, immunoprecipitation, Western blot and mass spectrometry. Other suitable techniques for assaying proteins may be known to the person skilled in the art.

In a suitable embodiment an assay may allow multiple sets of target molecules to be assayed within a single reaction. An assay meeting such requirements may be referred to as a multiplex assay. Suitably a multiplex assay may allow all requisite target molecules to be assayed within a single reaction mixture (a "single tube" multiplex assay). Single tube multiplex assays may be particularly suitable for assaying mRNA transcript target molecules within a sample.

Other methods suitable for assaying gene expression will be known to the person skilled in the art.

Suitably, gene expression data obtained in the assay is compared with a suitable standard or reference. Expression of a particular gene may be increased (up-regulated) or decreased (down-regulated) compared to the standard. In one instance, a gene may show a statistically significant increase or decrease in expression compared to the standard. The change in expression of the gene is indicative of a cellular process as described herein.

A suitable standard may be, for example, gene expression in control cells, e.g. a control cell line, (typically the same cells or cell line as the cancer cells cultured in the cell-free scaffold) cultured under standard 2-D conditions. A number of controls may be used and a suitable data set constructed in order to provide a suitable standard or standards.

Another example of a suitable standard may be an expression data set for the gene, obtained using scaffolds derived from a range of source tumours, typically tumours of the same tissue type or cancer type as the source tumour in the test assay.

As described herein, expression may be determined for more than one gene in the present methods, for example, for markers of more than one cellular process, and these may each be assessed as above. In this way, a picture of a tumour, and of its properties, may be constructed.

In the method of the fifth aspect, the term "assaying" refers to determining the presence of one or more of the selected proteins in the scaffold. The determination may comprise a simple assessment of the presence of absence of the protein or may include a determination of the quantity of the protein present. Suitably the determination comprises a determination of the quantity of the protein present.

Typically, assays are carried out on a suitable sample prepared from the scaffold. This may be, for example, a sample of fixed tumour material. Assays may be carried out on a sample of intact tumour.

Proteins may be assayed in the sample using any suitable technique that allows detection and/or quantification of protein molecules. Examples include immunohistochemistry, ELISA, radioimmunoassay, immunoprecipitation, Western blot protein ligation assays and mass spectrometry. Suitable, mass spectrometry may be used. Quantification of the amount of protein may be achieved by using suitable standards, e.g. a reference cell line having a specific amount of the protein, or known amount of purified protein. Other suitable techniques for assaying proteins may be known to the person skilled in the art.

The amount of protein in the test scaffold sample may be compared with a suitable database derived from clinically characterised scaffold samples.

Treatment

The determinative methods of the first and fifth aspects are also useful in selecting tumour treatments, monitoring tumour treatments and in treating tumours. Tumour treatment can vary depending on the grade of the tumour. A progressive tumour with, for example, high grade and invasiveness (or a tumour which is likely to develop into such a progressive tumour) will typically require more aggressive treatment. Therefore assessment of tumour properties according to the present methods can be used to select appropriate treatment. Similarly, application of the determinative assays of the first and fifth aspects during and/or after treatment can be used to monitor the efficacy of treatment.

Cancer Treatments

As used herein, "treat", "treating" or "treatment" refer to provision of a clinical improvement in the subject as regards the tumourous condition. Typically, this refers to a clinical improvement of cancer in a subject with a cancerous tumour. A clinical improvement may be demonstrated by an improvement of the pathology and/or symptoms associated with the cancer.

Clinical improvement of the pathology may be demonstrated by one or more of the following: increased time to regrowth of cancer upon stopping of treatment, lack of regrowth of cancer upon stopping treatment, decreased tumour invasiveness, reduction of metastasis, increased cancer cell differentiation, or increased survival rate. Effective treatment may be demonstrated by the establishment, and optionally maintenance, of at least one of these indications.

A clinical improvement may be demonstrated by one or more anti-tumour effects. Non-limiting examples of anti-tumour effects include inhibition of tumour growth, delay in tumour growth, reduced speed of tumour growth, or a partial or complete reduction in tumour mass.

Clinical improvement of symptoms associated with cancer may be, but are not limited to partial or complete alleviation of pain and/or swelling, increased appetite, reduced weight loss and reduced fatigue.

It will be appreciated that a clinical improvement may also be determined as an improvement in tumour properties as assessed using the methods herein.

Treatments for cancerous tumours, are known to the skilled person, and include, for example, chemotherapy, endocrine therapy, radiotherapy, immunotherapy or surgical options.

Treatments may vary according to the tissue that the tumour occurs in, and according to the grade of the tumour. More aggressive tumours will typically require more aggressive treatment, for example, more aggressive drugs, higher doses of drugs or radiation, or surgical intervention.

Non-limiting examples of therapies for breast cancer are listed in the Table below, together with approximate treatment concentration ranges for human breast cancer.

| | Treatment name | Treatment concentration for human |
|---|---|---|
| Chemotherapy | Epirubicin (Anthracyclin) | 60-90 mg/m$^2$ |
| | Cyclophosphamide | 500-600 mg/m$^2$ |
| | 5-FU (5-fluorouracil) | 500-600 mg/m$^2$ |
| | Paclitaxel (Taxanes) | 70-90 mg/m$^2$ |
| | Eribulin | — |
| | Vinorelbin | — |
| | Methotrexate | — |
| Endocrine therapy | Tamoxifen | 20 mg/day |
| | Fulvestrant | 500 mg/month |
| Other therapies | Trastuzumab | — |
| | Pertuzumab | — |
| | Lapatinib (HER2) | — |
| | Everolimus (mTOR) | — |

Selecting, Providing and Monitoring Treatment

As described herein, the determinative methods of the first and fifth aspects are useful in determining a suitable treatment for a subject with a tumour. Once tumour properties have been determined, a treatment may be selected which is appropriate to those particular properties of the tumour. For example, a high grade, invasive tumour (or a tumour which is likely to develop into a high grade invasive tumour) will typically require a more aggressive form of treatment.

In second and sixth aspects, the invention provides a method for determining a suitable treatment for a subject with a tumour, comprising determining tumour properties in the subject by a method according to the first or fifth aspect, and determining a suitable treatment based on the tumour properties.

The determinative methods of the first and fifth aspects are also useful for determining or monitoring efficacy of treatment in a subject with a tumour. Typically, this is done by performing the assays of the determinative methods before and after treatment, and comparing the assay results.

Thus in a third aspect, the invention provides a method for determining or monitoring efficacy of treatment for a subject with a tumour, the method comprising:

(a):
   seeding a cell-free scaffold, obtained from the tumour before the treatment has been provided to the subject, with cancer cells;
   culturing the cancer cells in the scaffold; and
   assaying the cultured cancer cells for the presence of target molecules indicative of the expression of one or more genes in the cells;

(b):
   seeding a cell-free scaffold, obtained from the tumour after the treatment has been provided to the subject, with cancer cells;
   culturing the cancer cells in the scaffold;
   assaying the cultured cancer cells for the presence of target molecules indicative of the expression of one or more genes in the cells;
   and (c) comparing the results of the assays in (a) and (b).

In one embodiment the one or more genes may be one or more markers of tumour progression. In one embodiment the one or more genes may be selected from Table G.

Step (c) may comprise comparing the expression of one or more genes determined in step (a) with the expression of one or more genes determined in step (b).

In one embodiment, at least one of the one or more genes in steps (a) and (b) may be the same in each step. Thus the method may comprise comparing the expression of the same particular gene before and after treatment.

In one embodiment, at least one of the genes in step (a) and at least one of the genes in step (b) are markers of the same cellular process or change. For example, each may be markers of proliferation, or markers of differentiation, or markers of stem cells (pluripotency), in particular cancer stem cells, or markers of the epithelial-mesenchymal transition (EMT).

The target molecules which are assayed in steps (a) and (b) may be the same type of target molecule or may be different.

It will be appreciated that description provided herein in connection with the method of the first aspect, will also be applicable to the method of the third aspect. Thus, for example, description of genes in connection with the first aspect are also applicable.

In a seventh aspect, the invention provides a method for determining or monitoring efficacy of treatment for subject with a tumour, the method comprising:

(a) assaying a scaffold, obtained from the tumour before the treatment of the subject, for one or more proteins selected from Tables B-G;
(b) assaying a scaffold, obtained from the tumour after the treatment of the subject, for one or more proteins selected from Tables B-G; and
(c) comparing the results of the assay carried out before the treatment with the results of the assay carried out after the treatment.

Step (c) may comprise comparing the presence or amount of one or more proteins determined in step (a) with the presence or amount of one or more proteins determined in step (b).

It will be appreciated that description provided herein in connection with the method of the fifth aspect, will also be applicable to the method of the seventh aspect. Thus, for example, description of proteins in connection with the fifth aspect are also applicable.

In the methods of the third and seventh aspects, steps (a) and (b) may additionally comprise determining one or more tumour properties based on the assay results. In that case, the method for determining or monitoring efficacy of treatment may comprise comparing one or more tumour properties before and after treatment.

It will be appreciated that the treatment which is being assessed may be a complete course of treatment, or a partial treatment or a particular stage of treatment. Thus, in one embodiment, step (a) may be carried out before any treatment has been provided to the subject, and step (b) may be carried out after completion of a course of treatment. In another embodiment, step (a) may be carried out before any treatment has been provided to the subject, and step (b) may be carried out after a partial treatment, or after a particular stage of treatment. In another embodiment, step (a) may be carried out during treatment, and step (b) may be carried out at a later stage of treatment. Step (a) and/or step (b) may be repeated as treatment progresses. In this way, the method can be used to provide an ongoing assessment of treatment.

Efficacy of treatment will be shown by a detectable improvement in one or more tumour properties after treatment. This may be determined by a change in marker gene expression which is indicative of such an improvement. An improvement in tumour properties generally refers to a reduction in one or more properties associated with progression, such as any of those described herein. For example, an improvement may be a reduction in invasiveness, migration, malignancy grade, malignancy potential recurrence, resistance to treatment and/or proliferation.

Providing Treatment and Medical Uses

In some instances, the methods of the first and fifth aspects include an additional step of selecting a suitable treatment and/or providing a suitable treatment to the subject. The treatment will be selected according to the tumour properties determined.

Thus, in an eighth aspect, the invention also provides a method for treating a subject with a tumour, in a ninth aspect, the invention provides a cancer treatment for use in treating a subject with a tumour, and in a tenth aspect, the invention provides a method of treating subject with a tumour.

Providing

The term "providing" as used herein encompasses any techniques by which the subject receives a particular therapy. Suitable techniques for administering cancer therapies are known to the skilled person.

Predicting Likely Efficacy of Treatment

A method according to the first aspect may also be used to assess the likely efficacy of a particular treatment in a subject with a tumour. By applying the treatment to the cell-free scaffold comprising the cultured cells, and assessing the effect on the outcome of the determinative assay, it is possible to predict the likely efficacy of the treatment in the source tumour.

Thus, in a fourth aspect, the invention provides a method for determining likely efficacy of a treatment for subject with a tumour, the method comprising:

(a)
   seeding a cell-free scaffold obtained from the tumour with cancer cells;
   culturing the cancer cells in the scaffold;
   assaying the cultured cancer cells for the presence of target molecules indicative of the expression of one or more genes in the cells;

(b) applying the treatment to the scaffold comprising the cancer cells;

(c) assaying the cultured cancer cells after the treatment has been applied, for the presence of target molecules indicative of the expression of one or more genes in the cells;
and (d) comparing the results of the assays in (a) and (c).

In one embodiment the one or more genes may be one or more markers of tumour progression. In one embodiment the one or more genes may be selected from Table G.

Step (d) may comprise comparing the expression of one or more genes determined in step (a) with the expression of one or more genes determined in step (c).

In one embodiment, at least one of the one or more genes in steps (a) and (c) may be the same in each step. Thus the method may comprise comparing the expression of the same particular gene before and after treatment.

In one embodiment, at least one of the genes in step (a) and at least one of the genes in step (c) are markers of the same cellular change or process. For example, each may be markers of proliferation, or markers of differentiation, or markers of stem cells (pluripotency), in particular cancer stem cells, or markers of the epithelial-mesenchymal transition (EMT).

The target molecules which are assayed in steps (a) and (c) may be the same type of target molecule or may be different.

Steps (a) and (c) may additionally comprise diagnosing or prognosing one or more tumour properties based on the assay results. In that case, the method for determining likely efficacy of treatment may comprise comparing one or more tumour properties before and after treatment.

Efficacy of treatment will be shown by a detectable improvement in one or more tumour properties after treatment. This may be determined by a change in marker gene expression which is indicative of such an improvement.

It will be appreciated that description provided herein in connection with the method of the first aspect, will also be applicable to the method of the fourth aspect. Thus, for example, description of genes in connection with the first aspect are also applicable.

Other Terms

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps. However, it will be appreciated that the words "comprise" and "contain" encompass within their meaning, the terms "consisting of" and "consisting essentially of".

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

All publications, patents and patent applications mentioned in this specification are herein incorporated by reference in to the specification to the same extent as if each individual publication, patent or patent application was specifically and individually indicated to be incorporated herein by reference.

Unless stated otherwise, the contents of any Internet sites referenced herein are incorporated herein by reference as of 3 November 2016.

Any references to "detectable" or "detected" are as within the limits of detection of the given assay or detection method.

EXAMPLES

The invention will now be described by way of specific Examples and with reference to the accompanying Figures, which are provided for illustrative purposes only and are not to be construed as limiting upon the teachings herein.

Materials and Methods

Decellularization Procedure

Breast cancer samples were collected directly after surgery or from a frozen biobank via the clinical pathology diagnostic unit at Sahlgrenska University Hospital. A piece of the tumor containing area, approximately 3×3×2 mm, was sectioned from the sample. The sample sizes varied depending on the available tumour material but the maximum thickness of the scaffolds used for the process did not exceed 3 mm. Tumour pieces then underwent repetitive washes consisting of incubation in 0.1% SDS+0.02% Na-Azide (VWR-786-299)+5 mM $2H_2O$—Naz-EDTA (Sigma-ED2SS) and 0.4 mM PMSF (Sigma-93482) for 6 hours followed by rinses in destilled water including (0.02% Na-Azide and 5 mM $2H_2O$—$Na_2$-EDTA and 0.4 mM PMSF) for 15 min (1). After each decelluralization cycle a small piece of tissue was screened for the presence of nuclei using standard histological procedures and if nuclei were still present, the wash cycle was repeated. The number of washes needed varied from 1-4 (mean 1,9). Two wash cycles were sufficient for more than 80% of the samples. After successful decellularization, the specimens were washed for 72 hrs in distilled water exchanged every 12 hour to remove cell debris followed by a 24 hour wash in PBS (Medicago 09-9400-100). All wash steps were performed at 37° C. on an agitator with gentle shaking (175 RPM). Sterilization was performed by incubation in 0.1% peracetic acid (Sigma Aldrich 433241) in destilled water for 1 hour in room temperature followed by a wash in PBS containing 1% Antibiotic-Antimycotic (Gibco 15240096) for 24 hours 37° C. (175 RPM). Scaffolds were then stored up to 1 month in PBS containing 0.02% Na-Azide and 5 mM $2H_2O$—$Na_2$-

EDTA in +4° C. Before recellularization, scaffolds were washed in PBS containing 1% Antibiotic-Antimycotic for 24 hours, 37° C. or soaked in complete media for 1 h to remove storage buffer.

Recellularization with Breast Cancer Cells

Different methods to recellularize scaffolds were tested including variations in cell amounts, culture conditions and application of cells. The optimal method to obtain successful recullarization was to use 3×3 mm scaffolds with a maximum depth of 2 mm and adding $3 \times 10^5$ cells to a 48-well plate containing 0.5 ml cell line specific media with 1% Antibiotic-Antimycotic. The day after seeding cells, scaffolds were transferred to a new well and visually checked every fourth day. If cells were growing outside the scaffold area the scaffold was transferred to a new well. Optimal growth time for the scaffolds was 2-3 weeks.

FACS

Individual cells were collected by FACS in a 96-well plate and subjected to direct cell lysis in RNase free water with BSA (Thermo Scientific B14) 1 mg/ml, and immediately frozen on dry ice. To each 96-well plate, 100 cells were sorted to two wells (positive control) and two wells were empty (negative control).

Harvest and Extraction of RNA

Recellularized scaffolds were washed twice in PBS before lysed in lysis buffer (RNase free water with BSA (Thermo Scientific B14) 1 mg/ml). RNA Spike II (TATAA RS10SII) 5 ul/100 ul and RnaseOUT (Invitrogen 10777-019) 4 U/ul was also added in the lysis step in material derived from the biobank. Control cells grown in monolayer was either washed with PBS and frozen immediately on dry ice or scraped off the plastic surface and harvested using lysis buffer or QIAzol. RNA was then extracted or samples were placed on dry ice and stored in −80° C.

To retrieve RNA, samples were thawed on ice and homogenized using a stainless steel bead (Qiagen 69989) in TissueLyzer II (Qiagen) for 2×5 min, 25 Hrz. To the frozen tumour pieces QIAzol and a steel bead was added prior to homogenization. Samples were visually checked and if not shattered, homogenization was repeated for another 5 minutes.

Samples were centrifuged 4° C. 1min at 10000rpm and used for cDNA synthesis or RNA was further purified by phenol chloroform extraction, miRNeasy Mini Kit (Qiagen 217084) and DNased by Rnase-Free Dnase Set (Qiagen 79254). RNA concentration was measured by NanoDrop and samples for QuantSeq sequencing was quality tested on Bioanalyzer.

Reverse Transcription cDNA synthesis from RNA was carried out using GrandScript cDNA synthesis kit (TATAA Biocenter). Reverse transcription was performed in 10-20 µl reaction mixes and was performed at 22-25° C. for 5 min, 42° C. for 30 min and terminated by heating to 85° C. for 5min followed by cooling down to 4° C. All samples were diluted 4× with water before further processing.

Preamplification

For single cell analysis preamplification was performed on cDNA (corresponding to half a cell) with SYBR GrandMaster Mix (TATAA Biocenter) using a primer pool of 96 primer pairs. Preamplification was performed in 40 µl containing SYBR GrandMaster Mix (1×), primers (40 nM, each primer) and BSA (1 µg/µl). Preamplification was performed at 95° C. for 3min followed by 20 cycles of amplification (95° C. for 20 sec, 60° C. for 3 min and 72° C. for 20 sec) and a final incubation at 72° C. for 10 min. All preamplified samples were chilled on ice and diluted 1:20 in TE-buffer, pH 8.0 (Ambion).

qPCR

All qPCR primers were designed using Primer3 (http://frodo.wi.mit.edu/primer3/input.htm), Primer-BLAST (http://www.ncbi.nlm.nih.gov/tools/primer-blast/) or Netprimer (Premier) and synthesized by Sigma-Aldrich. Primers were controlled for specificity using BLAST (NCBI). Primer pairs were tested in qPCR runs for their specificity and PCR product sizes were confirmed by gel electrophoresis.

qPCR was performed on 2 µl diluted, preamplified cDNA or non-preamplified cDNA using SYBR GrandMaster Mix (TATAA). qPCR was performed in 6 µl containing SYBR GrandMaster Mix (1×) and primers (400 nM, each primer) in 384-well plates (FrameStar 480, 4titude) on a CFX384 Touch Real-Time PCR Detection System (Bio-Rad). qPCR samples were heated to 95° C. for 2 min and amplified for 35-50 cycles at 95° C. for 5 s, 60° C. for 20 s, and 70° C. for 20 s followed by a melting curve analysis performed from 65° C. to 95° C. with 0.5° C. per 5 s increments.

Data Analysis

Cq values were determined by the second derivative maximum method using the CFX Manager Software version 3.1 (Bio-Rad). Data pre-processing were performed with GenEx (MultiD) as described (2). Briefly, samples with aberrant melting curves were removed. For single cell analysis, an inter-plate calibrator (IPC) sample was included in the qPCR used for normalization. Cycle of quantification values larger than 28 were replaced with 28. Data were transformed to relative quantities assuming that a cycle of quantification value of 28 was equal to one molecule. Missing data were replaced with 0.5 molecules. For bulk-qPCR samples values were normalized using 2D control samples and cycle of quantification values larger than 35 were replaced with 35. Data were transformed to relative quantities assuming that a cycle of quantification value of 35 was equal to one molecule. Missing data were replaced with 36 molecules.

Whole-mRNA Reverse Transcription and Pre-Amplification

RNA from cells grown in monolayer, scaffolds or xenografts was diluted in a buffer containing 5 µl, 1 µg/µl BSA, 2.5% glycerol (Fisher Scientific) and 0.2% Triton X-100 (Sigma-Aldrich-Aldrich) in DNase/RNase-free water (Life Technologies) to reach a final amount of 10 ng total RNA in 5 µl sample volume. Samples were processed according to a recently published Smart-Seq2 protocol (3) with minor changes (NB: final concentrations of the hybridization and reverse transcription (RT) protocol are given in brackets and refer to RT reaction volume). In short, adapter-ligated oligo-dT (1 µM, 5'-AAGCAGTGGTATCAACGCAGAGTACT$_{30}$VN-3', with V=A, C or G and N=A, C, G, or T, Sigma-Aldrich) were hybridized to mRNA in the presence of dNTP (1 mM, Sigma-Aldrich) and ERCC spike-in controls (3)(corresponding to 1 µl of 1:5000 diluted stock solution; Life Technologies) at 72° C. for 3 min. RT was performed in 15 µl containing SuperScript II first-strand buffer (1×; 50 mM Tris-HCl, pH 8.3, 75 mM KCl, and 3 mM MgCl$_2$, Invitrogen), betaine (1 M, Sigma-Aldrich), DTT (5 mM), additional MgCl$_2$ (10 mM, both Life Technologies), template switching oligo (TSO; 5'-AAGCAGTGGTAT-CAACGCAGAGTACATrGrG+G-3' with rG=riboguanosine and +G=locked nucleic acid modified guanosine; 0.6 µM, Eurogentec), RNaseOUT (15 U, Invitrogen), and SuperScript II enzyme (150 U, Invitrogen) at 42° C. for 90 min and 70° C. for 15 min before being chilled to 4° C. Aliquots of non-amplified cDNA samples were stored at −20° C. until further use.

Preamplification of 7.5 µl cDNA was performed in 50 µl containing KAPA Hifi HotStart Ready Mix (1×; KAPA Biosystems) and IS PCR primer (60 nM, 5'-AAGCAGTGGTATCAACGCAGAGT-3', Sigma-Aldrich) as follows: denaturation at 98° C. for 3 min followed by 24 cycles of incubation at 98° C. for 20 s, 67° C. for 15 s, and 72° C. for 6 min, and a final incubation at 72° C. for 5 min before being chilled to 4° C.

Aliquots of 1 µl purified samples were forwarded to capillary gel electrophoresis using the High Sensitivity DNA Kit (Agilent) on a 2100 Bioanalyzer (Agilent) to assess their concentration and product length distribution.

Preparing Indexed RNA-Sequencing Libraries

RNA-sequencing libraries were generated using the Nextera XT DNA Sample Preparation and Index kits (Illumina) according to the manufacturer's recommendations with minor changes. In short, 0.1 ng of preamplified cDNA were tagmented in a volume of 20 µl containing 10 µl TD buffer and 5 µl ATM at 55° C. for 5 min. Tagmentation was stopped by addition of 5 µl of NT buffer and incubation at room temperature for another 5 min (all solutions supplied in the Nextera XT DNA Sample Preparation Kit). For introducing indexing sequences, 15 µl NMP PCR master mix solution (Nextera XT DNA Sample Preparation Kit) and 5 µl of i5 and i7 index primers, each, (Nextera XT v2 Index Kit) were added to tagmented samples and subjected to amplification. Therefore, samples were heated to 72° C. for 3 min, denaturated at 95° C. for 30 s and amplified for 16 cycles at 95° C. for 10 s, 55° C. for 30 s, and 72° C. for 30 s, followed by a final extension step at 72° C. for another 5 min before being chilled to 10° C. Samples were purified using the AMPure XP beads kit (Agencourt, Beckman Coulter) as recommended by the manufacturer with minor changes. In short, tagmented and indexed cDNA was bound to beads (sample:beads volume ratio of 0.6) at room temperature for 5 min and separated from supernatant on a magnetic stand (DynaMag 96 Side, Life Technologies) for another 5 min. Supernatants were removed and captured cDNA-charged beads were rinsed twice with 200 µl 80% ethanol for 30 s before being air dried for approximately 2 min. Purified cDNA was recovered from beads in DNase/RNase-free water yielding 15 µl eluate and stored at −20° C. until further use.

Mean fragment length (High Sensitivity DNA Kit) and concentration (dsDNA High Sensitivity Assay Kit, Qubit, Life Technology) of indexed single-cell libraries were assessed. Single-cell libraries diluted to 15 nM and pooled. Quality and concentration of the final pool was assessed as above and it was diluted to 10 nM before being forwarded to sequencing.

RNA Sequencing

Sample pool was forwarded to paired-end sequencing on a high-throughput sequencer (NextSeq 500, Illumine).

Accompanying Quality Controls and Measurements

Quality control singleplex qPCR on cDNA using RPS10 was performed where 1 µl undiluted, non-preamplified cDNA were run in 10 µl containing 1× TATAA SYBR GrandMaster Mix and 400 nM of each primer in 384-well plates (FrameStar 480, 4titude) on a CFX384 Touch Real-Time PCR Detection System (Bio-Rad). qPCR samples were heated to 95° C. for 2 min and amplified for 50 cycles at 95° C. for 5 s, 60° C. for 20 s, and 70° C. for 20 s followed by a melting curve analysis performed from 65° C. to 95° C. with 0.5° C. per 5 s increments. Cq values were determined by the second derivative maximum method using the CFX Manager Software version 3.1 (Bio-Rad). Additionally, a similar qPCR analysis was performed on preamplified samples to make sure there was no inconsistency in the preamplification reaction.

Alignment and Gene Level Expression Estimation

Reads were aligned to the hg19 reference of the human genome, with ERCC spike-in sequences appended, using the STAR (5) read mapper with splice junctions supplied from the GENCODE (6) V17 annotation. To obtain expression estimates, reads were binned to genes using HTseq (7), with the options "-s no" and "-m intersection-strict". Read counts thus derived were then normalized using sample library size to obtain RPM values.

Principal Component Analysis

A principal component analysis was performed using MATLAB function pca or GenEx (Multid). The analysis was performed on zscore transformed expression values as standardized $\log_2(\text{RPM}+1)$.

Differential Expression Analysis

Differential expression analysis was performed in R using the DESeq2 analysis method (7). Samples from the two cell lines MCF7 and MDA-MB-231 were analyzed separately and within each cell line samples were grouped as 2D, scaffold or xenograft. A pre-filtering step was performed removing genes with a sum of reads of zero or one. Differentially expressed genes were defined pair-wise between all conditions using a cutoff of padj of 0.05. Up-regulated and down-regulated genes were further defined using a cutoff of log 2(fold change) of 1 and −1, respectively.

Gene Set Enrichment Analysis

The differentially expressed genes were further analysed using gene set enrichment analysis where the Reactome gene set was used to find pathways connected to the different gene lists.

Xenografts

Cell lines MDA-231, MCF7 and T47D were grown on scaffolds and in 2D cultures. Accutase (Sigma Aldrich A6964) was used for dissociation into single cell suspensions. Cells were counted manually and suspended in DMEM mixed 1:1 with GF reduced Matrigel (BD Biosciences) prior to injections subcutaneously in the flanks of NOG mice (immunocompromised, non-obese severe combined immune deficient interleukin-2 chain receptor γ knockout mice) from Taconic, Denmark. A 17β-Estradiol pellet, 90-day release (Innovative Research of America) was implanted 2-4 days before cell injections in the mice receiving an estrogen dependent cell line. Tumors were measured using calipers twice a week and tumour volume was calculated by the formula $1/2(\text{Length} \times \text{Width}^2)$.

Western Blot

Cells were harvested in RIPA buffer containing protease inhibitors and EDTA, pipetted up and down occasionally while incubated on ice for 30 min to 1 h. Lysates were centrifuged at 8,000 XG for 15 min, 4° C. Supernatant was transferred to a new tube and used for western blot analyses. Lysates were mixed with loading buffer, reducing agents and heated to 98° C. for 5 min and then allowed to cool. Standard procedures for BioRad western blot system was used. Proteins were transferred to a Nitrocellulose membrane using wet transfer system 200 mA.

Mammosphere Assay

Mammosphere assays were carried out as described in (9)

Protein Quantification and Proteomic Analysis (TMT)

For proteomics analysis the TMT-labeled relative quantification LC-MSMS method was used. Equal amounts of proteins (30 µg samples) were homogenized and extracted from each scaffold by a lysis buffer (M urea, 4% 3-[(3-cholamidopropyl)dimethylammonio]-1-propanesulfonate (w/v), 0.2% sodium dodecyl sulfate (SDS) (w/v), 5 mM ethylenediaminetetraacetic acid). For relative quantification, the proteins were trypsinized into peptides and further labeled with tandem mass tags (TMTs) with a unique tag for each sample and the reference. The peptides were fractionated by a strong cation exchange chromatography (SCX) and the separation for the mass-to-charge (m/z) ratio of the peptides (MS) the reversed-phase nanoLC interfaced QExactive was used followed by fragmentation (MS/MS) for peptide sequence information and relative quantification to an Orbitrap Tribrid Fusion MS instrument. Stepped HCD fragmentation (TMT) was used for the QMS analysis.

For each set the MS-raw data was merged during the search for protein identification and relative quantification using Proteome Discoverer database. Due to the isobaric chemical structure of the TMT tags, the peptides labeled with different tags was indistinguishable during chromatographic separations and in MS mode. Each tag contained a characteristic so-called reporter ion with a unique structure which is detectable upon fragmentation. The ratio of these reporter ion intensities in MS3 spectra was used for quantification. Only peptides unique for the specific protein were considered for quantification.

GSEA and Related Methods

To examine functional overlap among the genes that were differentially expressed in the scaffold environment and the proteins represented in the tumor scaffolds, gene set enrichment analysis (GSEA) was performed with the GSEA online tool (http://software.broadinstitute.org/gsea/index.jsp) (Subramanian, A., Tamayo, P., Mootha, V. K., Mukherjee, S. & Ebert, B. L. Gene set enrichment analysis: A knowledge-based approach for interpreting genome-wide. *Proc Natl Acad Sci U S A* 102, 15545-15550 (2005), using Reactome pathways (Croft, D. et al. Reactome: A database of reactions, pathways and biological processes. *Nucleic Acids Res.* 39, (2011)) and a q-value cutoff of 0.05.

To investigate the protein interactions that could mediate the adaption of the MCF7 and MDA231 cells to the scaffold environment, a first order network connecting the scaffold proteins was extracted from the Human Protein Reference Database (Keshava Prasad, T. S. et al. Human Protein Reference Database—2009 update. *Nucleic Acids Res.* 37, 767-772 (2009)) using the iRefR (Mora, A. & Donaldson, I. M. iRefR: an R package to manipulate the iRefIndex consolidated protein interaction database. *BMC Bioinformatics* 12, 455 (2011)) R package. Unconnected nodes were removed to obtain the main network, encompassing 1276 proteins (nodes) and 6356 interactions (edges) in total.

Central nodes were determined by calculating the betweenness centrality (Freeman, L. C. A Set of Measures of Centrality Based on Betweenness. *Sociometry* 40, 35 (1977)) of each protein. Significance was then assessed by comparisons to an empirical null model generated by randomizing the edges of the network and successively recalculating betweenness centrality 10000 times. Nodes with q-value<0.05 (Holm correction) were called significant.

Network modules were discovered using the "Walktrap" algorithm (Pons, P. & Latapy, M. Computing communities in large networks using random walks. *Phys. Soc.* arXiv: physics/0512106 (2005). doi:10.1007/11569596). To determine if the proteins within a given module were more densely connected than could be expected by chance, a Wilcoxon test was used to compare the degree distributions of nodes included and excluded from the module. Modules with a q-value less than 0.05 (Holm correction) were called significant. To further assess the overrepresentation of functional categories among genes within modules, the "enrichPathway" function of the ReactomePA (Yu, G. & He, Q.-Y. ReactomePA: an R/Bioconductor package for reactome pathway analysis and visualization. *Mol. BioSyst.* 12, 477-479 (2015) R package was used, specifying the full set proteins in the extracted network as background. Categories with q-value<0.05 (Benjamini-Hochberg correction) were considered significant.

REFERENCES

1. Thompson A, et al. Towards the development of a bioengineered uterus: Comparison of different protocols for rat uterus decellularization. *Acta Bio Material* 12, 5034-5042, (2014).
2. Ståhlberg, A. et al. RT-qPCR work-flow for single-cell data analysis. *Methods.* 59, 80-88 (2013).
3. Picelli, S. et al. Smart-seq2 for sensitive full-length transcriptome profiling in single cells. *Nat. Methods* 10, 1096-8 (2013).
4. Jiang, L. et al. Synthetic spike-in standards for RNA-seq experiments. *Genome Res.* 21, 1543-51 (2011).
5. Dobin, A. et al. STAR: ultrafast universal RNA-seq aligner. *Bioinformatics* 29, 15-21 (2013).
6. Harrow, J. et al. GENCODE: The reference human genome annotation for the ENCODE project. *Genome Res.* 22, 1760-1774 (2012).
7. Anders, S., Pyl, P. T. & Huber, W. HTSeq A Python framework to work with high-throughput sequencing data. *bioRxiv* (2014). doi:10.1101/002824
8. Love, M. I., Huber, W. & Anders, S. Moderated estimation of fold change and dispersion for RNA-seq data with DESeq2. *Genome Biology* (2014). doi: 10.1186/s13059-014-0550-8
9. Frances, L. Shaw et aLA Detailed Mammosphere Protocol for the Quantification of Breast Stem Cell Activity. *J Mammary Gland Biol Neoplasia.* 17, 111-117 (2012)

Results

The rational for this project was to use the cell-free original breast cancer scaffolds as templates for breast cancer cells to infiltrate within thereby creating an in vivo like growth system that can be studied regarding tumor promoting features in relation to scaffold composition and clinical origin. Initially, the inventors tested a standardized decellurising protocol consisting of a prolonged mild detergent treatment potentially preserving the basic scaffold composition optimally as described in Material and Methods. The method was successfully adapted to breast cancer and scaffolds could reproducibly be produced from various breast cancer types by the prolonged detergent wash protocol (FIG. 1). Scaffolds were indeed cell free, confirmed by extensive sectioning and microscopic visualization as well as by DNA analyses (data not shown).

Figure 2:
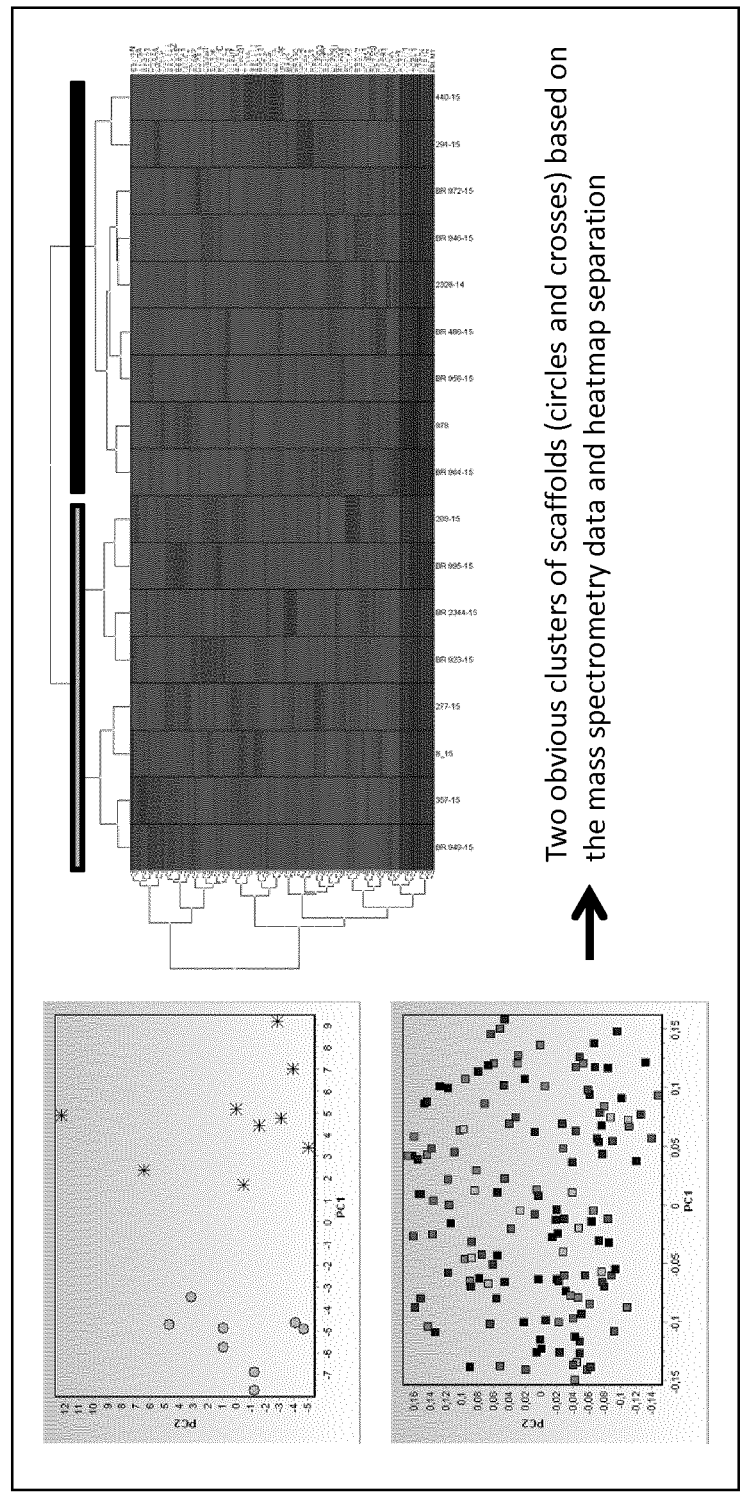
FIG. 2—Mass spectrometry analyses of 17 breast cancer tumour scaffolds and identified proteins as well as clustering illustrated by partial component analysis (PCA) and a heatmap.
Figure 3:
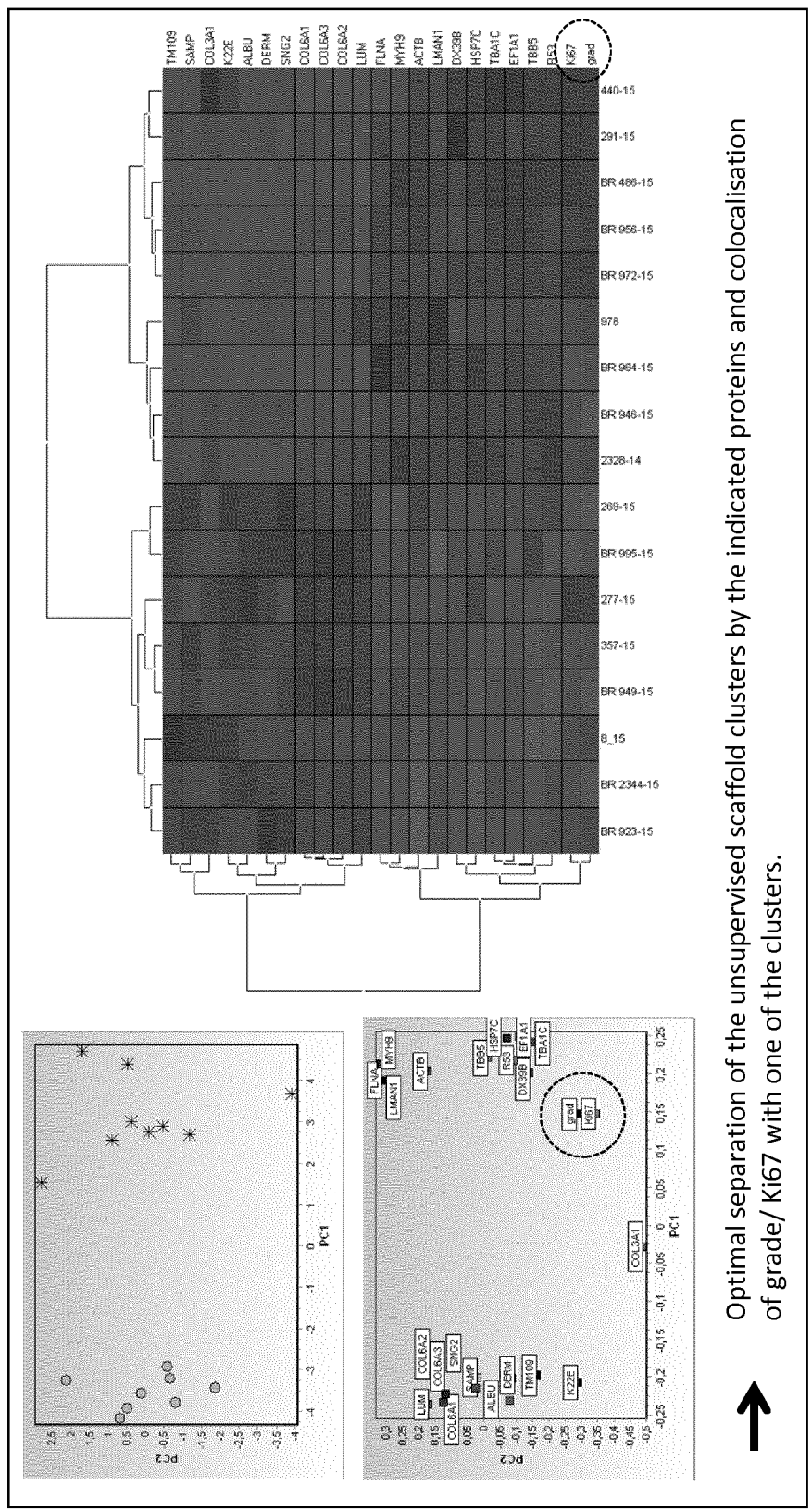
FIG. 3—Top 21 proteins identified by dynamic PCA (p-value separation) discriminating the unsupervised clusters illustrated by PCA and a heatmap. Tumour grade (grad) and proliferation (Ki67) is included in the PCA and heatmap (shown by dotted circle).
Figure 4:
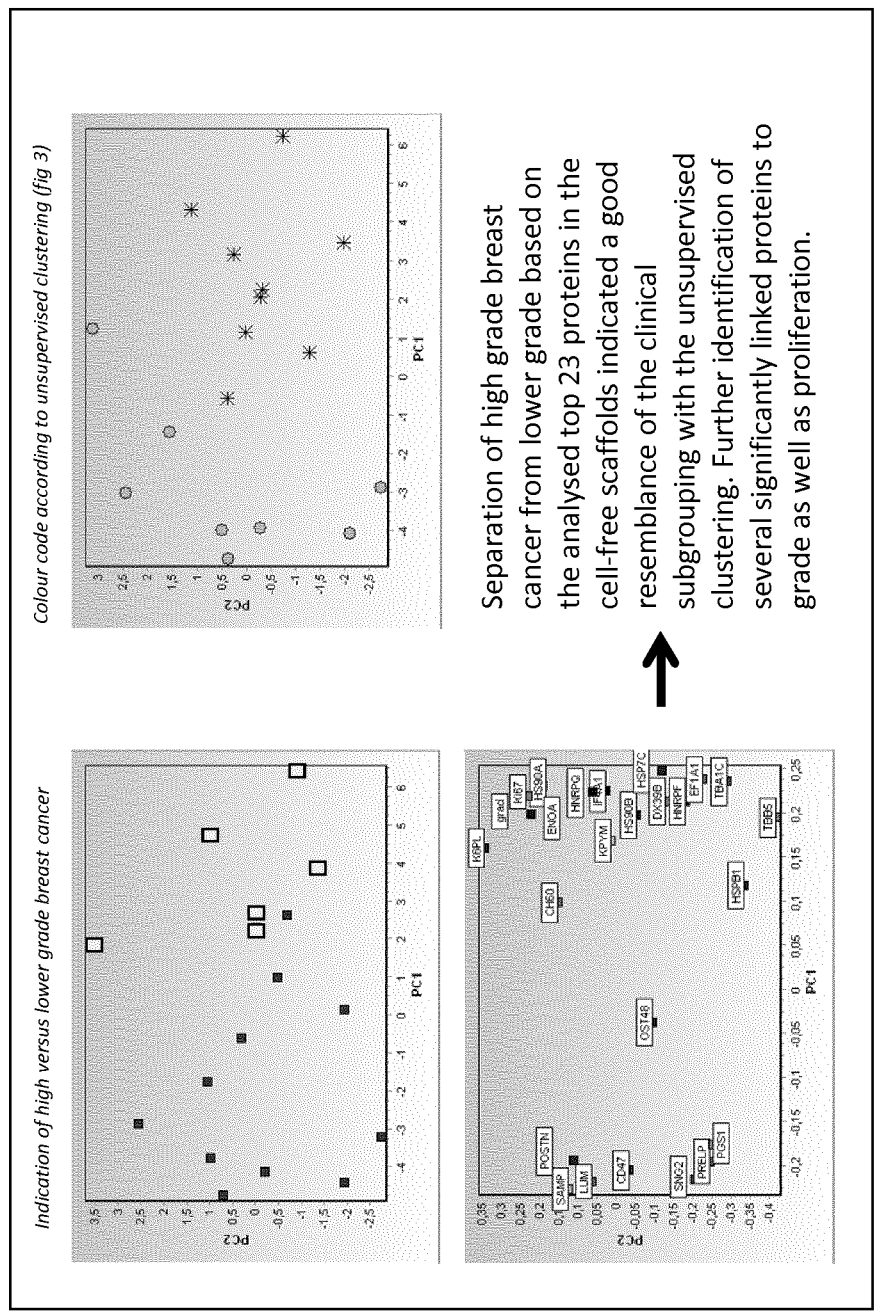
FIG. 4—Top 23 proteins identified by dynamic PCA (p-value separation) discriminating high grade breast cancer (large squares) from lower grade (small squares) and illustration by PCA. The separation of the unsupervised clusters (circles and crosses) using the identified proteins is also shown.
Figure 5:
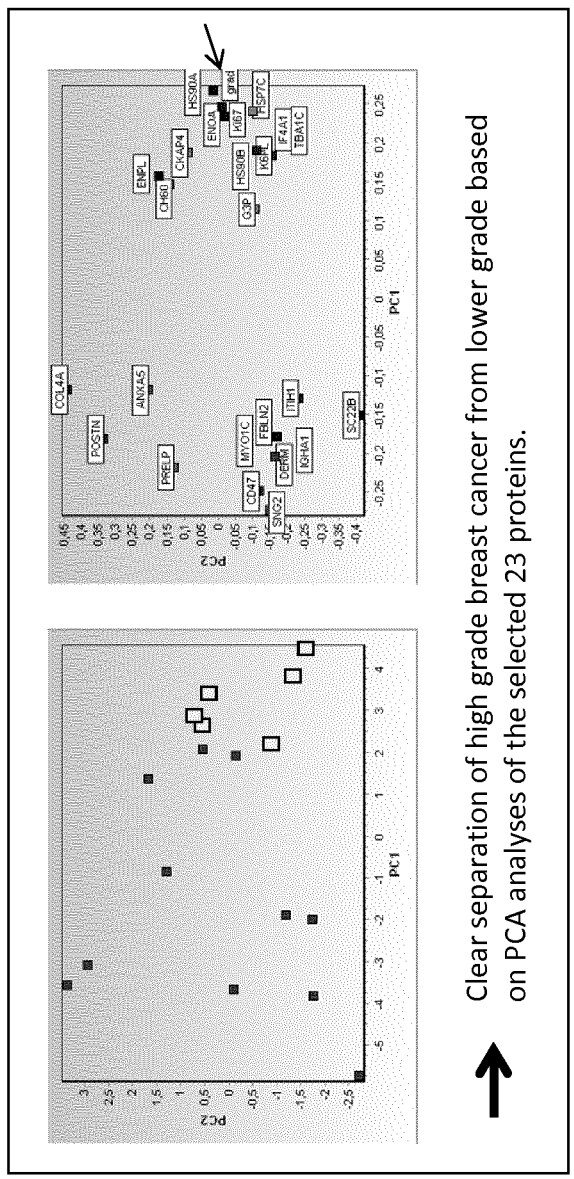
FIG. 5—PCA of the 23 proteins identified by mass spectrometry of cell-free scaffolds significantly linked to tumour grade or proliferation. High grade breast cancer (larger squares) and lower grade (smaller squares). The location of Ki67 and grade is indicated by an arrow in the loading PCA plot.

The composition of the cell free scaffolds obtained from breast cancer samples was then delineated using mass spectrometry. 17 different scaffolds were submitted for mass spectrometry analyses using the Sahlgrenska Academy core facility in Gothenburg (details in Material and Methods). Since breast cancer is a heterogeneous disease in many aspects the inventors noted major clinic-pathological parameter as grade, proliferation, ER-positivity and HERs status in order to detect any differences in composition linked to clinical subgroups. In total 145 different proteins were detected in the various scaffolds including several expected proteins as various forms of collagen and keratin but also more unexpected proteins (Table H). When using partial component analyses (PCA) of the mass spectrometry identified scaffold proteins, two distinct clusters of scaffolds was observed (FIG. 2) supporting that breast cancer can be subdivided into subgroups solely based on the composition of the cell-free scaffolds. A dynamic PCA identified the key proteins responsible for the main clustering as illustrated in FIG. 3 and FIG. 4 and includes proteins as periostin and dermatopontin as well as various forms of collagen. Tumour grade and tumor proliferation measured by Ki67 further clustered together with one of the subgroups defined by for example FLNA and TBA1C (FIG. 3) supporting that the unsupervised clustering identified a cluster that potentially was linked to tumour grade and tumour proliferation. When subdividing the scaffolds according to high tumour grade versus lower grade and performing a dynamic PCA (FIG. 4) the inventors identified several proteins that effected the separation and many of these proteins were similar to the proteins identified in the unsupervised clustering of scaffolds. The unsupervised clustering was further partly overlapping with clustering based on the proteins associated with grade and proliferation as illustrated in FIG. 4. Several proteins were significantly linked to these processes and periostin was for example inversely linked to tumour grade ($r=-0.49$) and tumour cell proliferation (Ki67, $r=-0.44$) whereas K6PL was positively associated to both grade ($r=0.70$) and Ki67 ($r=0.63$). Additional proteins were further identified by collating all proteins that were significantly linked to grade or proliferation in univariate analyses as presented in FIG. 5 clearly separating the two types of scaffolds. All key proteins linked to the two subtypes of scaffolds overlapping with clinical aggressive features as tumour grade and proliferation are listed in Tables B-F.

Figure 6:
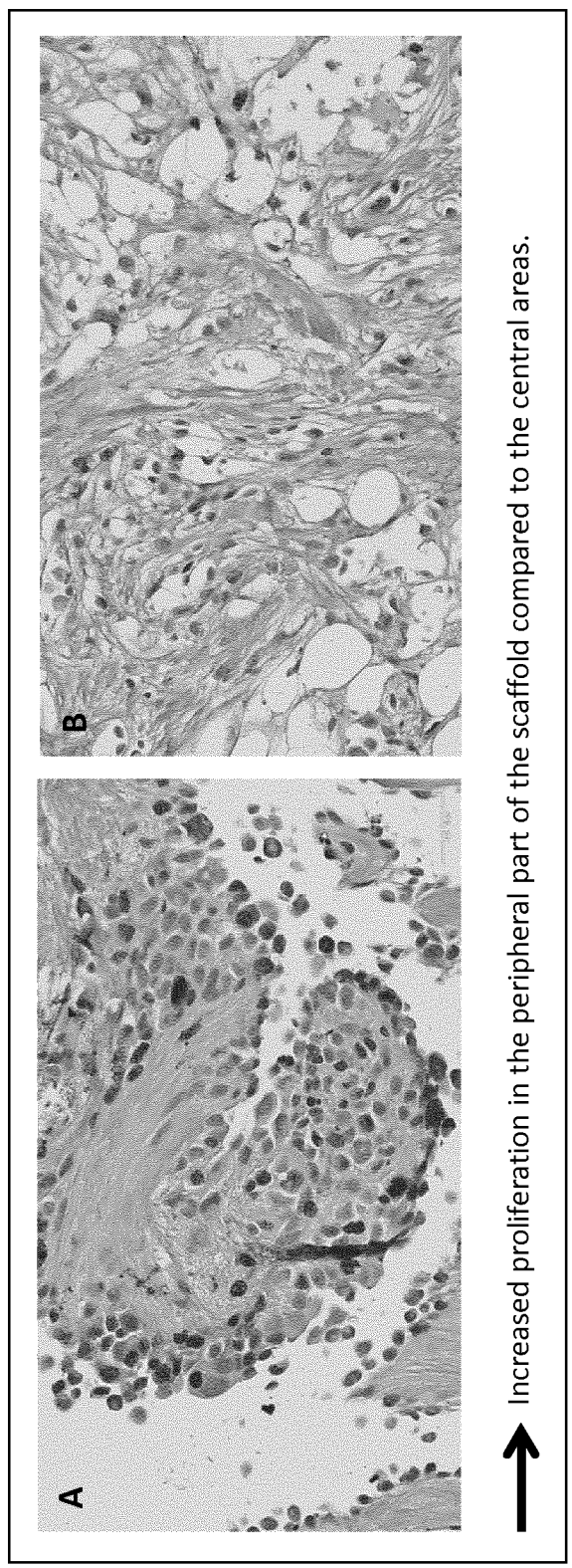
FIG. 6—. Immunohistochemical Ki67 staining of a (A) peripheral part of a scaffold culture of MDA231 cells and a (B) central part of the scaffold.

Next, the inventors tested how various breast cancer cell lines could survive and potentially infiltrate as well as colonise the scaffolds. ER-negative cell lines as the MDA-231 grew massively infiltrative in the scaffolds and created an in vivo like tumour within three weeks (FIG. 1). ER-positive breast cancer as MCF7 showed less infiltrative capacity but created nests of tumour cells within some parts of the scaffolds as well closer to the surface of the scaffolds (not shown). Cancer cells from all cell lines tested showed active proliferation and survival as well signs of various differentiation stages within the different patient scaffolds. MDA 231 cells lined up former vascular spaces with endothelial like cells and produced fibroblast like cells as well as varying more breast cancer like cells in different areas of the scaffolds (FIG. 1). Highly infiltrating cancer cells were commonly low proliferative as illustrated by Ki-67 staining on sectioned scaffolds infiltrated by MDA231 cells (FIG. 6). In summary, the inventors obtained reproducible cancer cell growth in all initially tested scaffolds (n=26) supporting the stability of the growth platform established.

Figure 7:
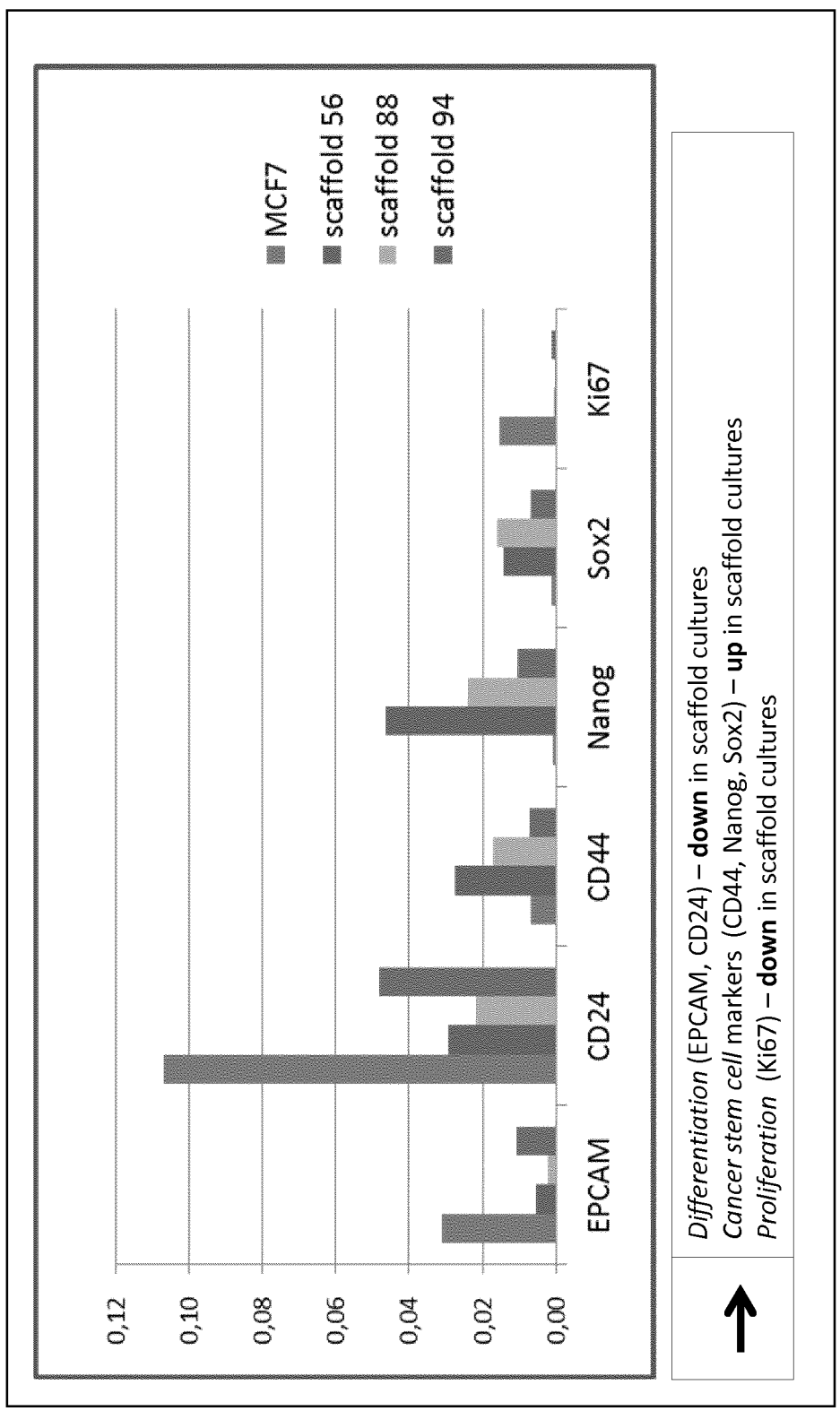
FIG. 7—Bulk qPCR of MCF7 breast cancer cells in (reading left to right): control (2D), and three weeks of scaffolds cultures (56, 88, 94).
Figure 8:
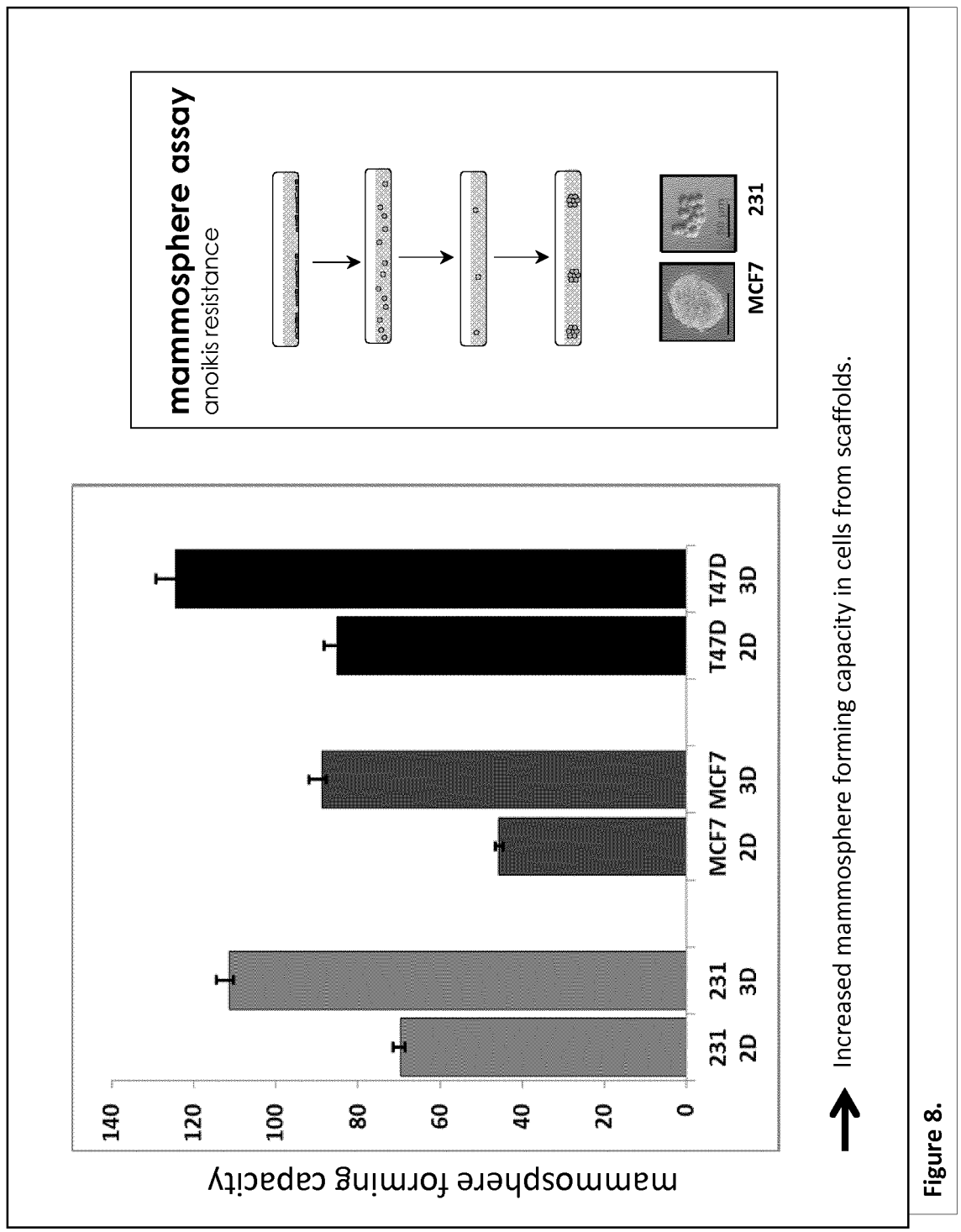
FIG. 8—Surrogate methods to assess the cancer initiating potential of different breast cancer cell lines grown under regular 2D conditions (2D) or in scaffolds (3D).
Figure 9:
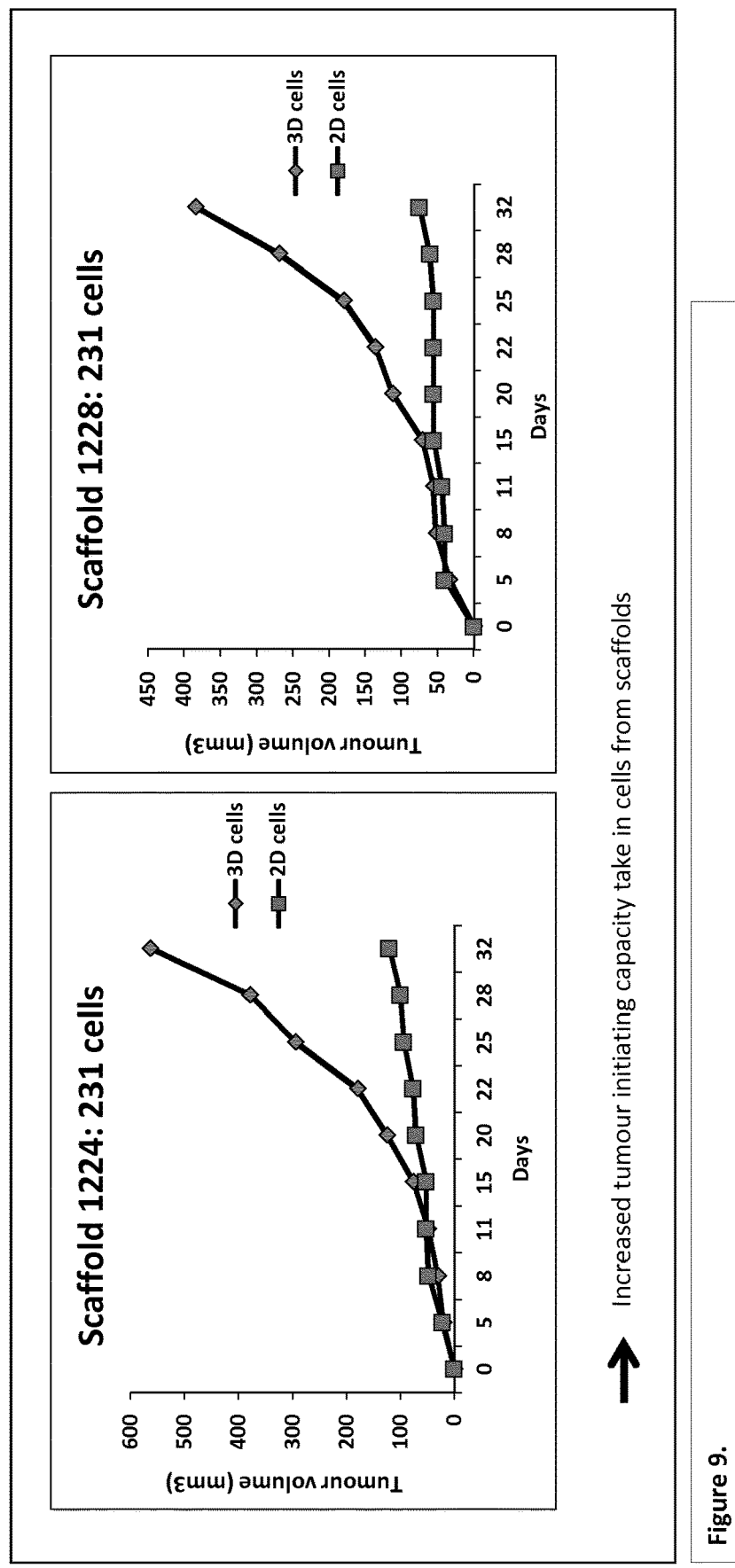
FIG. 9—Tumour take in immunocompromised mice using MDA 231 breast cancer cells (231) grown under regular 2D conditions (2D) or in two different scaffolds, 1224 and 1228 (3D).
Figure 10:
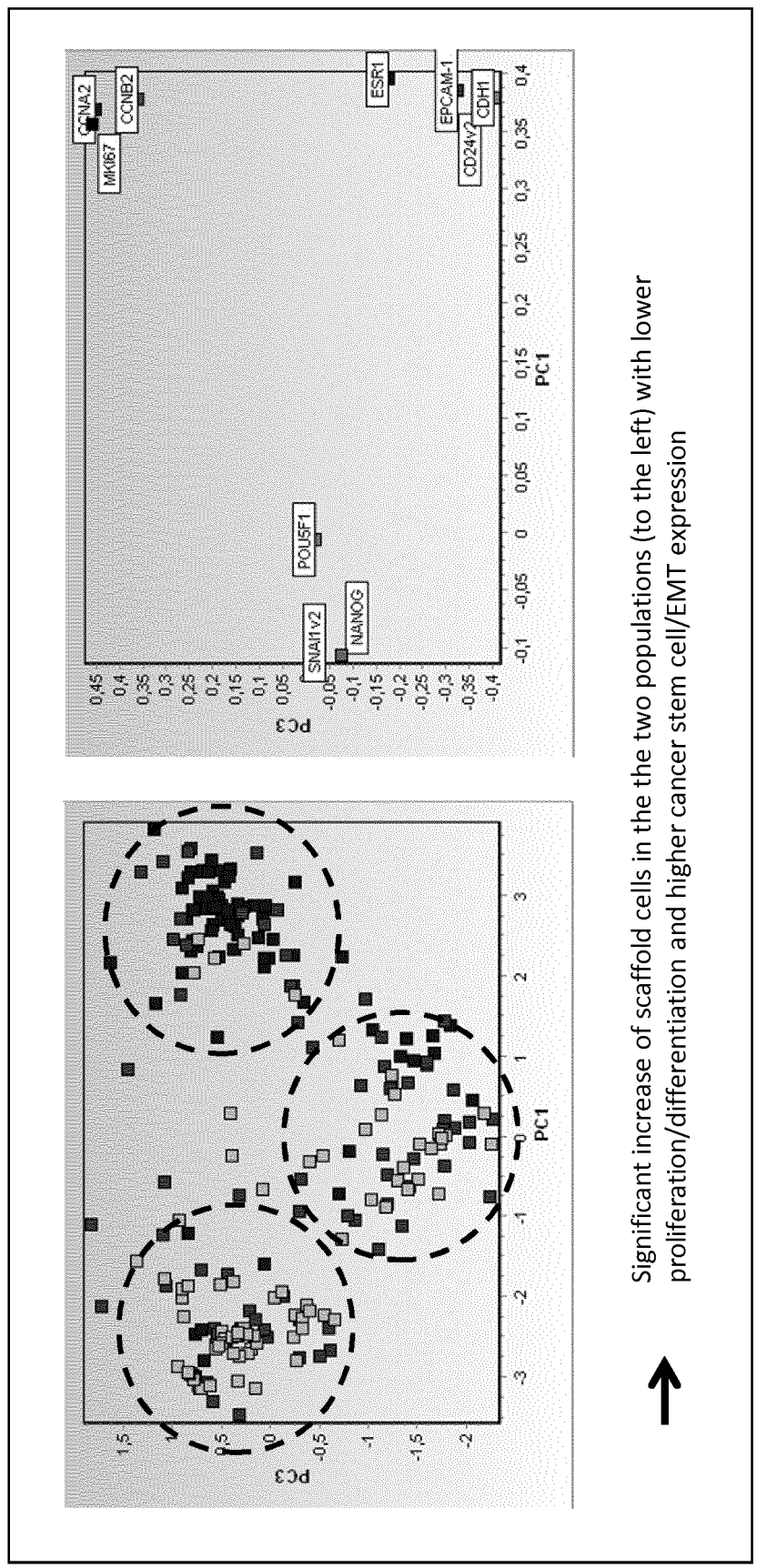
FIG. 10—Single cell PCR of two scaffolds samples (grey) and a 2D control (dark) using selected genes involved in cell cycle control, differentiation, cancer stem cell and EMT regulation. In total, more than 250 separate cells were analysed and presented as PC1 and PC3 for the different cells and the corresponding gene loading.
Figure 11:
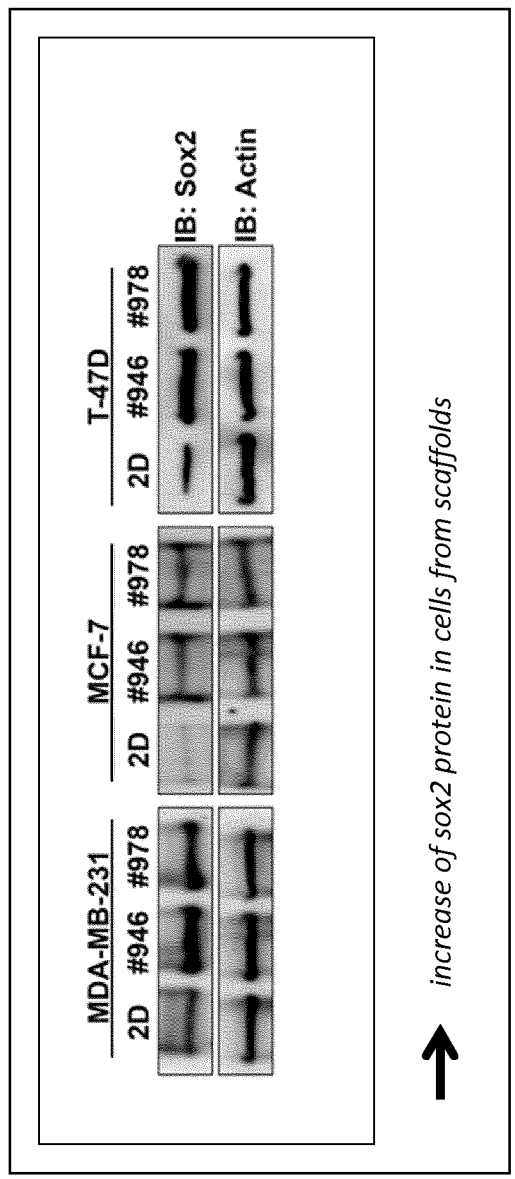
FIG. 11—Western blot analyses of Sox2 protein content in 2D and scaffold cultures (#946, #978) using three different breast cancer cell lines.

In vivo growth of cancer is often characterized by lower proliferation in general compared to regular cell cultures and a potentially different composition of differentiated and cancer stem cell subpopulations. The inventors therefore wanted to detail the existence of subgroups of cancer cells growing in scaffolds with a specific focus on cancer stem cell and EMT properties. Interestingly, when analyzing several markers for cancer stem cells, pluripotency, EMT, differentiation and proliferation in sets of cancer cell lines grown in various scaffolds as well as under regular 2D conditions it was clear that scaffolds cultures had higher expression of cancer stem cell and pluripotency markers as SOX-2, NANOG and CD44. Proliferation and differentiation was in contrast lowered in the scaffold cultures compared to 2D growing cells (FIG. 7). These results suggest that cell lines dedifferentiated towards more cancer stem cell and EMT features alternatively that these subgroups of cells selectively survived better when infiltrating and encountering the cancer scaffolds. To verify these data the inventors isolated cancer cells from three weeks of scaffolds cultures and performed various surrogate cancer stem cell assay on these cells and compared the results with the same cell line grown under regular 2D-conditions. The mammosphere assay is based on the principle that progenitor and cancer stem cells are anoikis resistant under non-adherent growth conditions and as illustrated in FIG. 8, cells from scaffolds had significantly higher mammosphere fractions compared to 2D-cultures. MDA231 breast cancer cells from scaffolds and 2D growths were also injected subcutaneously in immunocompromised NOG-mice and the tumour take and xenograft growth was monitored. In support for increased cancer stem cell features in scaffolds the inventors also observed a significantly increased tumour take in mice when injecting scaffold cells in comparison to 2D grown cells (FIG. 9). Finally, the inventors wanted to exactly monitor the composition of various subgroups of cancer cells using a single-cell PCR approach and 96 cells of 2D grown MCF7 cells as well as 96 cells from two independent scaffold cultures using the same cell line were single cell sorted by flow cytometry and sets of markers for cancer stem cell, pluripotency, differentiation, EMT and proliferation was measured on each cell using a qPCR approach. The results showed that 2D grown control cell mainly consisted of a large cluster of differentiated and highly proliferative cells whereas the two scaffolds had a significantly increase in the less proliferative and more stem cell defined clusters as indicated in FIG. 10. These comprehensive data clearly support that scaffold growth will promote cancer stem cell features and low proliferative subpopulations lacking differentiation and was verified at the protein level by Western Blotting indicating an increased protein expression of sox2 protein in scaffold cultured breast cancer cells (FIG. 11).

Figure 12:
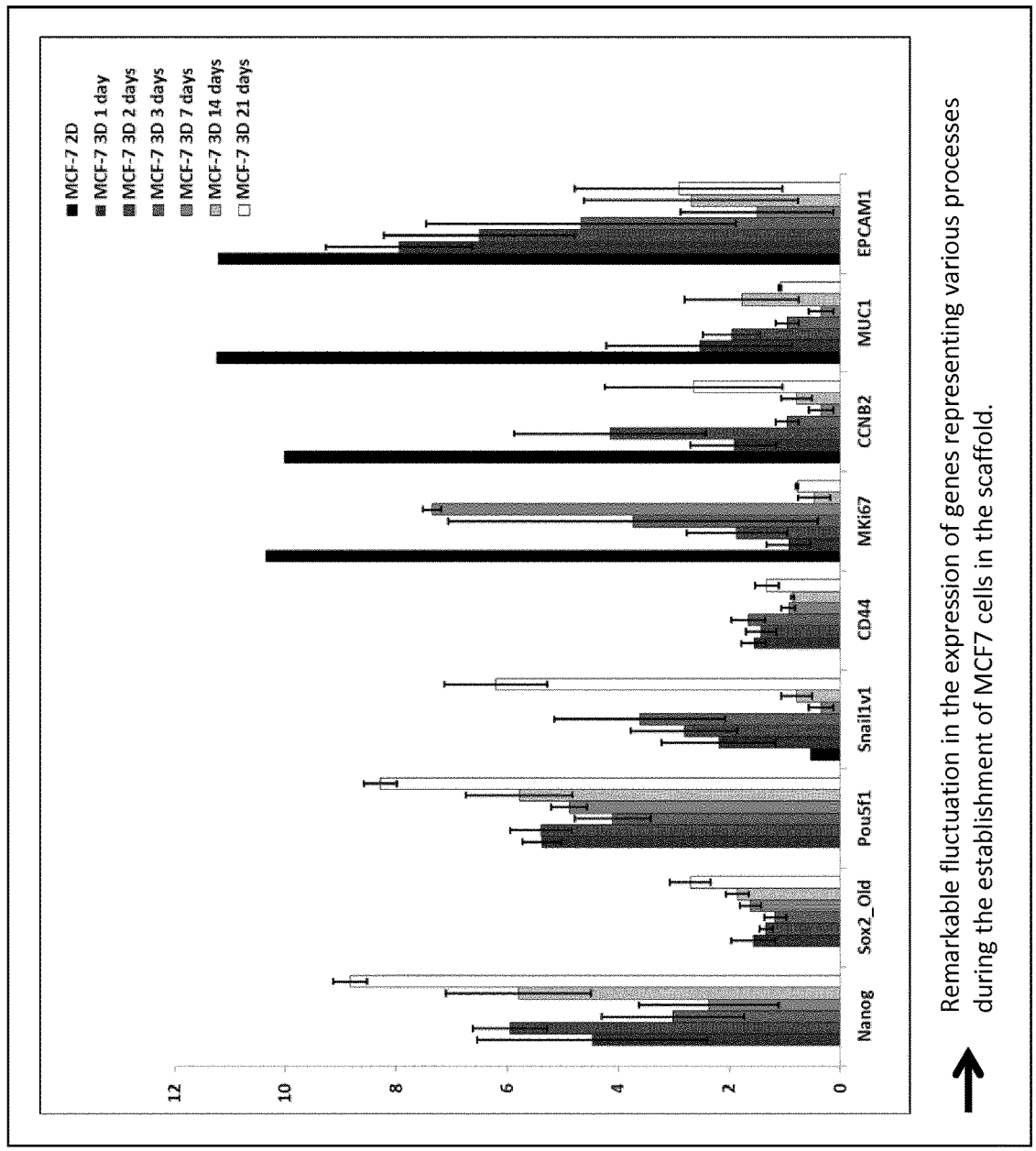
FIG. 12—Time course of induced qPCR changes in MCF7 cells grown in 2D and three different scaffolds (mean expression). Bars left to right show results for: MCF-7 2D; MCF7-3D 1 day; MCF7-3D 2 days; MCF7-3D 3 days; MCF7-3D 7 days; MCF7-3D 14 days; and MCF7-3D 21 days.

The kinetics of the changes in differentiation and proliferation was then studied in a cell-free scaffold divided into several separate pieces. Breast cancer MCF7 and MDA231 cells were grown on the pieces and samples were harvested day 1, 2, 3, 7, 14 and 21 and bulk qPCR analyses were performed using several markers for cancer stem cells, EMT, differentiation and proliferation as outlined above. The results clearly suggest that when cancer cells grow in scaffolds a highly coordinated and orchestrated series of events is initiated resulting in high stem cell and EMT features paralleled with low proliferation and drop of differentiation markers after three weeks of growth. Interestingly, waves of activation and inactivation could be observed during growth and at day one there was instant expression of cancer stem cell markers peaking early followed by an EMT peak at day three and proliferation peak at day seven after an initial drop as illustrated for MCF7 cells in FIG. 12. Differentiation markers declined during growth and there was a final settling after 2-3 weeks with high stem cell/EMT features and low proliferation/differentiation. The cancer stem cell changes were consistent between the two cell lines whereas proliferation dropped later in MDA231 cells whereas the, for this subtype of cancer, less relevant differentiation markers, did not change during growth (data not shown). The immediate increase in cancer stem cell features of MCF7 cells grown on scaffolds suggest that cells initiate a dedifferentiation process which will end up in a larger fraction of cancer stem cells after several weeks of scaffolds growth.

Figure 13:
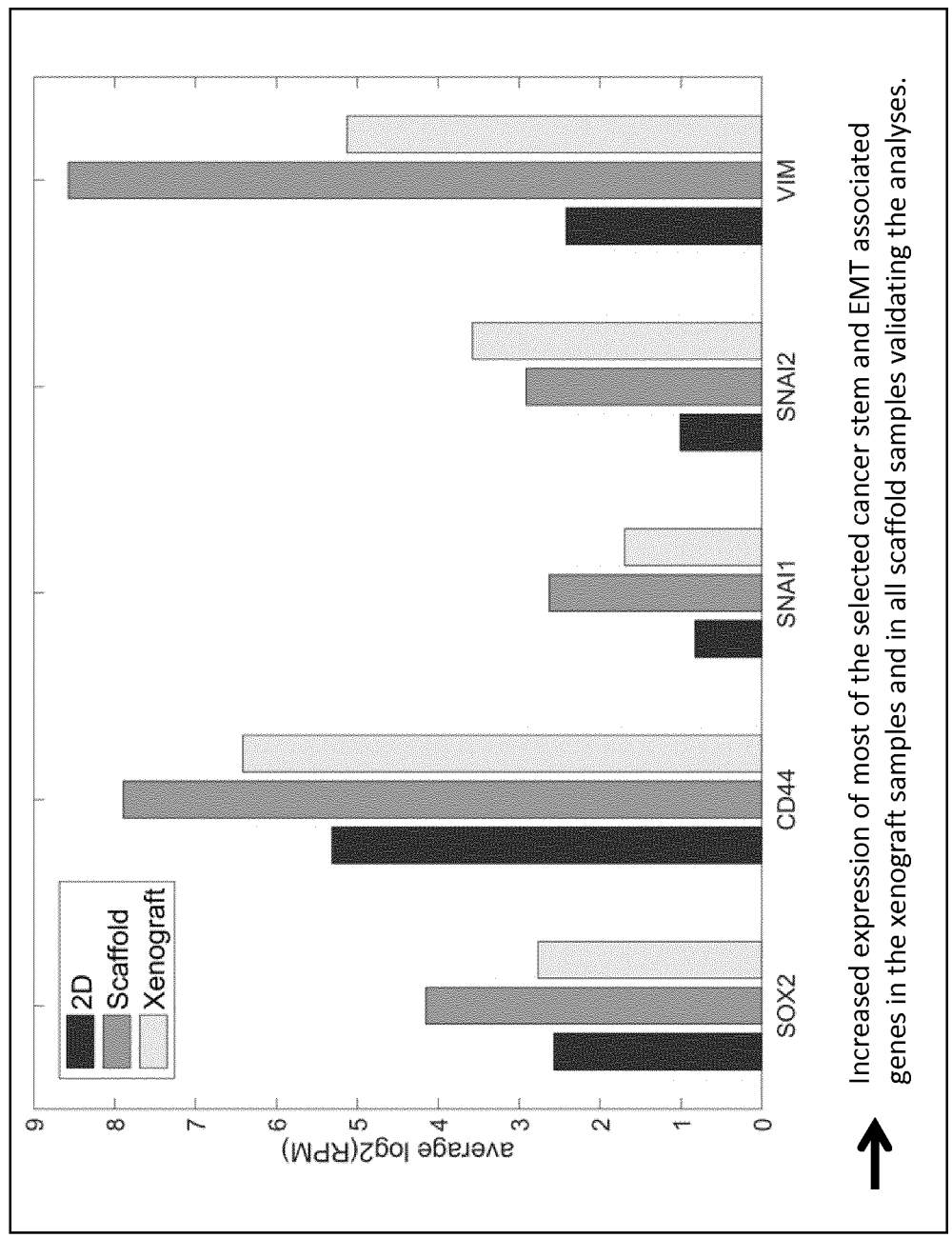
FIG. 13—Next generation RNA-sequencing (NGS) analyses of 2D, scaffold and xenograft samples of MCF7 cells and illustration of selected genes involved in cancer stem cell and EMT regulation.
Figure 14:
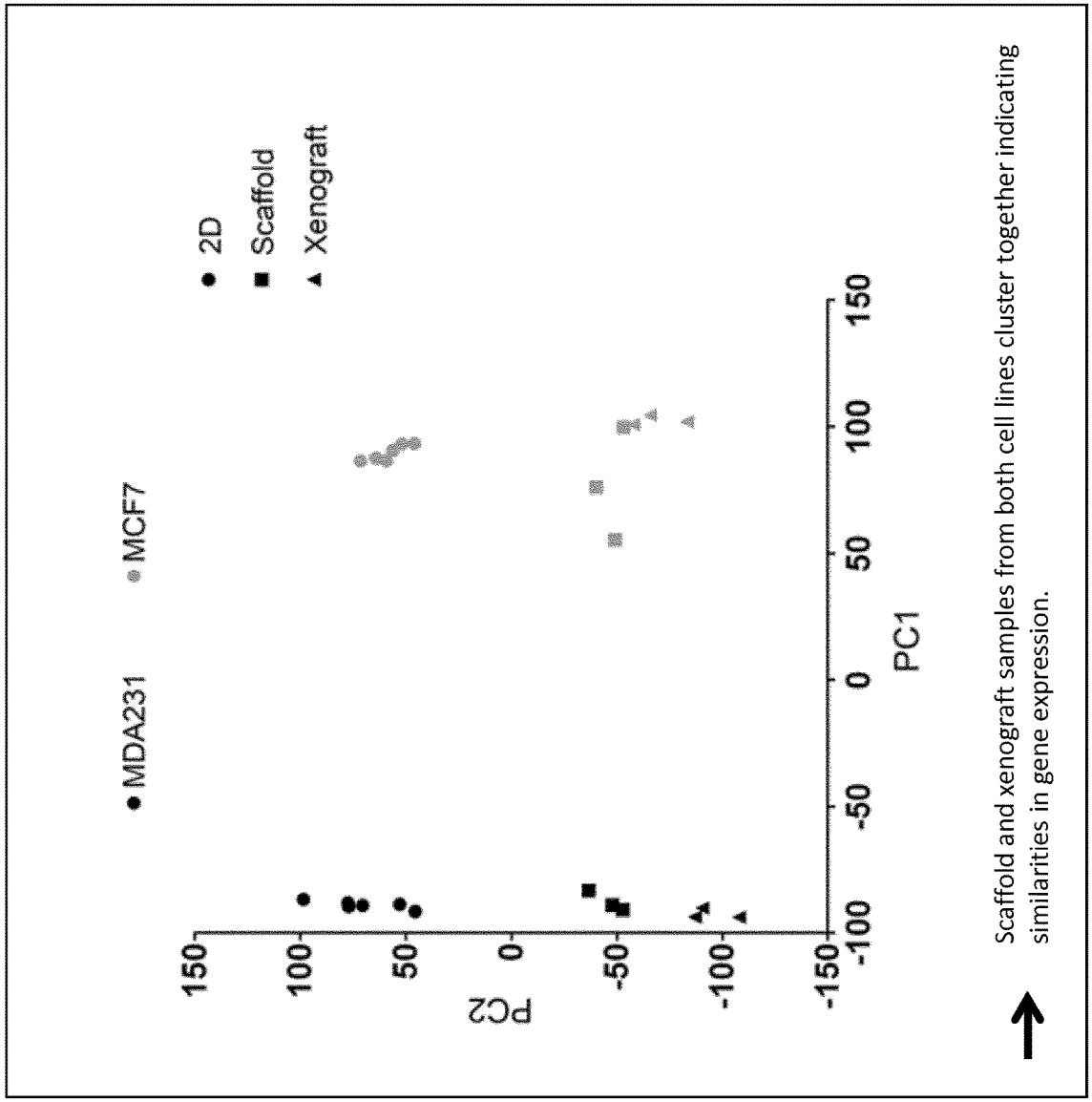
FIG. 14—Next generation RNA-sequencing (NGS), whole transcriptome analyses of 2D, scaffold and xenograft samples (immunocompromised mice) of the two breast cancer cell lines MCF7 and MDA231.
Figure 15:
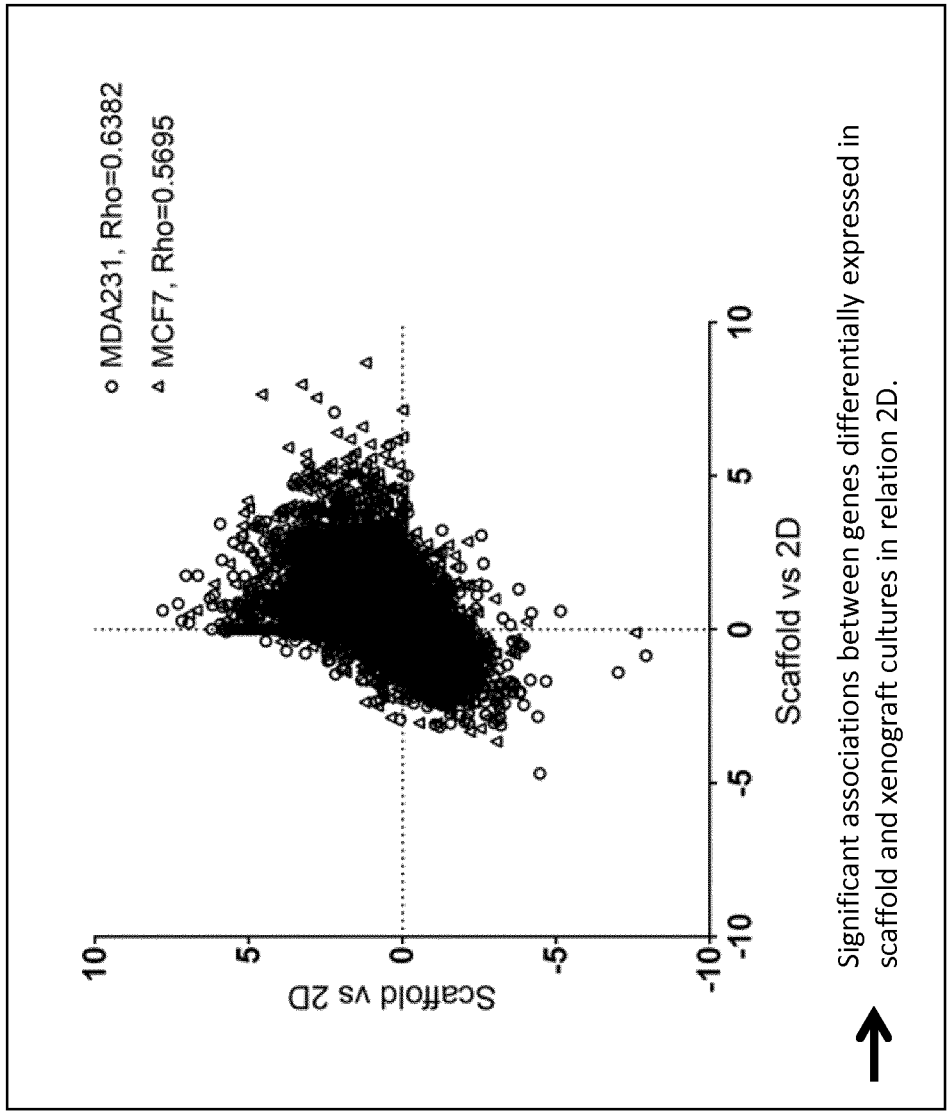
FIG. 15—NGS of 2D, scaffolds and xenografts samples and comparisons of similarities in expression between scaffolds and xenografts cultures in relation to 2D FIG. 16—Venn diagram illustration of NGS data and mutually regulated genes between the three growth conditions.
Figure 16:
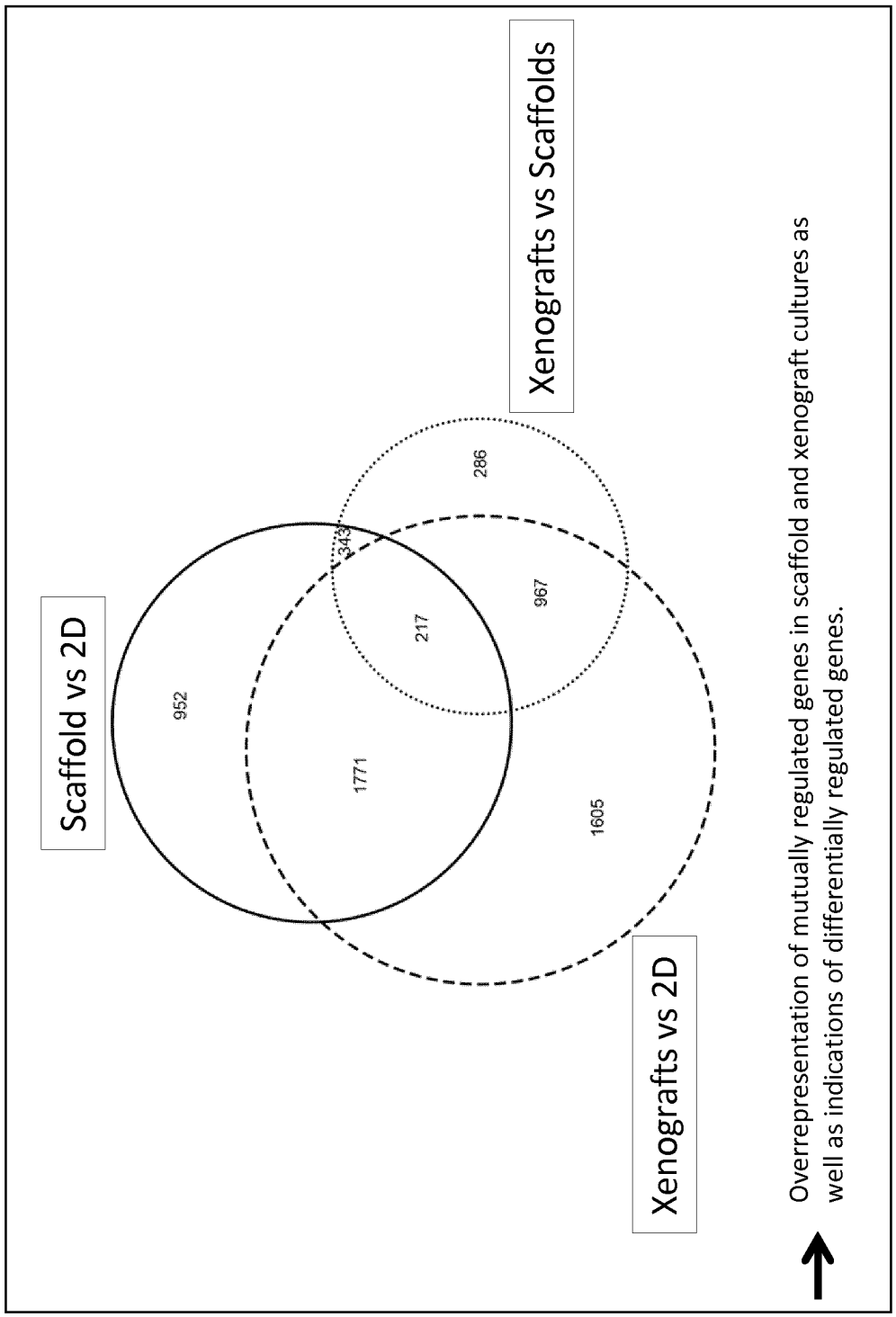
Figure 17:
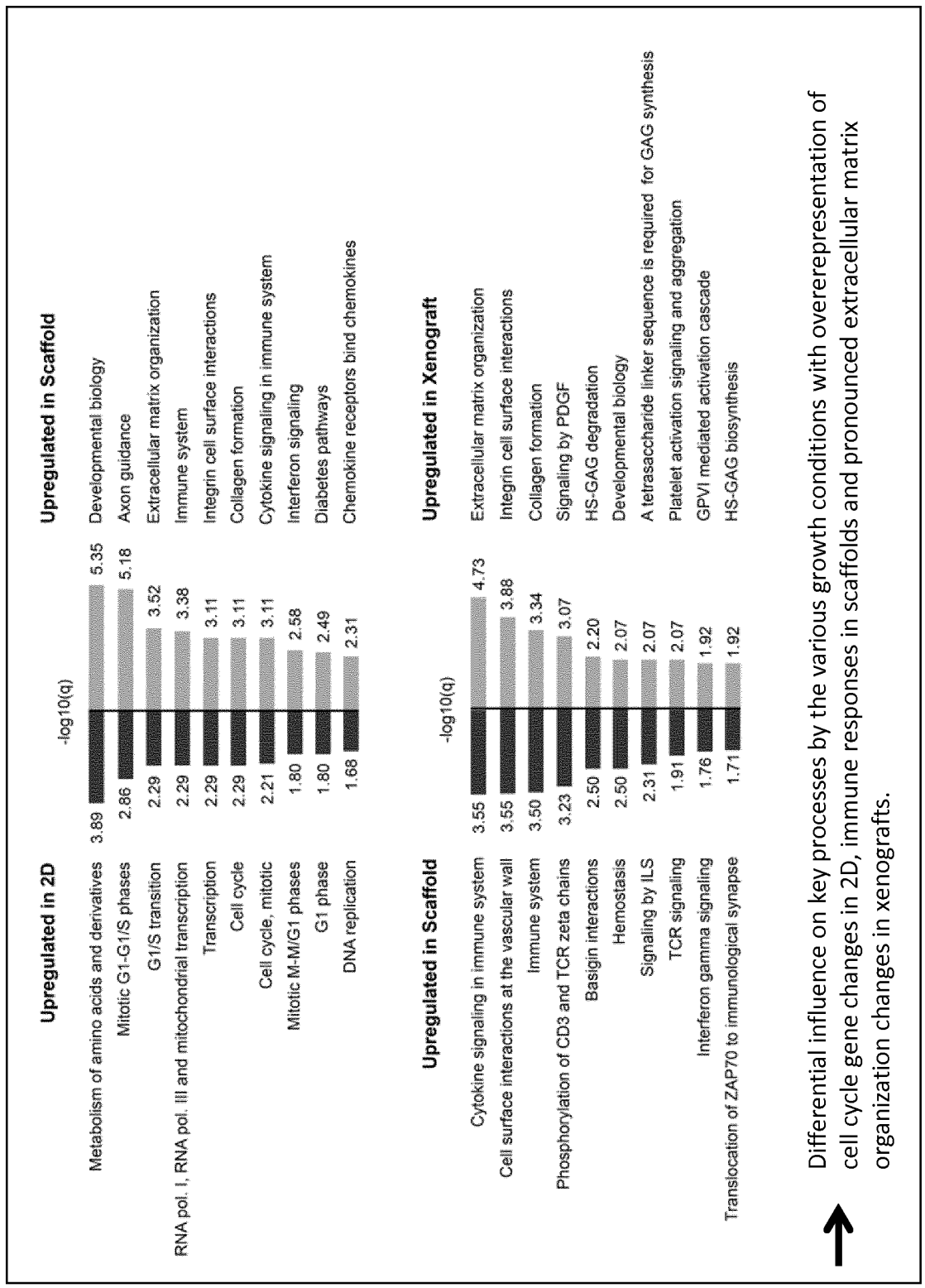
FIG. 17—Identification of enriched processes in the various culture conditions based on NGS analyses of MCF7cells.

Since there is huge need for relevant in vivo like growth model systems for cancer studies and drug screening protocols that could replace animal experiments the inventors next wanted to delineate similarities and differences between 2D cultures, scaffold cultures and xenografts samples using next generation sequencing (NGS) covering genome wide transcription. As illustrated in FIG. 13, plotting a selection of genes associated with cancer stem cells and EMT features, there was indeed an increased expression of the majority of the plotted genes validating the earlier described change in cancer stem cells in scaffold cultures. PCA illustrations of the NGS data are presented in FIG. 14 and scaffold cultures clustered close to xenograft cultures and separate from 2D cultures. The two cell lines separated in PC1 as expected but the relation between 2D, scaffold and xenograft cultures were similar for the two cell lines verifying that scaffold and xenografts were similar. The overlap and relation between the transcriptional changes as well as effected processes for the various growth processes are illustrated in FIGS. 15, 16 and 17 supporting similarities as well as some differences between scaffold and xenograft cultures. Typical processes upregulated in 2D growth conditions were related to cell cycle and proliferation control whereas scaffolds were enriched for immune systems, collagen formation and ECM organization. When comparing scaffolds with xenografts there was a more pronounced upregulation of extracellular matrix organization, PDGF signaling in the xenografts whereas ILS and TCR signaling was upregulated in scaffolds to mention a few.

Since the inventors had detailed NGS data from cancer cells growing in scaffolds as well as information about the protein composition of the scaffolds and some obvious clusters as presented above they next wanted to identify potential links between the protein scaffold data and expression differences in scaffolds compared to 2D using a combined bioinformatics approach. Initial gene set enrichment analyses (GSEA) indicated large overlaps between the pathways/reactomes enriched for among scaffold proteins as well as the upregulated genes in the MCF7 and MDA231 cells. Of the top 10 most significant reactomes in MCF7 cells, five were also among the top 10 in the scaffold protein. For MDA 231, four out of ten were among this list clearly supporting functional links between the identified scaffold proteins and regulated genes in cancer cells growing in the scaffolds as summarized in FIG. 18 for the top hundred reactomes. When extending the pathway analyses of potential interactions for the identified proteins in the scaffold including one additional protein level interaction for each protein, three significant modules with overrepresented and associated processes were identified. These modules were defined from the protein data and NGS data from MCF7 and MDA231 cells were then added, with links and key proteins and genes being identified in the combined bioinformatics analyses. Module one represented "signaling" and consisted of; signal transduction, signaling by SCF-KIT, downstream signal transduction and signaling by VEGF, VEGFA-VEGFR2. Module 2 was "repair and stress" related and consisted of DNA Repair, Cellular responses to stress, Cytosolic sensors of pathogen-associated DNA, Generic Transcription Pathway and SUMOylation. Module 3 was "DNA-replication" and included Synthesis of DNA, DNA Replication, M/G1 Transition and DNA Replication Pre-Initiation. The key proteins in the scaffold responsible for the most central processes as well as the separate modules are presented in Table G. Proteins and associated genes in the two cell lines defined as representative for the central processes and nodes thereby potentially highlighting key regulatory proteins and genes initiating and mediating the observed changes in cancer stem cell and EMT features are also listed in Table G.

Figure 19:
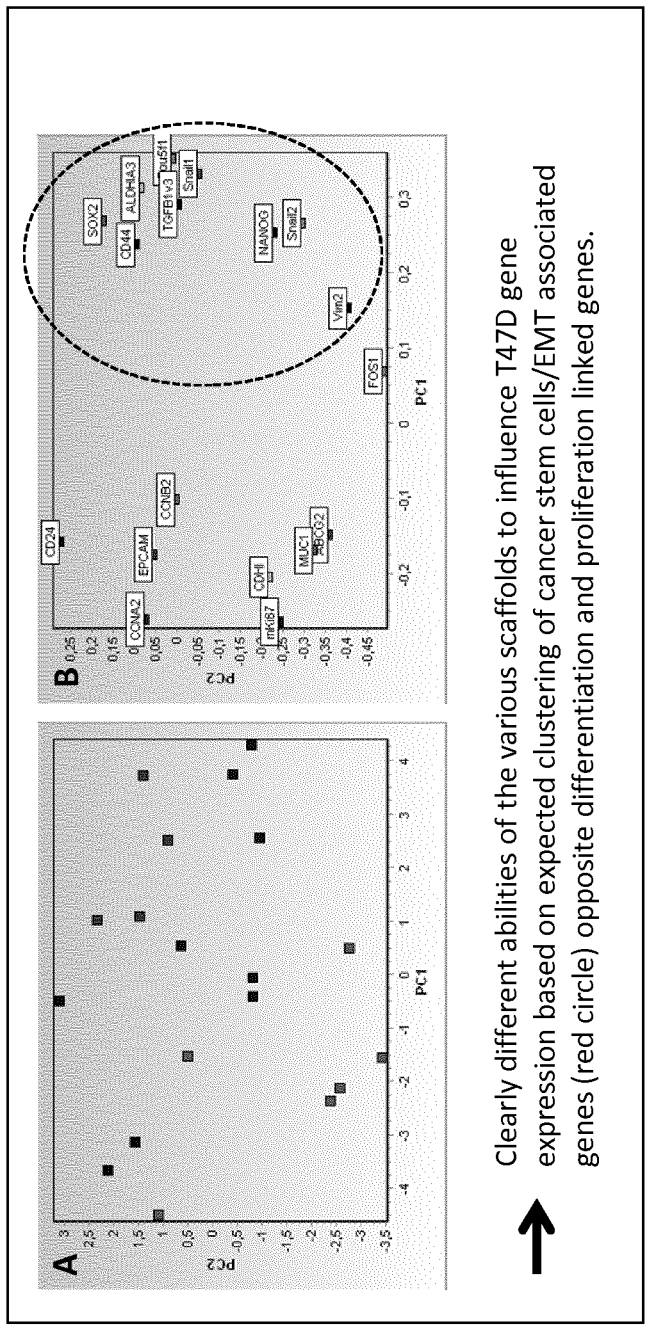
FIG. 19—PCA illustrations of qPCR analyses of T47D cells grown in 19 different scaffolds indicating a spread of the different scaffold samples (A) and the influence of the various genes analysed (B).
Figure 20:
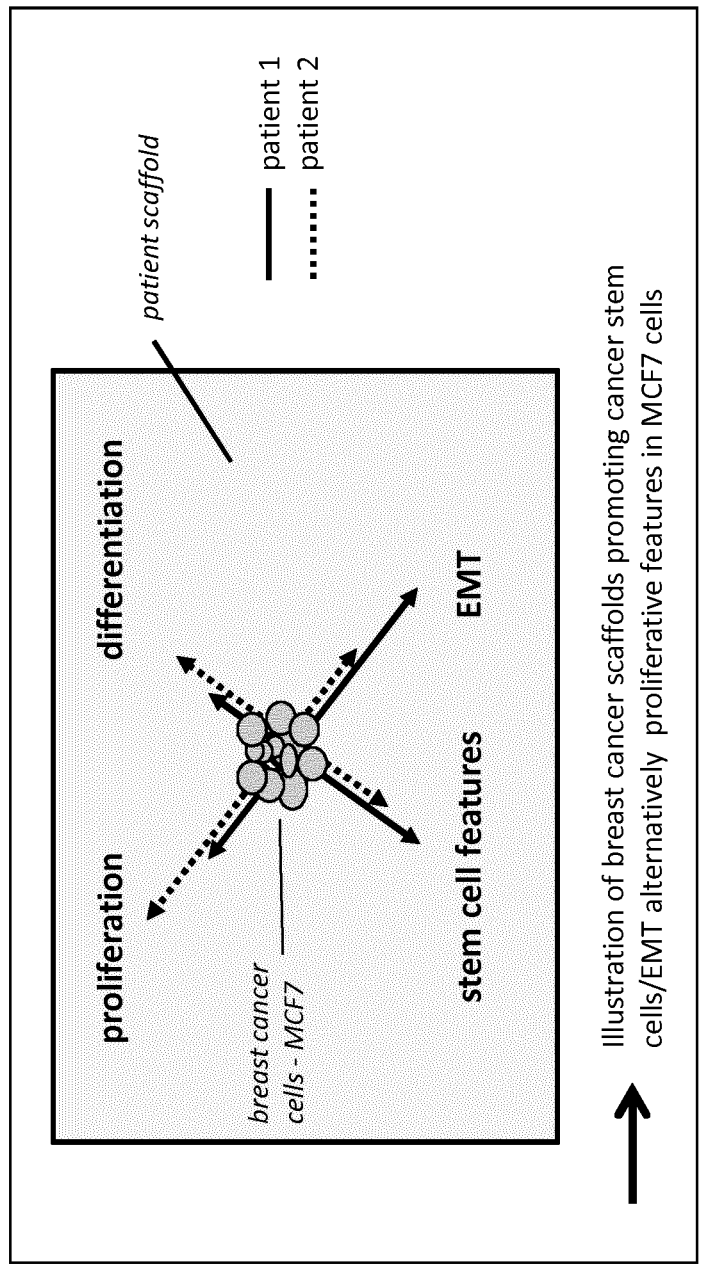
FIG. 20—Schematic principle and illustration of scaffolds as a clinical test of the tumour promoting effect of the specific cancer patients scaffolds measured by changes in gene expression of MCF7 cells.
Figure 21:
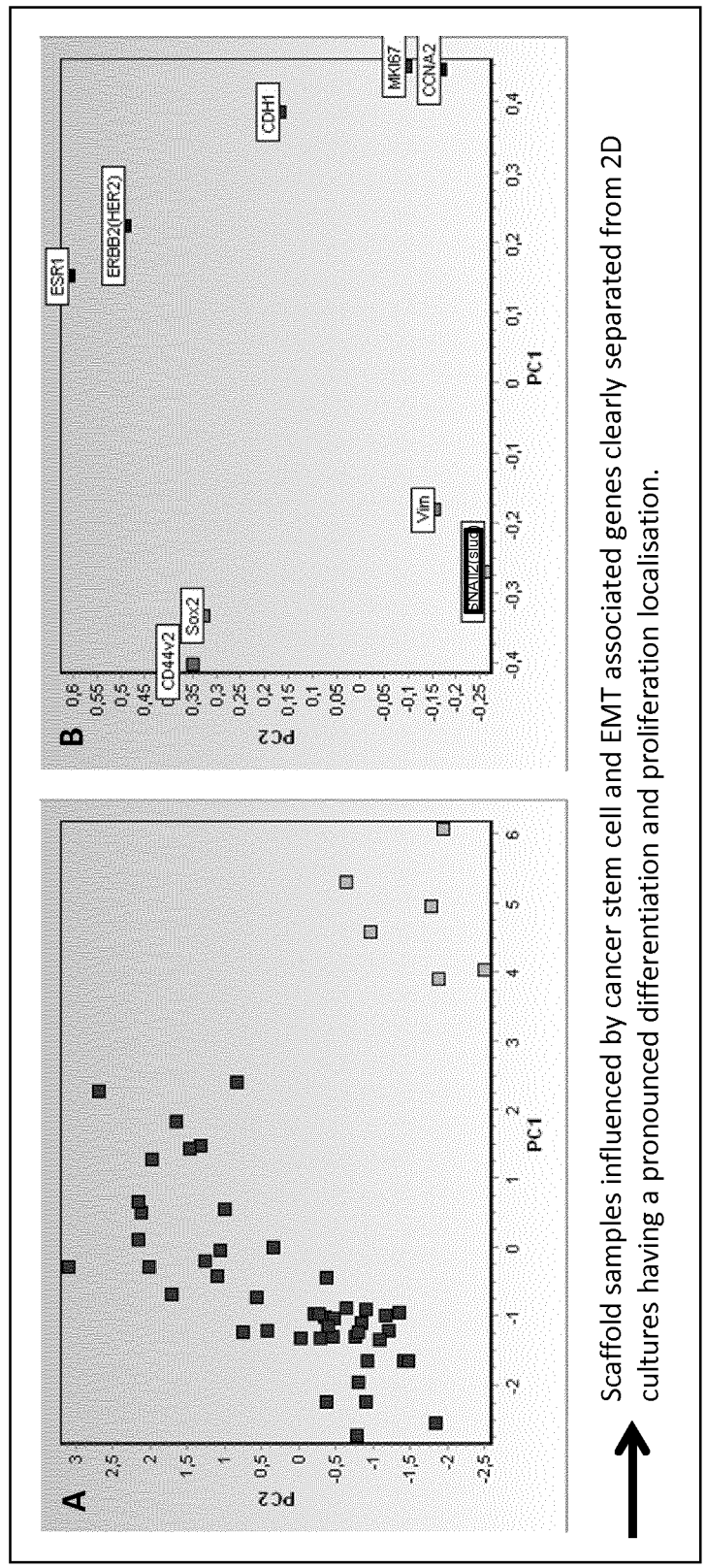
FIG. 21—PCA illustrations of qPCR analyses of MCF7 cells grown in 46 different scaffolds (dark) and six 2D controls (grey) (A) and the influence of the genes analysed (B).
Figure 22:
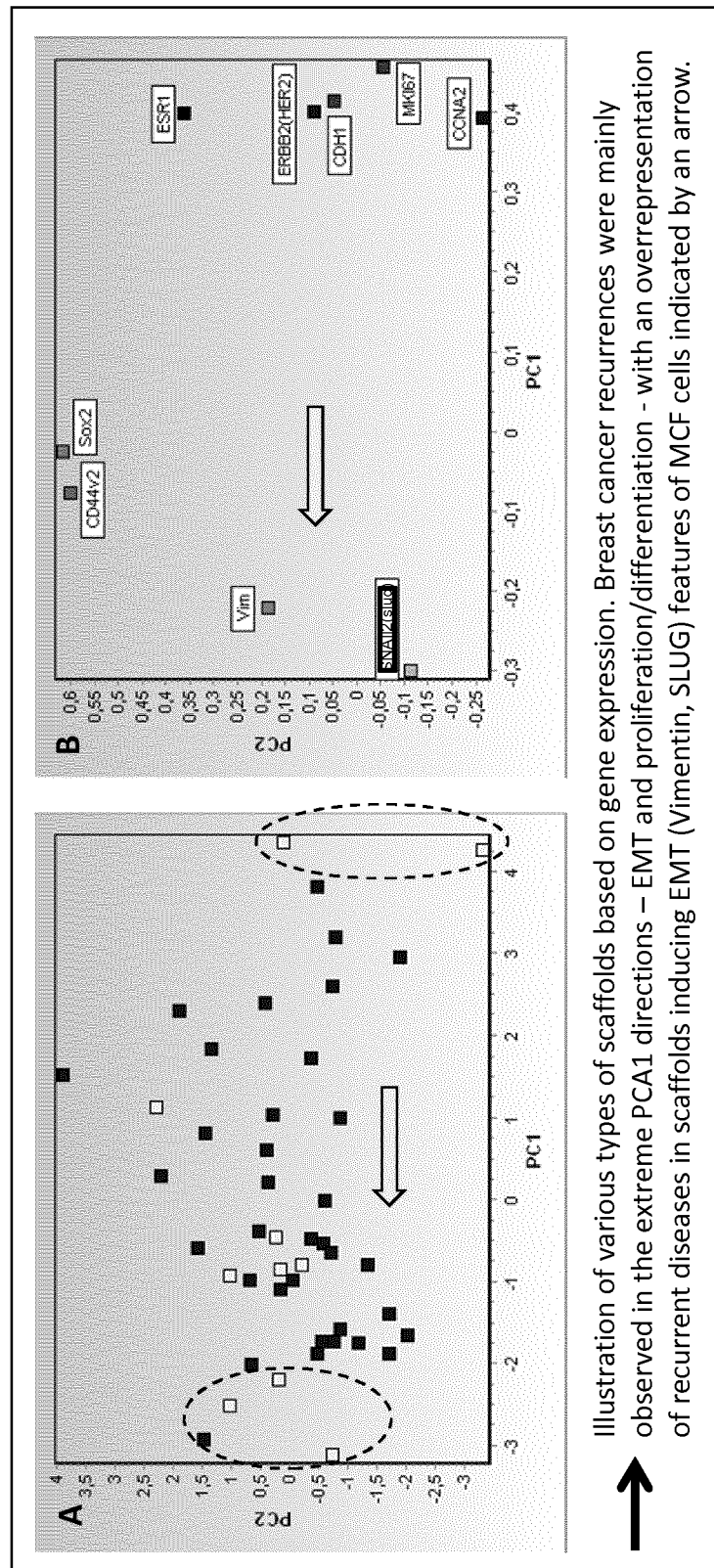
FIG. 22—PCA illustrations of qPCR analyses of MCF7 cells grown in 46 different scaffolds with indication of scaffolds from patients with disease recurrences (grey) (A) and the influence and clustering of genes analysed (B).
Figure 23:
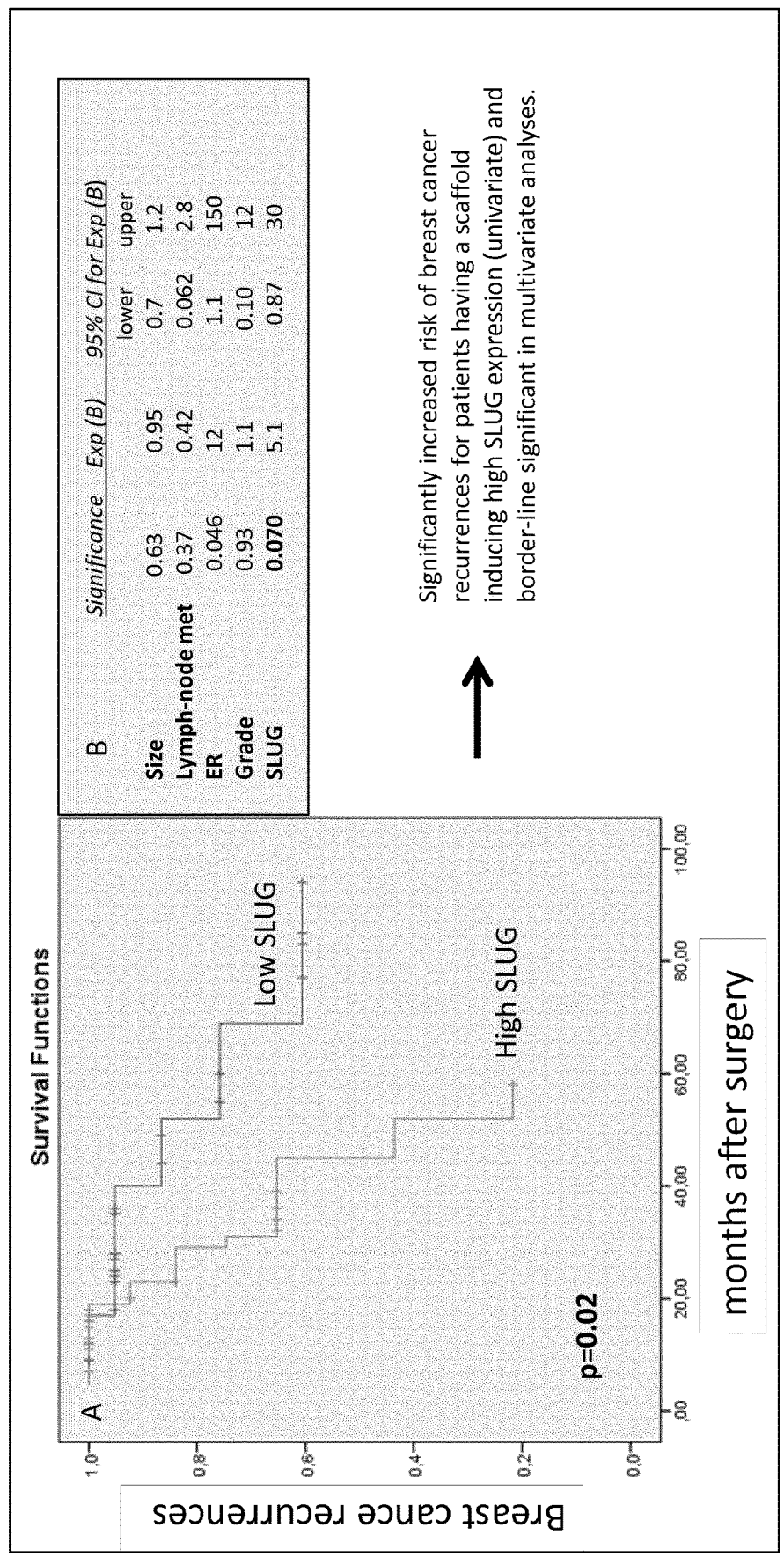
FIG. 23—Kaplan Meier plot of breast cancer recurrences in relation to SLUG expression (cut-off median) in MCF7 cells grown in the different cancer scaffolds obtained from patients (n=46) included in the study (A) and Cox multivariate analyses (B).
Figure 24:
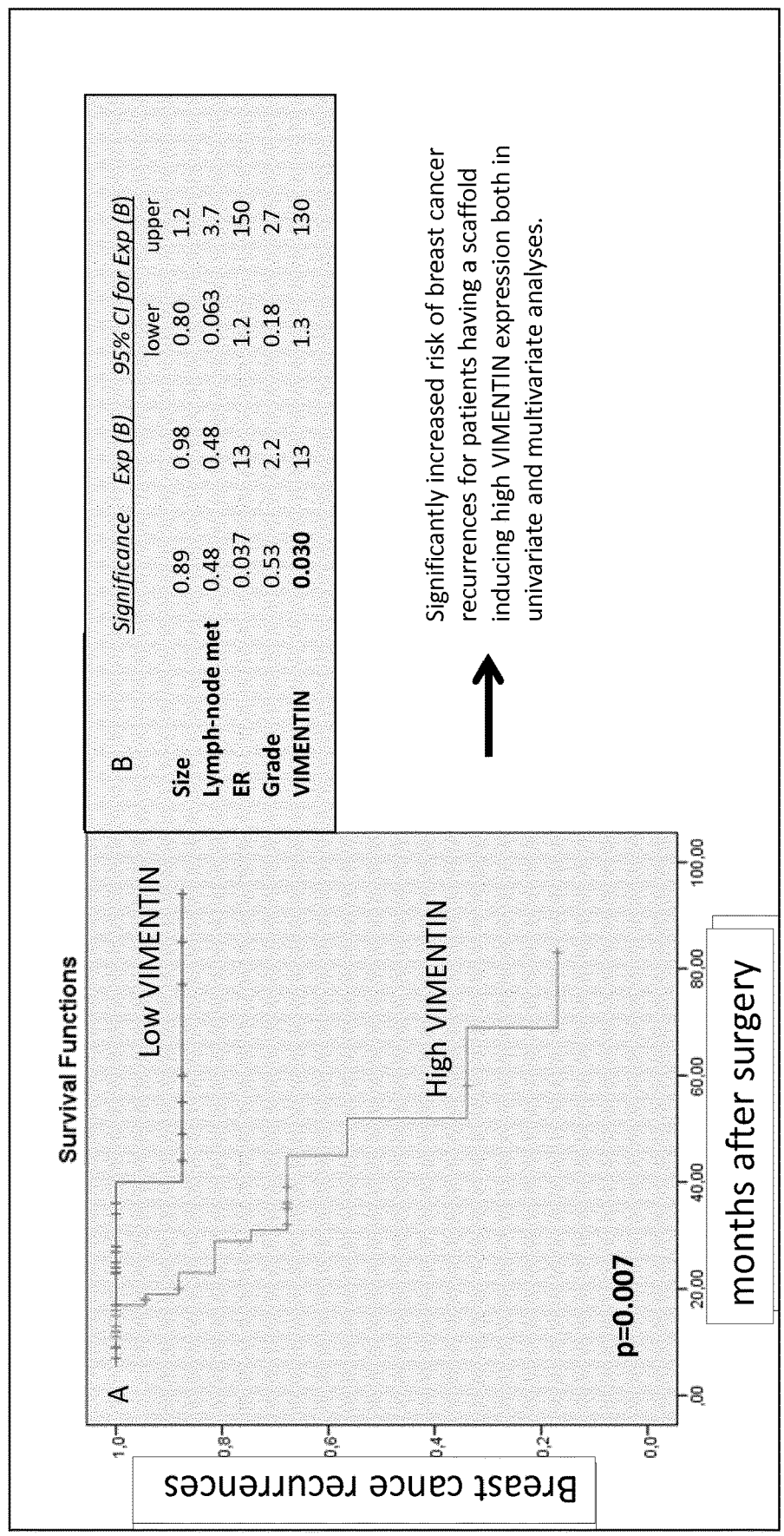
FIG. 24—Kaplan Meier plot of breast cancer recurrences in relation to VIMENTIN expression (cut-off median) in MCF7 cells grown in the different cancer scaffolds obtained from patients (n=46) included in the study (A) and Cox multivariate analyses (B).

It is clear that scaffolds in general will promote cancer stem cell and EMT features as presented above but the question remains if there is varying capacities in different scaffolds and if this potential difference is linked to a certain clinical behaviours or clinical subgroups. To test this hypothesis the inventors analysed a series of 20 scaffolds for bulk-PCR expression data for four different breast cancer cell lines grown three weeks on the scaffold. The PCR analyses included the same sets of markers for stem cells, differentiation, EMT and proliferation as used earlier and the inventors now wanted to compare the various scaffolds with regards to PCR changes in the "reporter" cell line grown on the scaffolds with the general aim to identify subgroups of scaffolds having more or less stem cell promoting capacities primarily. The data for T47D cells is illustrated in FIG. 19 and the scaffolds clearly separated in PC1 and PC2 whereas the loading genes clustered in cancer stem cell and EMT associated genes on one side and proliferation and differentiation linked genes on the opposite side. Similar findings were observed with the other cell lines tested supporting that the capacity for different scaffolds to induce cancer stem cell features vary (data not shown). These results lead to a model where the inventors hypothesise that the patient scaffold can influence various processes associated with tumour progression as illustrated in FIG. 20 and that this can be used as a test of the malignancy grade of that specific patient scaffold. Since the first set of 20 scaffolds were obtained directly from surgery with very limited follow-up time as well as material size the inventors could not investigate if the ability to induce cancer stem cell and EMT features for the scaffolds were linked to aggressiveness and cancer recurrences using this material. The inventors therefore extended the studies and analysed biobanked and frozen breast cancer samples with available longer follow-up data. Frozen samples could indeed be thawed and decellurised with the defined protocol producing scaffolds that could be used to grow cells with comparable PCR changes in the reporter cell line as freshly handled samples and scaffolds (data not shown). The inventors therefore identified a material of 46 frozen ductal breast cancer samples with available information about disease recurrences (median clinical follow-up time of 29 months, range 94 months). Scaffolds were prepared from the earlier frozen samples and MCF7 cells were grown on the scaffolds for three weeks before qPCR analyses of genes representing key processes representative for subgroups of cells present in MCF7 cells were performed. Some of the analysed genes (CCNB2, EPCAM, POU5S1) did not pass the quality demands and were not included in the following analyses. As illustrated in FIG. 21 including several 2D controls and 46 scaffold samples, all 2D control were separated from the scaffolds whereas scaffolds samples spread in PCA1 and PCA2 indicating that the scaffolds possessed varying "difference" from the 2D growth samples. When investigating how different genes effected the PCA analyses, four clear clusters could be observed consisting of 1) Sox2 and CD44, 2) SLUG and VIMENTIN, 3) CCNA2 and Ki67 and 4) ESR1 and ERBB2. When only analyzing the scaffold samples without the 2D controls the inventors obtained similar clustering and effects of genes and scaffold samples spread in PC1 and PC2 as illustrated in FIG. 22. Breast cancer recurrences are further indicated in the PC plot and there was a clear overrepresentation of recurrences in the part of PC plot affected by SLUG and VIMENTIN. There were further recurrences in the opposite and extreme direction affected by differentiation and proliferation. When analyzing breast cancer recurrences in relation to qPCR changes in MCF7 cells using Kaplan Meier plots and log rank analyses, SLUG and VIMENTIN expression changes were also significantly linked to recurrences using univariate analyses (p=0.02 and p=0.007 respectively) as illustrated in FIGS. 23 and 24. VIMENTIN was further independently linked to disease recurrences (p=0.03) in a multi variate analyses including tumour grade, size, lymph-node metastases and ER (FIG. 24 indeed supporting that the information obtained from the scaffolds is highly important in relation to conventional prognostic parameters.

These data suggest that it is mainly the EMT promoting effect of a scaffold that is linked to breast cancer recurrences whereas more proliferation or pure cancer stem cell promoting effects were not significantly linked to recurrences in this rather limited tumor set only including ductal breast cancer. The data indeed highlight that measurements of changes in a cell line grown in the scaffold can reveal important and novel information about the malignancy and also support that the environment and the scaffold will influence tumour promoting features that can be measured in the developed growth platform and assay. Also when analyzing the data with a PCA-approach and indicating scaffolds associated with breast cancer recurrences as illustrated in FIG. 22 it is clear that the disease recurrences are not evenly distributed in the scatter but is overrepresented in the direction mostly affected by VIMENTIN and SLUG expression.

Summary

Cancer cells are surrounded and actively interact with the microenvironment at the primary site of growth as well as metastatic niches. Key components in the cancer environment have been linked to various aggressive cancer features and can further influence the essential subpopulation of cancer stem cells most likely governing malignant properties and treatment resistance. In order to identify and specifically enumerate the influence of a specific cancer microenvironment the inventors have developed and characterized a novel cell culture platform using cell free scaffolds from primary breast cancer samples infiltrated with breast cancer cells. This in vivo like growth system induced a series of orchestrated changes in differentiation, EMT and proliferation of the cancer population with a final remarkable cancer stem cell expansion as defined by several surrogate assays and functional tests. Scaffold cultures were further more similar to xenograft cultures compared to regular 2D cultures as illustrated by NGS-analyses supporting an in vivo like growth in the scaffolds.

Despite a general promotion of cancer stem cell features in scaffolds, the ability varied and some scaffolds induced more EMT features whereas others preserved a differentiated and proliferative phenotype of cancer cells. Mass spectrometry analyses of cell-free scaffolds further identified subgroups of scaffolds based on the protein composition that also mirrored clinical properties such as tumour grade, supporting scaffold based micro environmental heterogeneity.

By combining the mass spectrometry data with NGS analyses identifying transcriptional changes in the cancer cells, the inventors could identify central processes and over represented modules both regarding proteins in the scaffold as well as key regulatory events in the cancer cell lines further supporting the existence of subgroups of scaffolds.

A theoretically important read-out of the scaffold platform is the varying ability for the scaffold to induce specific changes in cancer cells and the potential link to clinical behaviours and properties and this was studied in a material of 47 earlier frozen breast cancer samples with available clinical follow-up. Interestingly, EMT induced changes as represented by an increase of SLUG or Vimentin in the breast cancer cell line MCF7 growing in the scaffolds, was significantly linked to breast cancer recurrences and aggressive properties of the donor breast cancer (Vimentin, p=0.03, multivariate analyses).

The developed scaffold model system has the potential to optimally mimic in vivo like growth conditions revealing hidden and highly relevant clinical information about the malignancy inducing property of the specific scaffold earlier surrounding and indeed influencing cancer progressing properties.

Tables A-H

TABLE A

Tumour Progression Marker Genes
Accession/Version Numbers are with respect to the National Center for Biotechnology Information (NCBI) database as at 1 Nov. 2016.

| | Marker Gene Name | Accession Number | Version Number |
|---|---|---|---|
| Proliferation Markers | CCNB2 | NM_004701 | NM_004701.3 |
| | CCNA2 | NM_001237 | NM_001237.4 |
| | CDKN1A | NM_000389 | NM_000389.4 |
| | CDKN2A | NM_000077 | NM_000077.4 |
| | MKi67 | NM_001145966 | NM_001145966.1 |
| | CDK4 | NM_000075 | NM_000075.3 |
| | CDK6 | NM_001145306 | NM_001145306.1 |
| Differentiation Markers | EPCAM | NM_002354 | NM_002354.2 |
| | PGR | NM_000926 | NM_000926.4 |
| | ESR1 | NM_000125 | NM_000125.3 |
| | CD24 | NM_013230 | NM_013230.3 |
| | CDH1 | NM_001317184 | NM_001317184.1 |
| | ERBB2 | NM_001005862 | NM_001005862.2 |
| Cancer stem cell/pluripotency Markers | POU5F1 | NM_002701 | NM_002701.5 |
| | NANOG | NM_024865 | NM_024865.3 |
| | SOX2 | NM_003106 | NM_003106.3 |
| | FOSL1 | NM_005438 | NM_005438.4 |
| | TGFB1 | NM_000660 | NM_000660.6 |
| | CD44 | NM_000610 | NM_000610.3 |
| | ALDH1A1 | NM_000689 | NM_000689.4 |
| | ALDH1A3 | NM_000693 | NM_000693.3 |
| | ABCG2 | NM_004827 | NM_004827.2 |
| EMT Markers | SNAIL1 | NM_005985 | NM_005985.3 |
| | TWIST1 | NM_000474 | NM_000474.3 |
| | SNAIL2 | NM_003068 | NM_003068.4 |
| | VIM | NM_003380 | NM_003380.3 |
| | CDH2 | NM_001792 | NM_001792.4 |

Tables B-F—Key Proteins Identified in the Scaffolds Linked to Subtypes of Scaffolds, Grade and Key Processes The Tables list proteins identified by dynamic PCA of mass spectrometry data identifying Cluster 1 and Cluster 2, as well as proteins significantly linked to tumour grade or tumour proliferation (Ki67). Directions of associations are shown within brackets. There is overlap between PCA Cluster 2 and high grade/proliferation. AccessionNersion Numbers are with respect to SwissProt_2015_04_verINS.fasta Version: 2.3, as at 29 Oct. 2016.

TABLE B

|  | Protein Name | Accession Number | Database Version Number |
|---|---|---|---|
| PCA Cluster 1 | POSTN | Q15063 | Q15063.2 |
|  | ANXA5 | P08758 | P08758.2 |
|  | PRELP | P51888 | P08758.2 |
|  | MYO1C | O00159 | O00159.4 |
|  | CD47 | Q08722 | Q08722.1 |
|  | FBLN2 | P98095 | P98095.2 |
|  | SNG2 | O43760 | O43760.1 |
|  | DERM | P35908 | P35908.2 |
|  | IGHA1 | P01876 | P01876.2 |
|  | ITIH1 | P19827 | P19827.3 |
|  | SC22B | O75396 | O75396.4 |
|  | SAMP | P02743 | P02743.2 |
|  | LUM | P51884 | P51884.2 |
|  | PGS1 | P21810 | P21810.2 |
|  | COL6A2 | P12110 | P12110.4 |
|  | COL6A3 | P12111 | P12111.5 |
|  | COL6A1 | P12109 | P12109.3 |
|  | ALBU | P02768 | P02768.2 |
|  | TM109 | Q9BVC6 | Q9BVC6.1 |
|  | K22E | P35908 | P35908.2 |
| PCA Cluster 2 | ENPL | P14625 | P14625.1 |
|  | CH60 | P10809 | P10809.2 |
|  | CKAP4 | Q07065 | Q07065.2 |
|  | HS90A | P07900 | P07900.5 |
|  | ENOA | P06733 | P06733.2 |
|  | HS90B | P08238 | P08238.4 |
|  | G3P | P04406 | P04406.3 |
|  | K6PL | P17858 | P17858.6 |
|  | HSP7C | P11142 | P11142.1 |
|  | IF4A1 | P60842 | P60842.1 |
|  | TBA1C | Q9B0E3 | Q9B0E3.1 |
|  | HNRPQ | O60506 | O60506.2 |
|  | DX39B | Q13838 | Q13838.1 |
|  | HNRPF | P52597 | P52597.3 |
|  | EF1A1 | P68104 | P68104.1 |
|  | TBB5 | P07437 | P07437.2 |
|  | HSPB1 | P04792 | P04792.2 |
|  | FLNA | P21333 | P21333.4 |
|  | LMAN1 | P49257 | P49257.2 |
|  | MYH9 | P35579 | P35579.4 |
|  | ACTB | P60709 | P60709.1 |
|  | TBB5 | P07437 | P07437.2 |
|  | RS3 | P23396 | P23396.2 |

TABLE C

Proteins significantly linked to high proliferation (p = 0.01-0.05)

| Protein Name | Positive or negative association | Accession Number | Version Number |
|---|---|---|---|
| K6PL | + | P17858 | P17858.6 |
| HS90A | + | P07900 | P07900.5 |
| IF4A1 | + | P60842 | P60842.1 |
| PGS1 | − | P21810 | P21810.2 |
| ENOA | + | P06733 | P06733.2 |
| PRELP | − | P51888 | P51888.1 |
| SNG2 | − | O43760 | O43760.1 |
| CH60 | + | P10809 | P10809.2 |
| LUM | − | P16615 | P16615.1 |
| HS90B | + | P08238 | P08238.4 |

TABLE D

Proteins most significantly linked to high proliferation (p < 0.01)

| Protein Name | Positive or negative association | Accession Number | Version Number |
|---|---|---|---|
| K6PL | + | P17858 | P17858.6 |
| HS90A | + | P07900 | P07900.5 |
| IF4A1 | + | P60842 | P60842.1 |

TABLE E

Proteins significantly linked to high grade (p = 0.01-0.05)

| Protein Name | Positive or negative association | Accession Number | Version Number |
|---|---|---|---|
| HS90A | + | P07900 | P07900.5 |
| ENOA | + | P06733 | P06733.2 |
| HS90B | + | P08238 | P08238.4 |
| IF4A1 | + | P60842 | P60842.1 |
| K6PL | + | P17858 | P17858.6 |
| PRELP | − | P51888 | P51888.1 |
| SNG2 | − | O43760 | O43760.1 |
| CD47 | − | Q08722 | Q08722.1 |
| PGS1 | − | P21810 | P21810.2 |
| CH60 | + | P10809 | P10809.2 |
| TBA1C | + | Q9BQE3 | Q9BQE3.1 |
| HSP7C | + | P11142 | P11142.1 |

TABLE F

Proteins most significantly linked to high grade (p < 0.01)

| Protein Name | Positive or negative association | Accession Number | Version Number |
|---|---|---|---|
| HSP90A | + | P07900 | P07900.5 |
| ENOA | + | P06733 | P06733.2 |
| HS90B | + | P08238 | P08238.4 |
| IF4A1 | + | P60842 | P60842.1 |
| K6PL | + | P17858 | P17858.6 |
| PRELP | − | P51888 | P51888.1 |
| SNG2 | − | O43760 | O43760.1 |

TABLE G

List of proteins and linked up-or down-regulated genes from NGS-data in MCF7 and MDA231 cells, in the three different modules identified by GSEA-analyses. A summary of the most central genes of interest and the linked scaffold proteins is further listed.
Gene Accession/Version Numbers are with respect to the National Center for Biotechnology Information (NCBI) database as at 2 Nov. 2016. Protein Accession/Version Numbers are with respect to SwissProt_2015_04_verINS.fasta Version: 2.3, as at 29 Oct. 2016.

Module 1

| MCF7 upregulated | | | MDA-MB-231 upregulated | | |
|---|---|---|---|---|---|
| Marker Name | Accession Number | Version Number | Marker Name | Accession Number | Version Number |
| ANXA1 | NM_000700 | NM_000700.2 | COL17A1 | NM_000494 | NM_000494.3 |
| CAMK4 | NM_001323374 | NM_001323374.1 | EPOR | NM_000121 | NM_000121.3 |
| CAV1 | NM_001753 | NM_001753.4 | ERBB3 | NM_001982 | NM_001982.3 |
| CEACAM1 | NM_001712 | NM_001712.4 | FHIT | NM_001320899 | NM_001320899.1 |
| COL17A1 | NM_000494 | NM_000494.3 | GSN | NM_000177 | NM_000177.4 |
| DAPK1 | NM_004938 | NM_004938.3 | IGF1R | NM_000875 | NM_000875.4 |
| DMD | NM_000109 | NM_000109.3 | IL4R | NM_000418 | NM_000418.3 |
| DPYSL2 | NM_001197293 | NM_001197293.2 | ITGB4 | NM_000213 | NM_000213.4 |
| DYSF | NM_001130987 | NM_001130987.1 | MAP3K5 | NM_005923 | NM_005923.3 |
| EGFR | NM_005228 | NM_005228.3 | MAPK3 | NM_002746 | NM_002746.2 |
| FHIT | NM_001320899 | NM_001320899.1 | PARK2 | NM_004562 | NM_004562.2 |
| ITGA6 | NM_001079818 | NM_001079818.2 | PDE4D | NM_001104631 | NM_001104631.1 |
| MST1R | NM_002447 | NM_002447.3 | PFN2 | NM_053024 | NM_053024.3 |
| NPHP1 | NM_000272 | NM_000272.3 | P1K3CG | NM_002649 | NM_002649.3 |
| PAK1 | NM_001128620 | NM_001128620.1 | PLD1 | NM_002662 | NM_002662.4 |
| PDE4D | NM_001104631 | NM_001104631.1 | PPL | NM_002705 | NM_002705.4 |
| PKD1 | NM_001009944 | NM_001009944.2 | RGS2 | NM_002923 | NM_002923.3 |
| PLD1 | NM_002662 | NM_002662.4 | RPS6KA3 | NM_004586 | NM_004586.2 |
| PRKCA | NM_002737 | NM_002737.2 | SNX9 | NM_016224 | NM_016224.4 |
| RAC2 | NM_002872 | NM_002872.4 | SVIL | NM_003174 | NM_003174.3 |
| RASA1 | NM_002890 | NM_002890.2 | TUBA1A | NM_001270399 | NM_001270399.1 |
| RGS2 | NM_002923 | NM_002923.3 | | | |
| RPS6KA3 | NM_004586 | NM_004586.2 | | | |
| SH2B3 | NM_005475 | NM_005475.2 | | | |
| SVIL | NM_003174 | NM_003174.3 | | | |
| TGFB1I1 | NM_001042454 | NM_001042454.2 | | | |
| TNIK | NM_015028 | NM_015028.3 | | | |
| TRIO | NM_007118 | NM_007118.3 | | | |

| MCF7 downregulated | | | MDA-MB-231 down regulated | | |
|---|---|---|---|---|---|
| Marker Name | Accession Number | Version Number | Marker Name | Accession Number | Version Number |
| HCK | NM_002110 | NM_002110.3 | BIRC5 | NM_001168 | NM_001168.2 |
| JAK1 | NM_001320923 | NM_001320923.1 | BYSL | NM_004053 | NM_004053.3 |
| KRT18 | NM_000224 | NM_000224.2 | CAMK2B | NM_001220 | NM_001220.4 |
| KRT8 | NM_001256282 | NM_001256282.1 | CAMK4 | NM_001323374 | NM_001323374.1 |
| MAP2 | NM_002374 | NM_002374.3 | CASP3 | NM_004346 | NM_004346.3 |
| NME1-NME2 | NM_001018136 | NM_001018136.2 | DYSF | NM_001130987 | NM_001130987.1 |
| | | | NOS3 | NM_000603 | NM_000603.4 |
| | | | TH | NM_199292 | NM_199292.2 |

| Scaffold proteins | | |
|---|---|---|
| Protein name | Accession Number | Version Number |
| ATP2A2 | P16615 | P16615.1 |
| FLNA | P21333 | P21333.4 |
| GNB2L1 | P63244 | P63244.3 |
| GSN | P06396 | P06396.1 |
| HSP90AA1 | P07900 | P07900.5 |
| KRT10 | P13645 | P13645.6 |
| KRT18 | P05783 | P05783.2 |
| KRT8 | P05787 | P05787.7 |
| PLEC | Q15149 | Q15149.3 |
| TGM2 | P21980 | P21980.2 |
| TUBB4B | P68371 | P68371.1 |

Module 2

| MCF7 upregulated | | | MDA-MB-231 upregulated | | |
|---|---|---|---|---|---|
| Marker Name | Accession Number | Version Number | Marker Name | Accession Number | Version Number |
| ALDOA | NM_000034 | NM_000034.3 | ATM | NM_000051 | NM_000051.3 |
| ATM | NM_000051 | NM_000051.3 | ATXN1 | NM_000332 | NM_000332.3 |
| ATXN1 | NM_000332 | NM_000332.3 | EIF2AK3 | NM_004836 | NM_004836.6 |

TABLE G-continued

List of proteins and linked up-or down-regulated genes from NGS-data in MCF7 and MDA231 cells, in the three different modules identified by GSEA-analyses. A summary of the most central genes of interest and the linked scaffold proteins is further listed. Gene Accession/Version Numbers are with respect to the National Center for Biotechnology Information (NCBI) database as at 2 Nov. 2016. Protein Accession/Version Numbers are with respect to SwissProt_2015_04_verINS.fasta Version: 2.3, as at 29 Oct. 2016.

| | | | | | |
|---|---|---|---|---|---|
| CARD11 | NM_001324281 | NM_001324281.1 | EP300 | NM_001429 | NM_001429.3 |
| EIF2AK3 | NM_004836 | NM_004836.6 | ESR1 | NM_000125 | NM_000125.3 |
| FOS | NM_005252 | NM_005252.3 | GADD45G | NM_006705 | NM_006705.3 |
| FRMD6 | NM_001042481 | NM_001042481.2 | HDAC5 | NM_005474 | NM_005474.4 |
| GADD45A | NM_001924 | NM_001924.3 | LRP5 | NM_002335 | NM_002335.3 |
| GADD45G | NM_006705 | NM_006705.3 | NR3C2 | NM_000901 | NM_000901.4 |
| GOLM1 | NM_016548 | NM_016548.3 | PPARGC1A | NM_001330751 | NM_001330751.1 |
| GSTP1 | NM_000852 | NM_000852.3 | PPM1A | NM_021003 | NM_021003.4 |
| JUN | NM_002228 | NM_002228.3 | RABAC1 | NM_006423 | NM_006423.2 |
| KAT2B | NM_003884 | NM_003884.4 | SP1 | NM_138473 | NM_138473.2 |
| LIST | NM_000081 | NM_000081.3 | SUMO4 | NM_001002255 | NM_001002255.1 |
| NPAS2 | NM_002518 | NM_002518.3 | TNFAIP3 | NM_001270508 | NM_001270508.1 |
| PIM1 | NM_001243186 | NM_001243186.1 | YAP1 | NM_001130145 | NM_001130145.2 |
| PLA2G4A | NM_024420 | NM_024420.2 | | | |
| PPP1R15A | NM_014330 | NM_014330.3 | | | |
| PRNP | NM_000311 | NM_000311.3 | | | |
| RUNX1T1 | NM_004349 | NM_004349.3 | | | |
| SMAD4 | NM_005359 | NM_005359.5 | | | |
| SORBS2 | NM_003603 | NM_003603.6 | | | |
| SOX9 | NM_000346 | NM_000346.3 | | | |
| SUMO4 | NM_001002255 | NM_001002255.1 | | | |
| TNFAIP3 | NM_001270508 | NM_001270508.1 | | | |
| WEE1 | NM_003390 | NM_003390.3 | | | |
| YAP1 | NM_001130145 | NM_001130145.2 | | | |

| MCF7 downregulated | | | MDA-MB-231 downregulated | | |
|---|---|---|---|---|---|
| Marker Name | Accession Number | Version Number | Marker Name | Accession Number | Version Number |
| AIFM1 | NM_001130846 | NM_001130846.3 | AP2B1 | NM_001030006 | NM_001030006.1 |
| AP1B1 | NM_001127 | NM_001127.3 | BAG2 | NM_004282 | NM_004282.3 |
| BAG3 | NM_004281 | NM_004281.3 | E2F1 | NM_005225 | NM_005225.2 |
| FANCC | NM_000136 | NM_000136.2 | FANCC | NM_000136 | NM_000136.2 |
| FKBP5 | NM_004117 | NM_004117.3 | FEN1 | NM_004111 | NM_004111.5 |
| NQO1 | NM_000903 | NM_000903.2 | FKBP5 | NM_004117 | NM_004117.3 |
| SLC9A3R1 | NM_004252 | NM_004252.4 | MAP3K14 | NM_003954 | NM_003954.4 |
| SREBF1 | NM_001005291 | NM_001005291.2 | NQO1 | NM_000903 | NM_000903.2 |
| STUB1 | NM_005861 | NM_005861.3 | PARP1 | NM_001618 | NM_001618.3 |
| ZNF259 | NM_003904 | NM_003904.4 | PPP2R1B | NM_002716 | NM_002716.4 |
| | | | PRNP | NM_000311 | NM_000311.3 |
| | | | PSME3 | NM_005789 | NM_005789.3 |
| | | | RBL1 | NM_002895 | NM_002895.4 |
| | | | SLC9A3R1 | NM_004252 | NM_004252.4 |
| | | | TP73 | NM_005427 | NM_005427.3 |
| | | | ZNF259 | NM_003904 | NM_003904.4 |

| Scaffold proteins | | |
|---|---|---|
| Protein Name | Accession Number | Version Number |
| ANXA2 | P07355 | P07355.2 |
| CLTC | Q00610 | Q00610.5 |
| GAPDH | P04406 | P04406.3 |
| HNRNPU | Q00839 | Q00839.6 |
| HSP90AB1 | P08238 | P08238.4 |
| HSPA1A | P0DMV8.1 | P0DMV8.1 |
| PHB | P35232 | P35232.1 |
| PRKDC | P78527 | P78527.3 |
| UBC | P02747 | P02747.3 |

Module 3

| MCF7 upregulated | | | MDA-MB-231 upregulated | | |
|---|---|---|---|---|---|
| Marker Name | Accession Number | Version Number | Marker Name | Accession Number | Version Number |
| ALDH2 | NM_000690 | NM_000690.3 | BHLHE40 | NM_003670 | NM_003670.2 |
| BHLHE40 | NM_003670 | NM_003670.2 | BTBD2 | NM_017797 | NM_017797.3 |
| CRCT1 | NM_019060 | NM_019060.2 | CHD3 | NM_001005273 | NM_001005273.2 |
| PAEP | NM_001018049 | NM_001018049.2 | PSG9 | NM_002784 | NM_002784.4 |
| PIN | NM_002825 | NM_002825.6 | SPG7 | NM_003119 | NM_003119.3 |

TABLE G-continued

List of proteins and linked up-or down-regulated genes from NGS-data in MCF7 and MDA231 cells, in the three different modules identified by GSEA-analyses. A summary of the most central genes of interest and the linked scaffold proteins is further listed. Gene Accession/Version Numbers are with respect to the National Center for Biotechnology Information (NCBI) database as at 2 Nov. 2016. Protein Accession/Version Numbers are with respect to SwissProt_2015_04_verINS.fasta Version: 2.3, as at 29 Oct. 2016.

| | | | | | |
|---|---|---|---|---|---|
| SH3GL3 | NM_003027 | NM_003027.4 | TNFRSF14 | NM_003820 | NM_003820.3 |
| TNFRSF14 | NM_003820 | NM_003820.3 | TPD52L1 | NM_003287 | NM_003287.3 |
| VIM | VIM NM_003380 | NM_003380.3 | | | |

| MCF7 downregulated | | | MDA-MB-231 downregulated | | |
|---|---|---|---|---|---|
| Marker Name | Accession Number | Version Number | Marker Name | Accession Number | Version Number |
| HSPB1 | NM_001540 | NM_001540.3 | HSPD1 | NM_002156 | NM_002156.4 |
| TPD52L1 | NM_003287 | NM_003287.3 | KIF15 | NM_020242 | NM_020242.2 |
| | | | MAPKAPK3 | NM_001243926 | NM_001243926.1 |
| | | | XPO5 | NM_020750 | NM_020750.2 |

| Scaffold proteins | | |
|---|---|---|
| Protein Name | Accession Number | Version Number |
| EEF1A1 | P68104 | P68104.1 |
| HSPB1 | P04792 | P04792.2 |
| HSPD1 | P10809 | P10809.2 |
| PFKL | P17858 | P17858.6 |
| VIM | P08670 | P08670.4 |

Highly central genes and proteins of interest

| MCF7 upregulated | | | MDA-MB-231 upregulated | | |
|---|---|---|---|---|---|
| Marker Name | Accession Number | Version Number | Marker Name | Accession Number | Version Number |
| ATXN1 | NM_000332 | NM_000332.3 | ATXN1 | NM_000332 | NM_000332.3 |
| EGFR | NM_005228 | NM_005228.3 | C3 | NM_000064 | NM_000064.3 |
| FN1 | NM_212482 | NM_212482.2 | EP300 | NM_001429 | NM_001429.3 |
| LRP1 | NM_002332 | NM_002332.2 | ESR1 | NM_000125 | NM_000125.3 |
| NDRG1 | NM_001135242 | NM_001135242.1 | FN1 | NM_212482 | NM_212482.2 |
| PRKCA | NM_002737 | NM_002737.2 | LRP1 | NM_002332 | NM_002332.2 |
| SMAD4 | NM_005359 | NM_005359.5 | NDRG1 | NM_001135242 | NM_001135242.1 |
| SUMO4 | NM_001002255 | NM_001002255.1 | SUMO4 | NM_001002255 | NM_001002255.1 |
| SVIL | NM_003174 | NM_003174.3 | SVIL | NM_003174 | NM_003174.3 |
| VIM | NM_003380 | NM_003380.3 | | | |

| MCF7 downregulated | | | MDA-MB-231 downregulated | | |
|---|---|---|---|---|---|
| Marker Name | Accession Number | Version Number | Marker Name | Accession Number | Version Number |
| KRT18 | NM_000224 | NM_000224.2 | ACTN1 | NM_001130004 | NM_001130004.1 |
| | | | CASP3 | NM_004346 | NM_004346.3 |

| Scaffold protein | | |
|---|---|---|
| Protein name | Accession Number | Version Number |
| A2M | P01023 | P01023.3 |
| ACTB | P60709 | P60709.1 |
| ACTN1 | P12814 | P12814.2 |
| C3 | P01024 | P01024.2 |
| EEF1A1 | P68104 | P68104.1 |
| FLNA | P21333 | P21333.4 |
| FN1 | P02751 | P02751.4 |
| GAPDH | P04406 | P04406.3 |
| GNB2L1 | 63244 | 63244.3 |
| HSP90AA1 | P07900 | P07900.5 |
| HSPA1A | P0DMV8 | P0DMV8.1 |
| KRT18 | P05783 | P05783.2 |
| TGM2 | P21980 | P21980.2 |
| TUBB | P07437 | P07437.2 |
| VIM | P08670 | P08670.4 |
| YWHAB | P31946 | P31946.3 |

TABLE H

List of scaffold proteins identified by mass spectrometry analysis of scaffold Accession numbers are with respect to SwissProt_2015_04_verINS.fasta Version: 2.3, as at 29 Oct. 2016.

LOCUS K1C17_HUMAN 432 aa linear PRI 5 OCT. 2016
DEFINITION RecName: Full = Keratin, type I cytoskeletal 17; AltName: Full = 39.1;
AltName: Full = Cytokeratin-17; Short = CK-17; AltName:
Full = Keratin-17; Short = K17.
ACCESSION Q04695
VERSION Q04695.2
LOCUS K2C5_HUMAN 590 aa linear PRI 5 OCT. 2016
DEFINITION RecName: Full = Keratin, type II cytoskeletal 5; AltName: Full = 58 kDa
cytokeratin; AltName: Full = Cytokeratin-5; Short = CK-5; AltName:
Full = Keratin-5; Short = K5; AltName: Full = Type-II keratin Kb5.
ACCESSION P13647
VERSION P13647.3
LOCUS CO3A1_HUMAN 1466 aa linear PRI 5 OCT. 2016
DEFINITION RecName: Full = Collagen alpha-1(III) chain; Flags: Precursor.
ACCESSION P02461
VERSION P02461.4
LOCUS ASPH_HUMAN 758 aa linear PRI 5 OCT. 2016
DEFINITION RecName: Full = Aspartyl/asparaginyl beta-hydroxylase; AltName:
Full = Aspartate beta-hydroxylase; Short = ASP beta-hydroxylase;
AltName: Full = Peptide-aspartate beta-dioxygenase.
ACCESSION Q12797
VERSION Q12797.3
LOCUS K22E_HUMAN 639 aa linear PRI 5 OCT. 2016
DEFINITION RecName: Full = Keratin, type II cytoskeletal 2 epidermal; AltName:
Full = Cytokeratin-2e; Short = CK-2e; AltName: Full = Epithelial
keratin-2e; AltName: Full = Keratin-2 epidermis; AltName:
Full = Keratin-2e; Short = K2e; AltName: Full = Type-II keratin Kb2.
ACCESSION P35908
VERSION P35908.2
LOCUS FIBA_HUMAN 888 aa linear PRI 5 OCT. 2016
DEFINITION RecName: Full = Fibrinogen alpha chain; Contains: RecName:
Full = Fibrinopeptide A; Contains: RecName: Full = Fibrinogen alpha
chain; Flags: Precursor.
ACCESSION P02671
VERSION P02671.2
LOCUS ITIH1_HUMAN 911 aa linear PRI 5 OCT. 2016
DEFINITION RecName: Full = Inter-alpha-trypsin inhibitor heavy chain H1;
Short = ITI heavy chain H1; Short = ITI-HC1;
Short = Inter-alpha-inhibitor heavy chain 1; AltName:
Full = Inter-alpha-trypsin inhibitor complex component III; AltName:
Full = Serum-derived hyaluronan-associated protein; Short = SHAP;
Flags: Precursor.
ACCESSION P19827
VERSION P19827.3
LOCUS CO1A2_HUMAN 1366 aa linear PRI 5 OCT. 2016
DEFINITION RecName: Full = Collagen alpha-2(I) chain; AltName: Full = Alpha-2 type
I collagen; Flags: Precursor.
ACCESSION P08123
VERSION P08123.7
LOCUS CO1A1_HUMAN 1464 aa linear PRI 5 OCT. 2016
DEFINITION RecName: Full = Collagen alpha-1(I) chain; AltName: Full = Alpha-1 type
I collagen; Flags: Precursor.
ACCESSION P02452
VERSION P02452.5
LOCUS DERM_HUMAN 201 aa linear PRI 5 OCT. 2016
DEFINITION RecName: Full = Dermatopontin; AltName: Full = Tyrosine-rich acidic
matrix protein; Short = TRAMP; Flags: Precursor.
ACCESSION Q07507
VERSION Q07507.2
LOCUS FIBG_HUMAN 453 aa linear PRI 5 OCT. 2016
DEFINITION RecName: Full = Fibrinogen gamma chain; Flags: Precursor.
ACCESSION P02679
VERSION P02679.3
LOCUS ITIH2_HUMAN 946 aa linear PRI 5 OCT. 2016
DEFINITION RecName: Full = Inter-alpha-trypsin inhibitor heavy chain H2;
Short = ITI heavy chain H2; Short = ITI-HC2;
Short = Inter-alpha-inhibitor heavy chain 2; AltName:
Full = Inter-alpha-trypsin inhibitor complex component II; AltName:
Full = Serum-derived hyaluronan-associated protein; Short = SHAP;
Flags: Precursor.
ACCESSION P19823
VERSION P19823.2
LOCUS K1C9_HUMAN 623 aa linear PRI 5 OCT. 2016
DEFINITION RecName: Full = Keratin, type I cytoskeletal 9; AltName:
Full = Cytokeratin-9; Short = CK-9; AltName: Full = Keratin-9; Short = K9.
ACCESSION P35527

TABLE H-continued

List of scaffold proteins identified by mass spectrometry analysis of scaffold Accession numbers are with respect to SwissProt_2015_04_verINS.fasta Version: 2.3, as at 29 Oct. 2016.

VERSION P35527.3
LOCUS FIBB_HUMAN 491 aa linear PRI 5 OCT. 2016
DEFINITION RecName: Full = Fibrinogen beta chain; Contains: RecName:
Full = Fibrinopeptide B; Contains: RecName: Full = Fibrinogen beta
chain; Flags: Precursor.
ACCESSION P02675
VERSION P02675.2
LOCUS ALBU_HUMAN 609 aa linear PRI 5 OCT. 2016
DEFINITION RecName: Full = Serum albumin; Flags: Precursor.
ACCESSION P02768
VERSION P02768.2
LOCUS HACD2_HUMAN 254 aa linear PRI 5 OCT. 2016
DEFINITION RecName: Full = Very-long-chain (3R)-3-hydroxyacyl-CoA dehydratase 2;
AltName: Full = 3-hydroxyacyl-CoA dehydratase 2; Short = HACD2;
AltName: Full = Protein-tyrosine phosphatase-like member B.
ACCESSION Q6Y1H2
VERSION Q6Y1H2.1
LOCUS HBB_HUMAN 147 aa linear PRI 5 OCT. 2016
DEFINITION RecName: Full = Hemoglobin subunit beta; AltName: Full = Beta-globin;
AltName: Full = Hemoglobin beta chain; Contains: RecName:
Full = LVV-hemorphin-7; Contains: RecName: Full = Spinorphin.
ACCESSION P68871
VERSION P68871.2
LOCUS IGHA1_HUMAN 353 aa linear PRI 5 OCT. 2016
DEFINITION RecName: Full = Ig alpha-1 chain C region.
ACCESSION P01876
VERSION P01876.2
LOCUS CD47_HUMAN 323 aa linear PRI 5 OCT. 2016
DEFINITION RecName: Full = Leukocyte surface antigen CD47; AltName:
Full = Antigenic surface determinant protein OA3; AltName:
Full = Integrin-associated protein; Short = IAP; AltName: Full = Protein
MER6; AltName: CD_antigen = CD47; Flags: Precursor.
ACCESSION Q08722
VERSION Q08722.1
LOCUS K1C14_HUMAN 472 aa linear PRI 5 OCT. 2016
DEFINITION RecName: Full = Keratin, type I cytoskeletal 14; AltName:
Full = Cytokeratin-14; Short = CK-14; AltName: Full = Keratin-14;
Short = K14.
ACCESSION P02533
VERSION P02533.4
LOCUS TM109_HUMAN 243 aa linear PRI 5 OCT. 2016
DEFINITION RecName: Full = Transmembrane protein 109; AltName:
Full = Mitsugumin-23; Short = Mg23; Flags: Precursor.
ACCESSION Q9BVC6
VERSION Q9BVC6.1
LOCUS EMIL1_HUMAN 1018 aa linear PRI 5 OCT. 2016
DEFINITION RecName: Full = EMILIN-1; AltName: Full = Elastin microfibril
interface-located protein 1; Short = Elastin microfibril interfacer
1; Flags: Precursor.
ACCESSION Q9Y6C2
VERSION Q9Y6C2.2
LOCUS K1C10_HUMAN 584 aa linear PRI 5 OCT. 2016
DEFINITION RecName: Full = Keratin, type I cytoskeletal 10; AltName:
Full = Cytokeratin-10; Short = CK-10; AltName: Full = Keratin-10;
Short = K10.
ACCESSION P13645
VERSION P13645.6
LOCUS H4_HUMAN 103 aa linear PRI 5 OCT. 2016
DEFINITION RecName: Full = Histone H4.
ACCESSION P62805
VERSION P62805.2
LOCUS PSB4_HUMAN 264 aa linear PRI 5 OCT. 2016
DEFINITION RecName: Full = Proteasome subunit beta type-4; AltName: Full = 26 kDa
prosomal protein; Short = HsBPROS26; Short = PROS-26; AltName:
Full = Macropain beta chain; AltName: Full = Multicatalytic
endopeptidase complex beta chain; AltName: Full = Proteasome beta
chain; AltName: Full = Proteasome chain 3; Short = HsN3; Flags:
Precursor.
ACCESSION P28070
VERSION P28070.4
LOCUS LUM_HUMAN 338 aa linear PRI 5 OCT. 2016
DEFINITION RecName: Full = Lumican; AltName: Full = Keratan sulfate proteoglycan
lumican; Short = KSPG lumican; Flags: Precursor.
ACCESSION P51884
VERSION P51884.2
LOCUS ROA1_HUMAN 372 aa linear PRI 5 OCT. 2016

TABLE H-continued

List of scaffold proteins identified by mass spectrometry analysis of scaffold
Accession numbers are with respect to SwissProt_2015_04_verINS.fasta Version:
2.3, as at 29 Oct. 2016.

DEFINITION RecName: Full = Heterogeneous nuclear ribonucleoprotein A1;
Short = hnRNP A1; AltName: Full = Helix-destabilizing protein; AltName:
Full = Single-strand RNA-binding protein; AltName: Full = hnRNP core
protein A1; Contains: RecName: Full = Heterogeneous nuclear
ACCESSION P09651
VERSION P09651.5
LOCUS EIF3E_HUMAN 445 aa linear PRI 5 OCT. 2016
DEFINITION RecName: Full = Eukaryotic translation initiation factor 3 subunit E;
Short = eIF3e; AltName: Full = Eukaryotic translation initiation factor
3 subunit 6; AltName: Full = Viral integration site protein INT-6
homolog; AltName: Full = eIF-3 p48.
ACCESSION P60228
VERSION P60228.1
LOCUS SAMP_HUMAN 223 aa linear PRI 5 OCT. 2016
DEFINITION RecName: Full = Serum amyloid P-component; Short = SAP; AltName:
Full = 9.5S alpha-1-glycoprotein; Contains: RecName: Full = Serum
amyloid P-component(1-203); Flags: Precursor.
ACCESSION P02743
VERSION P02743.2
LOCUS COEA1_1UMAN 1796 aa linear PRI 5 OCT. 2016
DEFINITION RecName: Full = Collagen alpha-1(XIV) chain; AltName: Full = Undulin;
Flags: Precursor.
ACCESSION Q05707
VERSION Q05707.3
LOCUS POSTN_HUMAN 836 linear PRI 5 OCT. 2016
DEFINITION RecName: Full = Periostin; Short = PN; AltName:
Full = Osteoblast-specific factor 2; Short = OSF-2; Flags: Precursor.
ACCESSION Q15063
VERSION Q15063.2
LOCUS CO3_HUMAN 1663 aa linear PRI 5 OCT. 2016
DEFINITION RecName: Full = Complement C3; AltName: Full = C3 and PZP-like
alpha-2-macroglobulin domain-containing protein 1; Contains:
RecName: Full = Complement C3 beta chain; Contains: RecName:
Full = C3-beta-c; Short = C3bc; Contains: RecName: Full = Complement C3
alpha chain; Contains: RecName: Full = C3a anaphylatoxin; Contains:
RecName: Full = Acylation stimulating protein; Short = ASP; AltName:
Full = C3adesArg; Contains: RecName: Full = Complement C3b alpha'
chain; Contains: RecName: Full = Complement C3c alpha chain fragment
1; Contains: RecName: Full = Complement C3dg fragment; Contains:
RecName: Full = Complement C3g fragment; Contains: RecName:
Full = Complement C3d fragment; Contains: RecName: Full = Complement
C3f fragment; Contains: RecName: Full = Complement C3c alpha' chain
fragment 2; Flags: Precursor.
ACCESSION P01024
VERSION P01024.2
LOCUS VTNC_HUMAN 478 aa linear PRI 5 OCT. 2016
DEFINITION RecName: Full = Vitronectin; Short = VN; AltName: Full = S-protein;
AltName: Full = Serum-spreading factor; AltName: Full = V75; Contains:
RecName: Full = Vitronectin V65 subunit; Contains: RecName:
Full = Vitronectin V10 subunit; Contains: RecName:
Full = Somatomedin-B; Flags: Precursor.
ACCESSION P04004
VERSION P04004.1
LOCUS SNG2_HUMAN 224 aa linear PRI 5 OCT. 2016
DEFINITION RecName: Full = Synaptogyrin-2; AltName: Full = Cellugyrin.
ACCESSION O43760
VERSION O43760.1
LOCUS CO6A1_HUMAN 1028 aa linear PRI 5 OCT. 2016
DEFINITION RecName: Full = Collagen alpha-1(VI) chain; Flags: Precursor.
ACCESSION P12109
VERSION P12109.3
LOCUS APOE_HUMAN 317 aa linear PRI 5 OCT. 2016
DEFINITION RecName: Full = Apolipoprotein E; Short = Apo-E; Flags: Precursor.
ACCESSION P02649
VERSION P02649.1
LOCUS TIF1B_HUMAN 835 aa linear PRI 5 OCT. 2016
DEFINITION RecName: Full = Transcription intermediary factor 1-beta;
Short = TIF1-beta; AltName: Full = E3 SUMO-protein ligase TRIM28;
AltName: Full = KRAB-associated protein 1; Short = KAP-1; AltName:
Full = KRAB-interacting protein 1; Short = KRIP-1; AltName:
Full = Nuclear corepressor KAP-1; AltName: Full = RING finger protein
96; AltName: Full = Tripartite motif-containing protein 28.
ACCESSION Q13263
VERSION Q13263.5

TABLE H-continued

List of scaffold proteins identified by mass spectrometry analysis of scaffold Accession numbers are with respect to SwissProt_2015_04_verINS.fasta Version: 2.3, as at 29 Oct. 2016.

LOCUS PRELP_HUMAN 382 aa linear PRI 5 OCT. 2016
DEFINITION RecName: Full = Prolargin; AltName: Full = Proline-arginine-rich end leucine-rich repeat protein; Flags: Precursor.
ACCESSION P51888
VERSION P51888.1
LOCUS CO6A3_HUMAN 3177 aa linear PRI 5 OCT. 2016
DEFINITION RecName: Full = Collagen alpha-3(VI) chain; Flags: Precursor.
ACCESSION P12111
VERSION P12111.5
LOCUS C1QC_HUMAN 245 aa linear PRI 5 OCT. 2016
DEFINITION RecName: Full = Complement C1q subcomponent subunit C; Flags: Precursor.
ACCESSION P02747
VERSION P02747.3
LOCUS TLN1_HUMAN 2541 aa linear PRI 5 OCT. 2016
DEFINITION RecName: Full = Talin-1.
ACCESSION Q9Y490
VERSION Q9Y490.3
LOCUS CO4A_HUMAN 1744 aa linear PRI 5 OCT. 2016
DEFINITION RecName: Full = Complement C4-A; AltName: Full = Acidic complement C4; AltName: Full = C3 and PZP-like alpha-2-macroglobulin domain-containing protein 2; Contains: RecName: Full = Complement C4 beta chain; Contains: RecName: Full = Complement C4-A alpha chain; Contains: RecName: Full = C4a anaphylatoxin; Contains: RecName: Full = C4b-A; Contains: RecName: Full = C4d-A; Contains: RecName: Full = Complement C4 gamma chain; Flags: Precursor.
ACCESSION P0C0L4
VERSION P0C0L4.2
LOCUS CO6A2_HUMAN 1019 aa linear PRI 5 OCT. 2016
DEFINITION RecName: Full = Collagen alpha-2(VI) chain; Flags: Precursor.
ACCESSION P12110
VERSION P12110.4
LOCUS PGS2_HUMAN 359 aa linear PRI 5 OCT. 2016
DEFINITION RecName: Full = Decorin; AltName: Full = Bone proteoglycan II; AltName: Full = PG-52; AltName: Full = PG40; Flags: Precursor.
ACCESSION P07585
VERSION P07585.1
LOCUS COBA1_HUMAN 1806 aa linear PRI 5 OCT. 2016
DEFINITION RecName: Full = Collagen alpha-1(XI) chain; Flags: Precursor.
ACCESSION P12107
VERSION P12107.4
LOCUS 1433G_HUMAN 247 aa linear PRI 5 OCT. 2016
DEFINITION RecName: Full = 14-3-3 protein gamma; AltName: Full = Protein kinase C inhibitor protein 1; Short = KCIP-1; Contains: RecName: Full = 14-3-3 protein gamma, N-terminally processed.
ACCESSION P61981
VERSION P61981.2
LOCUS SF3B1_HUMAN 1304 aa linear PRI 5 OCT. 2016
DEFINITION RecName: Full = Splicing factor 3B subunit 1; AltName: Full = Pre-mRNA-splicing factor SF3b 155 kDa subunit; Short = SF3b155; AltName: Full = Spliceosome-associated protein 155; Short = SAP 155.
ACCESSION O75533
VERSION O75533.3
LOCUS A2MG_HUMAN 1474 aa linear PRI 5 OCT. 2016
DEFINITION RecName: Full = Alpha-2-macroglobulin; Short = Alpha-2-M; AltName: Full = C3 and PZP-like alpha-2-macroglobulin domain-containing protein 5; Flags: Precursor.
ACCESSION P01023
VERSION P01023.3
LOCUS G3P_HUMAN 335 aa linear PRI 5 OCT. 2016
DEFINITION RecName: Full = Glyceraldehyde-3-phosphate dehydrogenase; Short = GAPDH; AltName: Full = Peptidyl-cysteine S-nitrosylase GAPDH.
ACCESSION P04406
VERSION P04406.3
LOCUS VPS29_HUMAN 182 aa linear PRI 5 OCT. 2016
DEFINITION RecName: Full = Vacuolar protein sorting-associated protein 29; Short = hVPS29; AltName: Full = PEP11 homolog; AltName: Full = Vesicle protein sorting 29.
ACCESSION Q9UBQ0
VERSION Q9UBQ0.1
LOCUS PRKDC_HUMAN 4128 aa linear PRI 5 OCT. 2016
DEFINITION RecName: Full = DNA-dependent protein kinase catalytic subunit; Short = DNA-PK catalytic subunit; Short = DNA-PKcs; AltName: Full = DNPK1; AltName: Full = p460.
ACCESSION P78527
VERSION P78527.3

TABLE H-continued

List of scaffold proteins identified by mass spectrometry analysis of scaffold Accession numbers are with respect to SwissProt_2015_04_verINS.fasta Version: 2.3, as at 29 Oct. 2016.

LOCUS FBLN2_HUMAN 1184 aa linear PRI 5 OCT. 2016
DEFINITION RecName: Full = Fibulin-2; Short = FIBL-2; Flags: Precursor.
ACCESSION P98095
VERSION P98095.2
LOCUS MIME_HUMAN 298 aa linear PRI 5 OCT. 2016
DEFINITION RecName: Full = Mimecan; AltName: Full = Osteoglycin; AltName:
Full = Osteoinductive factor; Short = OIF; Flags: Precursor.
ACCESSION P20774
VERSION P20774.1
LOCUS PFKAL_HUMAN 780 aa linear PRI 5 OCT. 2016
DEFINITION RecName: Full = ATP-dependent 6-phosphofructokinase, liver type;
Short = ATP-PFK; Short = PFK-L; AltName: Full = 6-phosphofructokinase
type B; AltName: Full = Phosphofructo-1-kinase isozyme B;
Short = PFK-B; AltName: Full = Phosphohexokinase.
ACCESSION P17858
VERSION P17858.6
LOCUS FBN1_HUMAN 2871 aa linear PRI 5 OCT. 2016
DEFINITION RecName: Full = Fibrillin-1; Contains: RecName: Full = Asprosin; Flags:
Precursor.
ACCESSION P35555
VERSION P35555.3
LOCUS IGKC_HUMAN 106 aa linear PRI 5 OCT. 2016
DEFINITION RecName: Full = Ig kappa chain C region.
ACCESSION P01834
VERSION P01834.1
LOCUS BGH3_HUMAN 683 aa linear PRI 5 OCT. 2016
DEFINITION RecName: Full = Transforming growth factor-beta-induced protein
ig-h3; Short = Beta ig-h3; AltName: Full = Kerato-epithelin; AltName:
Full = RGD-containing collagen-associated protein; Short = RGD-CAP;
Flags: Precursor.
ACCESSION Q15582
VERSION Q15582.1
LOCUS DYHC1_HUMAN 4646 aa linear PRI 5 OCT. 2016
DEFINITION RecName: Full = Cytoplasmic dynein 1 heavy chain 1; AltName:
Full = Cytoplasmic dynein heavy chain 1; AltName: Full = Dynein heavy
chain, cytosolic.
ACCESSION Q14204
VERSION Q14204.5
LOCUS IGHM_HUMAN 452 aa linear PRI 5 OCT. 2016
DEFINITION RecName: Full = Ig mu chain C region.
ACCESSION P01871
VERSION P01871.3
LOCUS 1433B_HUMAN 246 aa linear PRI 5 OCT. 2016
DEFINITION RecName: Full = 14-3-3 protein beta/alpha; AltName: Full = Protein
1054; AltName: Full = Protein kinase C inhibitor protein 1;
Short = KCIP-1; Contains: RecName: Full = 14-3-3 protein beta/alpha,
N-terminally processed.
ACCESSION P31946
VERSION P31946.3
LOCUS PGS1_HUMAN 388 aa linear PRI 5 OCT. 2016
DEFINITION RecName: Full = Biglycan; AltName: Full = Bone/cartilage proteoglycan
I; AltName: Full = PG-S1; Flags: Precursor.
ACCESSION P21810
VERSION P21810.2
LOCUS COPA_HUMAN 1224 aa linear PRI 5 OCT. 2016
DEFINITION RecName: Full = Coatomer subunit alpha; AltName: Full = Alpha-coat
protein; Short = Alpha-COP; AltName: Full = HEP-COP; Short = HEPCOP;
Contains: RecName: Full = Xenin; AltName: Full = Xenopsin-related
peptide; Contains: RecName: Full = Proxenin.
ACCESSION P53621
VERSION P53621.2
LOCUS SAMP_HUMAN 223 aa linear PRI 5 OCT. 2016
DEFINITION RecName: Full = Serum amyloid P-component; Short = SAP; AltName:
Full = 9.55 alpha-1-glycoprotein; Contains: RecName: Full = Serum
amyloid P-component(1-203); Flags: Precursor.
ACCESSION P02743
VERSION P02743.2
LOCUS SC22B_HUMAN 215 aa linear PRI 5 OCT. 2016
DEFINITION RecName: Full = Vesicle-trafficking protein SEC22b; AltName:
Full = ER-Golgi SNARE of 24 kDa; Short = ERS-24; Short = ERS24; AltName:
Full = SEC22 vesicle-trafficking protein homolog B; AltName:
Full = SEC22 vesicle-trafficking protein-like 1.
ACCESSION O75396
VERSION O75396.4
LOCUS GELS_HUMAN 782 aa linear PRI 5 OCT. 2016
DEFINITION RecName: Full = Gelsolin; AltName: Full = AGEL; AltName:

TABLE H-continued

List of scaffold proteins identified by mass spectrometry analysis of scaffold Accession numbers are with respect to SwissProt_2015_04_verINS.fasta Version: 2.3, as at 29 Oct. 2016.

Full = Actin-depolymerizing factor; Short = ADF; AltName: Full = Brevin;
Flags: Precursor.
ACCESSION P06396
VERSION P06396.1
LOCUS SYDC_HUMAN 501 aa linear PRI 5 OCT. 2016
DEFINITION RecName: Full = Aspartate = tRNA ligase, cytoplasmic; AltName:
Full = Aspartyl-tRNA synthetase; Short = AspRS; AltName: Full = Cell
proliferation-inducing gene 40 protein.
ACCESSION P14868
VERSION P14868.2
LOCUS MPCP_HUMAN 382 aa linear PRI 5 OCT. 2016
DEFINITION RecName: Full = Phosphate carrier protein, mitochondrial; AltName:
Full = Phosphate transport protein; Short = PTP; AltName: Full = Solute
carrier family 25 member 3; Flags: Precursor.
ACCESSION Q00325
VERSION Q00325.2
LOCUS 1433Z_HUMAN 245 aa linear PRI 5 OCT. 2016
DEFINITION RecName: Full = 14-3-3 protein zeta/delta; AltName: Full = Protein
kinase C inhibitor protein 1; Short = KCIP-1.
ACCESSION P63104
VERSION P63104.1
LOCUS CLH1_HUMAN 1675 aa linear PRI 5 OCT. 2016
DEFINITION RecName: Full = Clathrin heavy chain 1; AltName: Full = Clathrin heavy
chain on chromosome 17; Short = CLH-17.
ACCESSION Q00610
VERSION Q00610.5
LOCUS PROF1_HUMAN 140 aa linear PRI 5 OCT. 2016
DEFINITION RecName: Full = Profilin-1; AltName: Full = Epididymis tissue protein
Li 184a; AltName: Full = Profilin I.
ACCESSION P07737
VERSION P07737.2
LOCUS A1AT_HUMAN 418 aa linear PRI 5 OCT. 2016
DEFINITION RecName: Full = Alpha-1-antitrypsin; AltName: Full = Alpha-1 protease
inhibitor; AltName: Full = Alpha-1-antiproteinase; AltName:
Full = Serpin A1; Contains: RecName: Full = Short peptide from AAT;
Short = SPAAT; Flags: Precursor.
ACCESSION P01009
VERSION P01009.3
LOCUS TMED9_HUMAN 235 aa linear PRI 5 OCT. 2016
DEFINITION RecName: Full = Transmembrane emp24 domain-containing protein 9;
AltName: Full = GMP25; AltName: Full = Glycoprotein 25L2; AltName:
Full = p24 family protein alpha-2; Short = p24alpha2; AltName:
Full = p25; Flags: Precursor.
ACCESSION Q9BVK6
VERSION Q9BVK6.2
LOCUS RACK1_HUMAN 317 aa linear PRI 7 SEP. 2016
DEFINITION RecName: Full = Receptor of activated protein C kinase 1; AltName:
Full = Cell proliferation-inducing gene 21 protein; AltName:
Full = Guanine nucleotide-binding protein subunit beta-2-like 1;
AltName: Full = Guanine nucleotide-binding protein subunit beta-like
protein 12.3; AltName: Full = Human lung cancer oncogene 7 protein;
Short = HLC-7; AltName: Full = Receptor for activated C kinase;
Contains: RecName: Full = Receptor of activated protein C kinase 1,
N-terminally processed; AltName: Full = Guanine nucleotide-binding
protein subunit beta-2-like 1, N-terminally processed.
ACCESSION P63244
VERSION P63244.3
LOCUS RAB2A_HUMAN 212 aa linear PRI 5 OCT. 2016
DEFINITION RecName: Full = Ras-related protein Rab-2A.
ACCESSION P61019
VERSION P61019.1
LOCUS MYO1C_HUMAN 1063 aa linear PRI 5 OCT. 2016
DEFINITION RecName: Full = Unconventional myosin-1c; AltName: Full = Myosin I
beta; Short = MMI-beta; Short = MMIb.
ACCESSION O00159
VERSION O00159.4
LOCUS AT2A2_HUMAN 1042 aa linear PRI 5 OCT. 2016
DEFINITION RecName: Full = Sarcoplasmic/endoplasmic reticulum calcium ATPase 2;
Short = SERCA2; Short = SR Ca(2+)-ATPase 2; AltName: Full = Calcium pump
2; AltName: Full = Calcium-transporting ATPase sarcoplasmic reticulum
type, slow twitch skeletal muscle isoform; AltName:
Full = Endoplasmic reticulum class 1/2 Ca(2+)ATPase.
ACCESSION P16615
VERSION P16615.1
LOCUS DQB1_HUMAN 281 aa linear PRI 5 OCT. 2016
DEFINITION RecName: Full = HLA class II histocompatibility antigen, DQ beta 1

TABLE H-continued

List of scaffold proteins identified by mass spectrometry analysis of scaffold
Accession numbers are with respect to SwissProt_2015_04_verINS.fasta Version:
2.3, as at 29 Oct. 2016.

chain; AltName: Full = MHC class II antigen DQB1; Flags: Precursor.
ACCESSION P01920
VERSION P01920.2
LOCUS TGM2_HUMAN 687 aa linear PRI 5 OCT. 2016
DEFINITION RecName: Full = Protein-glutamine gamma-glutamyltransferase 2;
AltName: Full = Tissue transglutaminase; AltName:
Full = Transglutaminase C; Short = TG(C); Short = TGC; Short = TGase C;
AltName: Full = Transglutaminase H; Short = TGase H; AltName:
Full = Transglutaminase-2; Short = TGase-2.
ACCESSION P21980
VERSION P21980.2
LOCUS AP2M1_HUMAN 435 aa linear PRI 5 OCT. 2016
DEFINITION RecName: Full = AP-2 complex subunit mu; AltName: Full = AP-2 mu chain;
AltName: Full = Adaptin-mu2; AltName: Full = Adaptor protein complex
AP-2 subunit mu; AltName: Full = Adaptor-related protein complex 2
subunit mu; AltName: Full = Clathrin assembly protein complex 2 mu
medium chain; AltName: Full = Clathrin coat assembly protein AP50;
AltName: Full = Clathrin coat-associated protein AP50; AltName:
Full = HA2 50 kDa subunit; AltName: Full = Plasma membrane adaptor AP-2
50 kDa protein.
ACCESSION Q96CW1
VERSION Q96CW1.2
LOCUS FINC_HUMAN 2386 aa linear PRI 5 OCT. 2016
DEFINITION RecName: Full = Fibronectin; Short = FN; AltName: Full = Cold-insoluble
globulin; Short = CIG; Contains: RecName: Full = Anastellin; Contains:
RecName: Full = Ugl-Y1; Contains: RecName: Full = Ugl-Y2; Contains:
RecName: Full = Ugl-Y3; Flags: Precursor.
ACCESSION P02751
VERSION P02751.4
LOCUS IF4A1_HUMAN 406 aa linear PRI 5 OCT. 2016
DEFINITION RecName: Full = Eukaryotic initiation factor 4A-I; Short = eIF-4A-I;
Short = eIF4A-I; AltName: Full = ATP-dependent RNA helicase eIF4A-1.
ACCESSION P60842
VERSION P60842.1
LOCUS HNRPU_HUMAN 825 aa linear PRI 5 OCT. 2016
DEFINITION RecName: Full = Heterogeneous nuclear ribonucleoprotein U;
Short = hnRNP U; AltName: Full = Scaffold attachment factor A;
Short = SAF-A; AltName: Full = p120; AltName: Full = pp120.
ACCESSION Q00839
VERSION Q00839.6
LOCUS PRDX1_HUMAN 199 aa linear PRI 5 OCT. 2016
DEFINITION RecName: Full = Peroxiredoxin-1; AltName: Full = Natural killer
cell-enhancing factor A; Short = NKEF-A; AltName:
Full = Proliferation-associated gene protein; Short = PAG; AltName:
Full = Thioredoxin peroxidase 2; AltName: Full = Thioredoxin-dependent
peroxide reductase 2.
ACCESSION Q06830
VERSION Q06830.1
LOCUS DX39B_HUMAN 428 aa linear PRI 5 OCT. 2016
DEFINITION RecName: Full = Spliceosome RNA helicase DDX39B; AltName: Full = 56 kDa
U2AF65-associated protein; AltName: Full = ATP-dependent RNA helicase
p47; AltName: Full = DEAD box protein UAP56; AltName:
Full = HLA-B-associated transcript 1 protein.
ACCESSIONQ013838
VERSION Q13838.1
LOCUS LDHA_HUMAN 332 aa linear PRI 5 OCT. 2016
DEFINITION RecName: Full = L-lactate dehydrogenase A chain; Short = LDH-A;
AltName: Full = Cell proliferation-inducing gene 19 protein; AltName:
Full = LDH muscle subunit; Short = LDH-M; AltName: Full = Renal carcinoma
antigen NY-REN-59.
ACCESSION P00338
VERSION P00338.2
LOCUS RL12_HUMAN 165 aa linear PRI 5 OCT. 2016
DEFINITION RecName: Full = 60S ribosomal protein L12.
ACCESSION P30050
VERSION P30050.1
LOCUS HNRPQ_HUMAN 623 aa linear PRI 5 OCT. 2016
DEFINITION RecName: Full = Heterogeneous nuclear ribonucleoprotein Q;
Short = hnRNP Q; AltName: Full = Glycine- and tyrosine-rich RNA-binding
protein; Short = GRY-RBP; AltName: Full = NS1-associated protein 1;
AltName: Full = Synaptotagmin-binding, cytoplasmic RNA-interacting
protein.
ACCESSION O60506
VERSION O60506.2
LOCUS KPYM_HUMAN 531 aa linear PRI 5 OCT. 2016
DEFINITION RecName: Full = Pyruvate kinase PKM; AltName: Full = Cytosolic thyroid TABLE H-continued List of scaffold proteins identified by mass spectrometry analysis of scaffold Accession numbers are with respect to SwissProt_2015_04_verINS.fasta Version: 2.3, as at 29 Oct. 2016.

hormone-binding protein; Short = CTHBP; AltName: Full = Opa-interacting protein 3; Short = OIP-3; AltName: Full = Pyruvate kinase 2/3; AltName: Full = Pyruvate kinase muscle isozyme; AltName: Full = Thyroid hormone-binding protein 1; Short = THBP1; AltName: Full = Tumor M2-PK; AltName: Full = p58.
ACCESSION P14618
VERSION P14618.4
LOCUS RPN1_HUMAN 607 aa linear PRI 5 OCT. 2016
DEFINITION RecName: Full = Dolichyl-diphosphooligosaccharide--protein glycosyltransferase subunit 1; AltName:
Full = Dolichyl-diphosphooligosaccharide--protein glycosyltransferase 67 kDa subunit; AltName: Full = Ribophorin I; Short = RPN-I; AltName: Full = Ribophorin-1; Flags: Precursor.
ACCESSION P04843
VERSION P04843.1
LOCUS OST48_HUMAN 458 aa linear PRI 5 OCT. 2016
DEFINITION RecName: Full = Dolichyl-diphosphooligosaccharide--protein glycosyltransferase 48 kDa subunit; Short = DDOST 48 kDa subunit; Short = Oligosaccharyl transferase 48 kDa subunit; Flags: Precursor.
ACCESSION P39656
VERSION P39656.4
LOCUS K2C7_HUMAN 489 aa linear PRI 5 OCT. 2016
DEFINITION RecName: Full = Keratin, type II cytoskeletal 7; AltName: Full = Cytokeratin-7; Short = CK-7; AltName: Full = Keratin-7; Short = K7; AltName: Full = Sarcolectin; AltName: Full = Type-II keratin Kb7.
ACCESSION P08729
VERSION P08729.5
LOCUS PHB_HUMAN 272 aa linear PRI 5 OCT. 2016
DEFINITION RecName: Full = Prohibitin.
ACCESSION P35232
VERSION P35232.1
LOCUS ACTH_HUMAN 376 aa linear PRI 5 OCT. 2016
DEFINITION RecName: Full = Actin, gamma-enteric smooth muscle; AltName: Full = Alpha-actin-3; AltName: Full = Gamma-2-actin; AltName: Full = Smooth muscle gamma-actin; Flags: Precursor.
ACCESSION P63267
VERSION P63267.1
LOCUS RL3_HUMAN 403 aa linear PRI 5 OCT. 2016
DEFINITION RecName: Full = 60S ribosomal protein L3; AltName: Full = HIV-1 TAR RNA-binding protein B; Short = TARBP-B.
ACCESSION P39023
VERSION P39023.2
LOCUS RL22_HUMAN 126 aa linear PRI 5 OCT. 2016
DEFINITION RecName: Full = 60S ribosomal protein L22; AltName: Full = EBER-associated protein; Short = EAP; AltName: Full = Epstein-Barr virus small RNA-associated protein; AltName: Full = Heparin-binding protein HBp15.
ACCESSION P35268
VERSION P35268.2
LOCUS RS3_HUMAN 243 aa linear PRI 5 OCT. 2016
DEFINITION RecName: Full = 40S ribosomal protein S3.
ACCESSION P23396
VERSION P23396.2
LOCUS WDR1_HUMAN 606 aa linear PRI 5 OCT. 2016
DEFINITION RecName: Full = WD repeat-containing protein 1; AltName: Full = Actin-interacting protein 1; Short = AIP1; AltName: Full = NORI-1.
ACCESSION O75083
VERSION O75083.4
LOCUS C1QC_HUMAN 245 aa linear PRI 5 OCT. 2016
DEFINITION RecName: Full = Complement C1q subcomponent subunit C; Flags: Precursor.
ACCESSION P02747
VERSION P02747.3
LOCUS IGHG1_HUMAN 330 aa linear PRI 5 OCT. 2016
DEFINITION RecName: Full = Ig gamma-1 chain C region.
ACCESSION P01857
VERSION P01857.1
LOCUS COCA1_1UMAN 3063 aa linear PRI 5 OCT. 2016
DEFINITION RecName: Full = Collagen alpha-1(XII) chain; Flags: Precursor.
ACCESSION Q99715
VERSION Q99715.2
LOCUS HS90B_HUMAN 724 aa linear PRI 5 OCT. 2016
DEFINITION RecName: Full = Heat shock protein HSP 90-beta; Short = HSP 90; AltName: Full = Heat shock 84 kDa; Short = HSP 84; Short = H5P84.
ACCESSION P08238
VERSION P08238.4

TABLE H-continued

List of scaffold proteins identified by mass spectrometry analysis of scaffold Accession numbers are with respect to SwissProt_2015_04_verINS.fasta Version: 2.3, as at 29 Oct. 2016.

LOCUS LMNA_HUMAN 884 aa linear PRI 5 OCT. 2016
DEFINITION RecName: Full = Prelamin-A/C; Contains: RecName: Full = Lamin-NC;
AltName: Full = 70 kDa lamin; AltName: Full = Renal carcinoma antigen
NY-REN-32; Flags: Precursor.
ACCESSION P02545
VERSION P02545.1
LOCUS CH60_HUMAN 573 aa linear PRI 5 OCT. 2016
DEFINITION RecName: Full = 60 kDa heat shock protein, mitochondrial; AltName:
Full = 60 kDa chaperonin; AltName: Full = Chaperonin 60; Short = CPN60;
AltName: Full = Heat shock protein 60; Short = HSP-60; Short = Hsp60;
AltName: Full = HuCHA60; AltName: Full = Mitochondrial matrix protein
P1; AltName: Full = P60 lymphocyte protein; Flags: Precursor.
ACCESSION P10809
VERSION P10809.2
LOCUS HNRPF_HUMAN 415 aa linear PRI 5 OCT. 2016
DEFINITION RecName: Full = Heterogeneous nuclear ribonucleoprotein F;
Short = hnRNP F; AltName: Full = Nucleolin-like protein mcs94-1;
Contains: RecName: Full = Heterogeneous nuclear ribonucleoprotein F,
N-terminally processed.
ACCESSION P52597
VERSION P52597.3
LOCUS TBA1C_HUMAN 449 aa linear PRI 5 OCT. 2016
DEFINITION RecName: Full = Tubulin alpha-1C chain; AltName: Full = Alpha-tubulin
6; AltName: Full = Tubulin alpha-6 chain; Contains: RecName:
Full = Detyrosinated tubulin alpha-1C chain.
ACCESSION Q9B0E3
VERSION Q9B0E3.1
LOCUS PDIA3_HUMAN 505 aa linear PRI 5 OCT. 2016
DEFINITION RecName: Full = Protein disulfide-isomerase A3; AltName: Full = 58 kDa
glucose-regulated protein; AltName: Full = 58 kDa microsomal protein;
Short = p58; AltName: Full = Disulfide isomerase ER-60; AltName:
Full = Endoplasmic reticulum resident protein 57; Short = ER protein
57; Short = ERp57; AltName: Full = Endoplasmic reticulum resident
protein 60; Short = ER protein 60; Short = ERp60; Flags: Precursor.
ACCESSION P30101
VERSION P30101.4
LOCUS K1C19_HUMAN 400 aa linear PRI 5 OCT. 2016
DEFINITION RecName: Full = Keratin, type I cytoskeletal 19; AltName:
Full = Cytokeratin-19; Short = CK-19; AltName: Full = Keratin-19;
Short = K19.
ACCESSION P08727
VERSION P08727.4
LOCUS TBB5_HUMAN 444 aa linear PRI 5 OCT. 2016
DEFINITION RecName: Full = Tubulin beta chain; AltName: Full = Tubulin beta-5
chain.
ACCESSION P07437
VERSION P07437.2
LOCUS TSP2_HUMAN 1172 aa linear PRI 5 OCT. 2016
DEFINITION RecName: Full = Thrombospondin-2; Flags: Precursor.
ACCESSION P35442
VERSION P35442.2
LOCUS ACTB_HUMAN 375 aa linear PRI 5 OCT. 2016
DEFINITION RecName: Full = Actin, cytoplasmic 1; AltName: Full = Beta-actin;
Contains: RecName: Full = Actin, cytoplasmic 1, N-terminally
processed.
ACCESSION P60709
VERSION P60709.1
LOCUS HS90A_HUMAN 732 aa linear PRI 5 OCT. 2016
DEFINITION RecName: Full = Heat shock protein HSP 90-alpha; AltName: Full = Heat
shock 86 kDa; Short = HSP 86; Short = H5P86; AltName:
Full = Lipopolysaccharide-associated protein 2; Short = LAP-2;
Short = LPS-associated protein 2; AltName: Full = Renal carcinoma
antigen NY-REN-38.
ACCESSION P07900
VERSION P07900.5
LOCUS FAS_HUMAN 2511 aa linear PRI 5 OCT. 2016
DEFINITION RecName: Full = Fatty acid synthase; Includes: RecName:
Full = [Acyl-carrier-protein] S-acetyltransferase; Includes: RecName:
Full = [Acyl-carrier-protein] S-malonyltransferase; Includes:
RecName: Full = 3-oxoacyl[-acyl-carrier-protein] synthase; Includes:
RecName: Full = 3-oxoacyl-[acyl-carrier-protein] reductase; Includes:
RecName: Full = 3-hydroxyacyl-[acyl-carrier-protein] dehydratase;
Includes: RecName: Full = EnoyNl-[acyl-carrier-protein] reductase;
Includes: RecName: Full = Oleoyl-[acyl-carrier-protein] hydrolase.
ACCESSION P49327
VERSION P49327.3

TABLE H-continued

List of scaffold proteins identified by mass spectrometry analysis of scaffold Accession numbers are with respect to SwissProt_2015_04_verINS.fasta Version: 2.3, as at 29 Oct. 2016.

LOCUS PLEC_HUMAN 4684 aa linear PRI 5 OCT. 2016
DEFINITION RecName: Full = Plectin; Short = PCN; Short = PLTN; AltName:
Full = Hemidesmosomal protein 1; Short = HD1; AltName: Full = Plectin-1.
ACCESSION O15149
VERSION O15149.3
LOCUS HSP7C_HUMAN 646 aa linear PRI 5 OCT. 2016
DEFINITION RecName: Full = Heat shock cognate 71 kDa protein; AltName: Full = Heat
shock 70 kDa protein 8; AltName: Full = Lipopolysaccharide-associated
protein 1; Short = LAP-1; Short = LPS-associated protein 1.
ACCESSION P11142
VERSION P11142.1
LOCUS HNRC2_HUMAN 293 aa linear PRI 5 OCT. 2016
DEFINITION RecName: Full = Heterogeneous nuclear ribonucleoprotein C-like 2;
Short = hnRNP C-like-2.
ACCESSION B2RXH8
VERSION B2RXH8.1
LOCUS MOES_HUMAN 577 aa linear PRI 5 OCT. 2016
DEFINITION RecName: Full = Moesin; AltName: Full = Membrane-organizing extension
spike protein.
ACCESSION P26038
VERSION P26038.3
LOCUS TAGL_HUMAN 201 aa linear PRI 5 OCT. 2016
DEFINITION RecName: Full = Transgelin; AltName: Full = 22 kDa actin-binding
protein; AltName: Full = Protein WS3-10; AltName: Full = Smooth muscle
protein 22-alpha; Short = SM22-alpha.
ACCESSION Q01995
VERSION Q01995.4
LOCUS VDAC2_HUMAN 294 aa linear PRI 5 OCT. 2016
DEFINITION RecName: Full = Voltage-dependent anion-selective channel protein 2;
Short = VDAC-2; Short = hVDAC2; AltName: Full = Outer mitochondrial
membrane protein porin 2.
ACCESSION P45880
VERSION P45880.2
LOCUS ANXA2_HUMAN 339 aa linear PRI 5 OCT. 2016
DEFINITION RecName: Full = Annexin A2; AltName: Full = Annexin II; AltName:
Full = Annexin-2; AltName: Full = Calpactin I heavy chain; AltName:
Full = Calpactin-1 heavy chain; AltName: Full = Chromobindin-8;
AltName: Full = Lipocortin II; AltName: Full = Placental anticoagulant
protein IV; Short = PAP-IV; AltName: Full = Protein I; AltName:
Full = p36.
ACCESSION P07355
VERSION P07355.2
LOCUS CKAP4_HUMAN 802 aa linear PRI 7 SEP. 2016
DEFINITION RecName: Full = Cytoskeleton-associated protein 4; AltName:
Full = 63-kDa cytoskeleton-linking membrane protein; Short = Climp-63;
Short = p63.
ACCESSION Q07065
VERSION Q07065.2
LOCUS ATPB_HUMAN 529 aa linear PRI 5 OCT. 2016
DEFINITION RecName: Full = ATP synthase subunit beta, mitochondrial; Flags:
Precursor.
ACCESSION P06576
VERSION P06576.3
LOCUS VIME_HUMAN 466 aa linear PRI 5 OCT. 2016
DEFINITION RecName: Full = Vimentin.
ACCESSION P08670
VERSION P08670.4
LOCUS ATPA_HUMAN 553 aa linear PRI 5 OCT. 2016
DEFINITION RecName: Full = ATP synthase subunit alpha, mitochondrial; Flags:
Precursor.
ACCESSION P25705
VERSION P25705.1
LOCUS HS71A_HUMAN 641 aa linear PRI 5 OCT. 2016
DEFINITION RecName: Full = Heat shock 70 kDa protein 1A; AltName: Full = Heat
shock 70 kDa protein 1; Short = HSP70-1; Short = HSP70.1.
ACCESSION P0DMV8
VERSION P0DMV8.1
LOCUS TSP1_HUMAN 1170 aa linear PRI 5 OCT. 2016
DEFINITION RecName: Full = Thrombospondin-1; Flags: Precursor.
ACCESSION P07996
VERSION P07996.2
LOCUS TKT_HUMAN 623 aa linear PRI 5 OCT. 2016
DEFINITION RecName: Full = Transketolase; Short = TK.
ACCESSION P29401
VERSION P29401.3
LOCUS EF1A1_HUMAN 462 aa linear PRI 5 OCT. 2016

TABLE H-continued

List of scaffold proteins identified by mass spectrometry analysis of scaffold Accession numbers are with respect to SwissProt_2015_04_verINS.fasta Version: 2.3, as at 29 Oct. 2016.

DEFINITION RecName: Full = Elongation factor 1-alpha 1; Short = EF-1-alpha-1; AltName: Full = Elongation factor Tu; Short = EF-Tu; AltName:
Full = Eukaryotic elongation factor 1 A-1; Short = eEF1A-1; AltName:
Full = Leukocyte receptor cluster member 7.
ACCESSION P68104
VERSION P68104.1
LOCUS K1C18_HUMAN 430 aa linear PRI 5 OCT. 2016
DEFINITION RecName: Full = Keratin, type I cytoskeletal 18; AltName: Full = Cell proliferation-inducing gene 46 protein; AltName:
Full = Cytokeratin-18; Short = CK-18; AltName: Full = Keratin-18;
Short = K18.
ACCESSION P05783
VERSION P05783.2
LOCUS TBB4B_HUMAN 445 aa linear PRI 5 OCT. 2016
DEFINITION RecName: Full = Tubulin beta-4B chain; AltName: Full = Tubulin beta-2 chain; AltName: Full = Tubulin beta-2C chain.
ACCESSION P68371
VERSION P68371.1
LOCUS TENA_HUMAN 2201 aa linear PRI 5 OCT. 2016
DEFINITION RecName: Full = Tenascin; Short = TN; AltName: Full = Cytotactin; AltName: Full = GMEM; AltName: Full = GP 150-225; AltName:
Full = Glioma-associated-extracellular matrix antigen; AltName:
Full = Hexabrachion; AltName: Full = JI; AltName: Full = Myotendinous antigen; AltName: Full = Neuronectin; AltName: Full = Tenascin-C;
Short = TN-C; Flags: Precursor.
ACCESSION P24821
VERSION P24821.3
LOCUS FLNA_HUMAN 2647 aa linear PRI 5 OCT. 2016
DEFINITION RecName: Full = Filamin-A; Short = FLN-A; AltName: Full = Actin-binding protein 280; Short = ABP-280; AltName: Full = Alpha-filamin; AltName:
Full = Endothelial actin-binding protein; AltName: Full = Filamin-1;
AltName: Full = Non-muscle filamin.
ACCESSION P21333
VERSION P21333.4
LOCUS K2C8_HUMAN 483 aa linear PRI 5 OCT. 2016
DEFINITION RecName: Full = Keratin, type II cytoskeletal 8; AltName:
Full = Cytokeratin-8; Short = CK-8; AltName: Full = Keratin-8; Short = K8;
AltName: Full = Type-II keratin Kb8.
ACCESSION P05787
VERSION P05787.7
LOCUS LMAN1_HUMAN 510 aa linear PRI 5 OCT. 2016
DEFINITION RecName: Full = Protein ERGIC-53; AltName: Full = ER-Golgi intermediate compartment 53 kDa protein; AltName: Full = Gp58; AltName:
Full = Intracellular mannose-specific lectin MR60; AltName:
Full = Lectin mannose-binding 1; Flags: Precursor.
ACCESSION P49257
VERSION P49257.2
LOCUS ACTN1_HUMAN 892 aa linear PRI 5 OCT. 2016
DEFINITION RecName: Full = Alpha-actinin-1; AltName: Full = Alpha-actinin cytoskeletal isoform; AltName: Full = F-actin cross-linking protein;
AltName: Full = Non-muscle alpha-actinin-1.
ACCESSION P12814
VERSION P12814.2
LOCUS ENOA_HUMAN 434 aa linear PRI 5 OCT. 2016
DEFINITION RecName: Full = Alpha-enolase; AltName: Full = 2-phospho-D-glycerate hydro-lyase; AltName: Full = C-myc promoter-binding protein; AltName:
Full = Enolase 1; AltName: Full = MBP-1; AltName: Full = MPB-1; AltName:
Full = Non-neural enolase; Short = NNE; AltName: Full = Phosphopyruvate hydratase; AltName: Full = Plasminogen-binding protein.
ACCESSION P06733
VERSION P06733.2
LOCUS F13A_HUMAN 732 aa linear PRI 5 OCT. 2016
DEFINITION RecName: Full = Coagulation factor XIII A chain; Short = Coagulation factor XIIIa; AltName: Full = Protein-glutamine
gamma-glutamyltransferase A chain; AltName: Full = Transglutaminase A chain; Flags: Precursor.
ACCESSION P00488
VERSION P00488.4
LOCUS HSPB1_HUMAN 205 aa linear PRI 5 OCT. 2016
DEFINITION RecName: Full = Heat shock protein beta-1; Short = HspB1; AltName:
Full = 28 kDa heat shock protein; AltName: Full = Estrogen-regulated 24 kDa protein; AltName: Full = Heat shock 27 kDa protein; Short = HSP 27;
AltName: Full = Stress-responsive protein 27; Short = SRP27.
ACCESSION P04792
VERSION P04792.2
LOCUS MYH9_HUMAN 1960 aa linear PRI 5 OCT. 2016

TABLE H-continued

List of scaffold proteins identified by mass spectrometry analysis of scaffold
Accession numbers are with respect to SwissProt_2015_04_verINS.fasta Version:
2.3, as at 29 Oct. 2016.

DEFINITION RecName: Full = Myosin-9; AltName: Full = Cellular myosin heavy chain,
type A; AltName: Full = Myosin heavy chain 9; AltName: Full = Myosin
heavy chain, non-muscle IIa; AltName: Full = Non-muscle myosin heavy
chain A; Short = NMMHC-A; AltName: Full = Non-muscle myosin heavy chain
IIa; Short = NMMHC II-a; Short = NMMHC-IIA.
ACCESSION P35579
VERSION P35579.4
LOCUS VDAC1_HUMAN 283 aa linear PRI 5 OCT. 2016
DEFINITIO RecName: Full = Voltage-dependent anion-selective channel protein 1;
Short = VDAC-1; Short = hVDAC1; AltName: Full = Outer mitochondrial
membrane protein porin 1; AltName: Full = Plasmalemmal porin;
AltName: Full = Porin 31HL; AltName: Full = Porin 31HM.
ACCESSION P21796
VERSION P21796.2
LOCUS ENPL_HUMAN 803 aa linear PRI 5 OCT. 2016
DEFINITION RecName: Full = Endoplasmin; AltName: Full = 94 kDa glucose-regulated
protein; Short = GRP-94; AltName: Full = Heat shock protein 90 kDa beta
member 1; AltName: Full = Tumor rejection antigen 1; AltName:
Full = gp96 homolog; Flags: Precursor.
ACCESSION P14625
VERSION P14625.1
LOCUS FBLN1_HUMAN 703 aa linear PRI 5 OCT. 2016
DEFINITION RecName: Full = Fibulin-1; Short = FIBL-1; Flags: Precursor.
ACCESSION P23142
VERSION P23142.4
LOCUS K1C10_HUMAN 584 aa linear PRI 5 OCT. 2016
DEFINITION RecName: Full = Keratin, type I cytoskeletal 10; AltName:
Full = Cytokeratin-10; Short = CK-10; AltName: Full = Keratin-10;
Short = K10.
ACCESSION P13645
VERSION P13645.6
LOCUS ROA1_HUMAN 372 aa linear PRI 5 OCT. 2016
DEFINITION RecName: Full = Heterogeneous nuclear ribonucleoprotein A1;
Short = hnRNP A1; AltName: Full = Helix-destabilizing protein; AltName:
Full = Single-strand RNA-binding protein; AltName: Full = hnRNP core
protein A1; Contains: RecName: Full = Heterogeneous nuclear
ribonucleoprotein A1, N-terminally processed.
ACCESSION P09651
VERSION P09651.5
LOCUS ANXA5_HUMAN 320 aa linear PRI 5 OCT. 2016
DEFINITION RecName: Full = Annexin A5; AltName: Full = Anchorin CII; AltName:
Full = Annexin V; AltName: Full = Annexin-5; AltName: Full = Calphobindin
I; Short = CBP-I; AltName: Full = Endonexin II; AltName:
Full = Lipocortin V; AltName: Full = Placental anticoagulant protein 4;
Short = PP4; AltName: Full = Placental anticoagulant protein I;
Short = PAP-I; AltName: Full = Thromboplastin inhibitor; AltName:
Full = Vascular anticoagulant-alpha; Short = VAC-alpha.
ACCESSION P08758
VERSION P08758.2

---

The invention claimed is:

1. A method for determining one or more properties of a tumour in a patient, the method comprising:
    seeding a 3-dimensional cell-free scaffold obtained from the tumour in the patient with cancer cells, wherein the cancer cells are not taken from the tumour in the patient;
    culturing the cancer cells in the scaffold;
    assaying the cultured cancer cells for the presence of target molecules indicative of the expression of one or more genes in the cells; and
    determining one or more properties of the tumour from which the 3-dimensional cell-free scaffold was obtained based on the presence of target molecules indicative of the expression of one or more genes in the cells in the assay; and wherein the one or more genes are selected from the group consisting of:
    ACTN1; AIFM1; ALDH2; ALDOA; ANXA1; AP1B1; AP2B1; ATM; ATXN1; BAG2; BAG3; BHLHE40; BIRC5; BTBD2; BYSL; C3; CAMK2B; CAMK4; CARD11; CASP3; CAV1; CEACAM1; CHD3; COL17A1; CRCT1; DAPK1; DMD; DPYSL2; DYSF; E2F1; EGFR; EIF2AK3; EP300; EPOR; ERBB3; ESR1; FANCC; FEN1; FHIT; FKBP5; FN1; FOS; FRMD6; GADD45A; GADD45G; GOLM1; GSN; GSTP1; HCK; HDAC5; HSPB1; HSPD1; IGF1R; IL4R; ITGA6; ITGB4; JAK1; JUN; KAT2B; KIF15; KRT18; KRT8; LYST; LRP1; LRPS; MAP2; MAP3K14; MAP3K5; MAPK3; MAPKAPK3; MST1R; NDRG1; NME1-NME2; NOS3; NPAS2; NPHP1; NQO1; NR3C; PIK3CG; PAEP; PAK1; PARK2; PARP1; PDE4D; PFN2; PIM1; PTN; PKD1; PLA2G4A; PLD1; PPARGC1A; PPL; PPM1A; PPP1R15A; PPP2R1B; PRKCA; PRNP; PSG9; PSME3; RABAC1; RAC2; RASA1; RBL1; RGS2; RPS6KA3; RUNX1T1; SH2B3; SH3GL3; SLC9A3R1; SMAD4; SNX9; SORBS2; SOX9;SP1; SPG7; SREBF1; STUB1; SUMO4; SVIL; TGFB1 11; TH; TNFAIP3; TNFRSF14; TNIK; TP73; TPD52L1; TRIO; TUBA1A; VIM; WEE1; XPO5;YAP1; and ZNF259.

2. A method according to claim 1 wherein the tumour is a breast cancer tumour.

3. A method according to claim 1 wherein the one or more properties of the tumour from which the 3-dimensional cell-free scaffold was obtained are selected from invasiveness, migration, tumour malignancy grade, tumour malignancy potential, tumour recurrence, resistance to treatment and tumour proliferation.

4. A method according to claim 1 wherein the one or more genes are one or more markers of tumour progression.

5. A method according to claim 4 wherein the one or more markers of tumour progression are selected from markers of proliferation, markers of differentiation, markers of cancer stem cells, and markers of epithelial-mesenchymal transition (EMT).

6. A method according to claim 1 wherein the cancer cells are breast cancer cells.

7. A method according to claim 6 wherein the cancer cells are selected from MCF7, MDA231 and T47D cells.

8. A method according to claim 1 which further comprises obtaining the 3-dimensional cell-free scaffold from the tumour in the patient.

9. A method for determining a suitable treatment for a patient with a tumour, the method comprising:
    determining one or more properties of the tumour from which the 3-dimensional cell-free scaffold was obtained by a method according to claim 1; and
    determining a suitable treatment based on the properties of the tumour from which the 3-dimensional cell-free scaffold was obtained.

10. A method of treating a patient with a tumour, the method comprising:
   determining the suitability of a treatment in the patient by a method according to claim 9; and
   applying the treatment to the patient.

11. A method of treating patient with a tumour, the method comprising:
   determining one or more properties of the tumour from which the 3-dimensional cell-free scaffold was obtained in the patient by a method according to claim 1;
   selecting a suitable treatment based on the one or more properties of the tumour from which the 3-dimensional cell-free scaffold was obtained; and
   providing the treatment to the patient.

12. A method according to claim 1, wherein the patient is a human patient.

13. A method according to claim 2 wherein the one or more properties of the tumour from which the 3-dimensional cell-free scaffold was obtained are selected from invasiveness, migration, tumour malignancy grade, tumour malignancy potential, tumour recurrence, resistance to treatment and tumour proliferation.

* * * * *

SEQUENCE LISTING

<160> NUMBER OF SEQ ID NOS: 3

<210> SEQ ID NO 1
<211> LENGTH: 57
<212> TYPE: DNA
<213> ORGANISM: Artificial
<220> FEATURE:
<223> OTHER INFORMATION: Adapter ligated oligo-dT primer
<220> FEATURE:
<221> NAME/KEY: misc_feature
<222> LOCATION: (57)..(57)
<223> OTHER INFORMATION: n is a, c, g, or t

<400> SEQUENCE: 1
aagcagtggt atcaacgcag agtactttt tttttttttt tttttttttt tttttvn        57

<210> SEQ ID NO 2

```
<211> LENGTH: 30
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (28)..(28)
<223> OTHER INFORMATION: g is riboguanosine
<220> FEATURE:
<221> NAME/KEY: misc_feature
<222> LOCATION: (29)..(29)
<223> OTHER INFORMATION: g is riboguanosine
<220> FEATURE:
<221> NAME/KEY: misc_feature
<222> LOCATION: (30)..(30)
<223> OTHER INFORMATION: g is locked nucleic acid modified guanosine

<400> SEQUENCE: 2
aagcagtggt atcaacgcag agtacatggg                               30

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
aagcagtggt atcaacgcag agt                                      23
```